US011529424B2

(12) United States Patent
Paderi et al.

(10) Patent No.: US 11,529,424 B2
(45) Date of Patent: Dec. 20, 2022

(54) SYNTHETIC BIOCONJUGATES

(71) Applicant: Symic Holdings, Inc., San Francisco, CA (US)

(72) Inventors: John Eric Paderi, San Francisco, CA (US); Julia Chen, San Francisco, CA (US); Sharmistha Saha, San Francisco, CA (US)

(73) Assignee: Symic Holdings, Inc., Emeryville, CA (US)

( * ) Notice: Subject to any disclaimer, the term of this patent is extended or adjusted under 35 U.S.C. 154(b) by 0 days.

(21) Appl. No.: 16/629,167

(22) PCT Filed: Jul. 9, 2018

(86) PCT No.: PCT/US2018/041259
§ 371 (c)(1),
(2) Date: Jan. 7, 2020

(87) PCT Pub. No.: WO2019/010484
PCT Pub. Date: Jan. 10, 2019

(65) Prior Publication Data
US 2020/0222548 A1  Jul. 16, 2020

Related U.S. Application Data

(60) Provisional application No. 62/530,047, filed on Jul. 7, 2017.

(51) Int. Cl.
| | |
|---|---|
| *A61K 38/00* | (2006.01) |
| *A61K 47/61* | (2017.01) |
| *A61K 47/64* | (2017.01) |
| *A61P 9/00* | (2006.01) |
| *C07K 7/08* | (2006.01) |
| *C07K 14/00* | (2006.01) |

(52) U.S. Cl.
CPC ............ *A61K 47/61* (2017.08); *A61K 47/64* (2017.08); *A61P 9/00* (2018.01); *C07K 7/08* (2013.01); *C07K 14/00* (2013.01)

(58) Field of Classification Search
CPC ........ A61K 47/61; A61K 47/64; A61K 38/00; A61K 47/65; A61P 9/00; A61P 1/16; A61P 43/00; C07K 14/00; C07K 7/08; C07K 14/001
See application file for complete search history.

(56) References Cited

U.S. PATENT DOCUMENTS

| | | |
|---|---|---|
| 4,683,298 A | 7/1987 | Yalpani |
| 5,271,929 A | 12/1993 | Hashiguchi et al. |
| 5,342,830 A | 8/1994 | Scarborough |
| 5,547,936 A | 8/1996 | Ruoslahti et al. |
| 5,693,625 A | 12/1997 | Barritault et al. |
| 5,852,004 A | 12/1998 | Barritault et al. |
| 5,955,578 A | 9/1999 | Pierschbacher et al. |
| 5,997,895 A | 12/1999 | Narotam et al. |
| 6,051,701 A | 4/2000 | Cialdi et al. |
| 6,703,491 B1 | 3/2004 | Homburger et al. |
| 6,719,974 B1 | 4/2004 | Rothman et al. |
| 6,822,071 B1 | 11/2004 | Stephens et al. |
| 6,864,235 B1 | 3/2005 | Turley et al. |
| 6,932,973 B2 | 8/2005 | Barritault et al. |
| 7,098,194 B2 | 8/2006 | Chenite et al. |
| 7,534,436 B2 | 5/2009 | Courty et al. |
| 7,592,009 B2 | 9/2009 | Hubbell et al. |
| 7,597,889 B1 | 10/2009 | Armour et al. |
| 7,671,018 B2 | 3/2010 | Carson et al. |
| 7,709,439 B2 | 5/2010 | Helmus et al. |
| 7,732,427 B2 | 6/2010 | Kiick et al. |
| 7,737,131 B2 | 6/2010 | Kiick et al. |
| 7,803,905 B2 | 9/2010 | Farach-Carson et al. |
| 7,842,667 B2 | 11/2010 | Seliktar et al. |
| 7,851,445 B2 | 12/2010 | Stupp et al. |
| 7,855,187 B1 | 12/2010 | Prestwich et al. |
| 7,862,831 B2 | 1/2011 | Wang et al. |
| 7,897,165 B2 | 3/2011 | Elisseeff et al. |
| 7,919,111 B2 | 4/2011 | Chudzik et al. |
| 8,007,774 B2 | 8/2011 | Seliktar et al. |
| 8,114,834 B2 | 2/2012 | Hsu et al. |
| 8,188,220 B2 | 5/2012 | Ruoslahti et al. |
| 8,268,950 B2 | 9/2012 | Elisseeff |
| 8,283,414 B2 | 10/2012 | Yu et al. |
| 8,304,388 B2 | 11/2012 | Chettibi et al. |
| 8,314,195 B2 | 11/2012 | Elisseeff |

(Continued)

FOREIGN PATENT DOCUMENTS

| | | |
|---|---|---|
| CA | 2299687 | 2/1999 |
| CN | 101906163 | 12/2010 |

(Continued)

OTHER PUBLICATIONS

International Preliminary Report on Patentability for International Application No. PCT/US2018/041259 dated Jan. 7, 2020. 7 pages.
International Search Report and Written Opinion for International Application No. PCT/US2018/041259 dated Dec. 20, 2018. (11 pages).
Jin et al., Collagen mimetic peptide engineered M13 bacteriophage for collagen targeting and imaging in cancer, Biomaterials 2014, vol. 35, pp. 9236-9245.
Miyazaki et al., "A Collagen-Binding Mimetic of Neural Cell Adhesion Molecule," Bioconjugate Chemistry 2008, vol. 19, No. 6, pp. 1119-1123.
Extended European Search Report for European Application No. 18829053.0 dated Mar. 24, 2021. 10 pages.
A National Public Health Agenda for Osteoarthritis 2010, www.cdc.gov/arthritis/docs/OAagenda.pdf (2010).

(Continued)

*Primary Examiner* — Aradhana Sasan
*Assistant Examiner* — Mercy H Sabila
(74) *Attorney, Agent, or Firm* — Sheppard Mullin Richter & Hampton LLP

(57) ABSTRACT

Provided herein are bioconjugates comprising a backbone and at least one branched or unbranched peptide having at least one collagen-binding unit covalently bonded thereto via a spacer and methods of use thereof.

22 Claims, 18 Drawing Sheets
Specification includes a Sequence Listing.

(56) References Cited

U.S. PATENT DOCUMENTS

| | | | |
|---|---|---|---|
| 8,329,673 B2 | 12/2012 | Prestwich et al. | |
| 8,338,390 B2 | 12/2012 | Kiick et al. | |
| 8,343,764 B2 | 1/2013 | Abad et al. | |
| 8,343,942 B2 | 1/2013 | Oottamasathien et al. | |
| 8,367,639 B2 | 2/2013 | Kiick et al. | |
| 8,389,467 B2 | 3/2013 | Chaput et al. | |
| 8,415,325 B2 | 4/2013 | Kiick et al. | |
| 8,431,146 B2 | 4/2013 | Harley et al. | |
| 8,431,226 B2 | 4/2013 | Huerta et al. | |
| 8,450,271 B2 | 5/2013 | Shah et al. | |
| 8,470,780 B2 | 6/2013 | Ruoslahti et al. | |
| 8,476,220 B2 | 7/2013 | Barritault et al. | |
| 8,557,774 B2 | 10/2013 | Vandroux et al. | |
| 8,673,333 B2 | 3/2014 | Elisseeff et al. | |
| 8,703,740 B2 | 4/2014 | Cho et al. | |
| 8,790,631 B2 | 7/2014 | Barritault et al. | |
| 8,846,003 B2 | 9/2014 | Pantich et al. | |
| 8,883,182 B2 | 11/2014 | Ratcliffe et al. | |
| 8,883,964 B2 | 11/2014 | Yu et al. | |
| 9,173,919 B2 | 11/2015 | Paderi et al. | |
| 9,200,039 B2 | 12/2015 | Panitch et al. | |
| 9,217,016 B2 | 12/2015 | Panitch et al. | |
| 9,474,782 B2 | 10/2016 | Kichler et al. | |
| 9,512,192 B2 | 12/2016 | Pantich et al. | |
| 9,872,887 B2 | 1/2018 | Panitch et al. | |
| 10,689,425 B2 | 6/2020 | Pantich et al. | |
| 2002/0098153 A1 | 7/2002 | Allen et al. | |
| 2002/0183282 A1 | 12/2002 | Dahricorreia et al. | |
| 2003/0087255 A1 | 5/2003 | Barritault et al. | |
| 2003/0124705 A1 | 7/2003 | Berry et al. | |
| 2003/0149173 A1 | 8/2003 | Rhee et al. | |
| 2003/0199615 A1 | 10/2003 | Chaput et al. | |
| 2004/0091540 A1 | 5/2004 | Desrosiers et al. | |
| 2004/0127416 A1 | 7/2004 | Massia et al. | |
| 2004/0214272 A1 | 10/2004 | La Rosa et al. | |
| 2004/0236092 A1 | 11/2004 | Dziarski et al. | |
| 2005/0043221 A1 | 2/2005 | Fallon et al. | |
| 2005/0069572 A1 | 3/2005 | Williams et al. | |
| 2005/0108791 A1 | 5/2005 | Edgerton | |
| 2005/0113297 A1 | 5/2005 | Francois et al. | |
| 2005/0147679 A1 | 7/2005 | Petito et al. | |
| 2005/0187146 A1 | 8/2005 | Helmus et al. | |
| 2005/0196377 A1 | 9/2005 | Ratcliffe et al. | |
| 2005/0208114 A1 | 9/2005 | Petito et al. | |
| 2006/0024696 A1 | 2/2006 | Kapur et al. | |
| 2006/0075522 A1 | 4/2006 | Cleveland et al. | |
| 2006/0123505 A1 | 6/2006 | Kikuchi et al. | |
| 2006/0241022 A1 | 10/2006 | Bowen et al. | |
| 2006/0252692 A1 | 11/2006 | Lasser et al. | |
| 2007/0098675 A1 | 5/2007 | Elisseeff et al. | |
| 2007/0124833 A1 | 5/2007 | Abad et al. | |
| 2007/0141020 A1 | 6/2007 | Barritault et al. | |
| 2007/0167441 A1 | 7/2007 | Halbrook et al. | |
| 2007/0218102 A1 | 9/2007 | Chudzik et al. | |
| 2007/0224247 A1 | 9/2007 | Chudzik et al. | |
| 2007/0298071 A1 | 12/2007 | Harley et al. | |
| 2008/0069774 A1 | 3/2008 | Liotta et al. | |
| 2008/0090998 A1 | 4/2008 | Abad et al. | |
| 2008/0131466 A1 | 6/2008 | Reed et al. | |
| 2008/0247995 A1 | 10/2008 | Decarlo et al. | |
| 2008/0248569 A1 | 10/2008 | Mata et al. | |
| 2008/0293640 A1 | 11/2008 | Brophy et al. | |
| 2009/0022771 A1 | 1/2009 | Lynn et al. | |
| 2009/0030525 A1 | 1/2009 | Desrosiers et al. | |
| 2009/0075281 A1 | 3/2009 | Hristova et al. | |
| 2009/0092674 A1 | 4/2009 | Ingram et al. | |
| 2009/0100536 A1 | 4/2009 | Adams et al. | |
| 2009/0158452 A1 | 6/2009 | Johnson et al. | |
| 2009/0162436 A1 | 6/2009 | Carson et al. | |
| 2009/0183270 A1 | 7/2009 | Adams et al. | |
| 2009/0202616 A1 | 8/2009 | Chong et al. | |
| 2009/0214598 A1* | 8/2009 | Blaszczak | A61P 1/04 530/322 |
| 2009/0324722 A1 | 12/2009 | Elisseeff | |
| 2010/0003329 A1 | 1/2010 | Elisseeff | |
| 2010/0004196 A1 | 1/2010 | De Agostini et al. | |
| 2010/0017904 A1 | 1/2010 | Abad et al. | |
| 2010/0021545 A1 | 1/2010 | Chaput et al. | |
| 2010/0029549 A1 | 2/2010 | Chaput et al. | |
| 2010/0111842 A1 | 5/2010 | Boyden et al. | |
| 2010/0119577 A1 | 5/2010 | Min et al. | |
| 2010/0137510 A1 | 6/2010 | Seliktar et al. | |
| 2010/0166830 A1 | 7/2010 | Harley et al. | |
| 2010/0210509 A1 | 8/2010 | Oh et al. | |
| 2010/0227836 A1 | 9/2010 | Elisseeff et al. | |
| 2011/0020298 A1* | 1/2011 | Panitch | C07K 9/00 424/93.7 |
| 2011/0038828 A1 | 2/2011 | Seliktar et al. | |
| 2011/0087152 A1 | 4/2011 | David et al. | |
| 2011/0207669 A1 | 8/2011 | Vandroux et al. | |
| 2011/0214206 A1 | 9/2011 | La Rosa et al. | |
| 2011/0238000 A1 | 9/2011 | Seliktar et al. | |
| 2011/0258734 A1 | 10/2011 | Adams et al. | |
| 2011/0269208 A1 | 11/2011 | Burdick et al. | |
| 2012/0020911 A1 | 1/2012 | Seliktar et al. | |
| 2012/0034164 A1 | 2/2012 | Ruoslahti et al. | |
| 2012/0058943 A1 | 3/2012 | Werner et al. | |
| 2012/0100106 A1 | 4/2012 | Panitch et al. | |
| 2012/0227131 A1 | 9/2012 | Abad et al. | |
| 2012/0246748 A1 | 9/2012 | Guo et al. | |
| 2012/0258068 A1 | 10/2012 | Seliktar et al. | |
| 2012/0294925 A1 | 11/2012 | Lynn et al. | |
| 2013/0035307 A1 | 2/2013 | Prestwich et al. | |
| 2013/0045926 A1 | 2/2013 | Devore et al. | |
| 2013/0052155 A1 | 2/2013 | Marcolongo et al. | |
| 2013/0074202 A1 | 3/2013 | Adams et al. | |
| 2013/0101628 A1 | 4/2013 | Webber et al. | |
| 2013/0109808 A1 | 5/2013 | Elisseeff | |
| 2013/0116405 A1 | 5/2013 | Yu et al. | |
| 2013/0152224 A1 | 6/2013 | Abad et al. | |
| 2013/0190246 A1 | 7/2013 | Paderi et al. | |
| 2013/0196896 A1 | 8/2013 | Komatsu et al. | |
| 2013/0323311 A1 | 12/2013 | Paderi et al. | |
| 2013/0333061 A1 | 12/2013 | Wu et al. | |
| 2014/0011978 A1 | 1/2014 | Hubbell et al. | |
| 2014/0028002 A1 | 1/2014 | Li | |
| 2014/0170683 A1 | 6/2014 | Ling et al. | |
| 2014/0288002 A1 | 9/2014 | Panitch et al. | |
| 2014/0288022 A1 | 9/2014 | Elisseeff et al. | |
| 2014/0301972 A1 | 10/2014 | Barritault et al. | |
| 2014/0301983 A1 | 10/2014 | Panitch et al. | |
| 2014/0369975 A1 | 12/2014 | Lee et al. | |
| 2015/0031619 A1 | 1/2015 | Panitch et al. | |
| 2015/0038425 A1 | 2/2015 | Paderi et al. | |
| 2015/0038427 A1 | 2/2015 | Panitch et al. | |
| 2015/0111308 A1 | 4/2015 | Yu et al. | |
| 2016/0065083 A1 | 3/2016 | Mizutani et al. | |
| 2016/0129076 A1 | 5/2016 | Panitch et al. | |
| 2016/0166654 A1 | 6/2016 | Paderi et al. | |
| 2016/0222064 A1 | 8/2016 | Panitch et al. | |
| 2016/0229895 A1 | 8/2016 | Paderi et al. | |
| 2016/0244495 A1 | 8/2016 | Panitch et al. | |
| 2016/0331841 A1 | 11/2016 | Prestwich et al. | |
| 2017/0043023 A1* | 2/2017 | Panitch | A61K 38/1709 |
| 2017/0112941 A1 | 4/2017 | Panitch et al. | |
| 2017/0275345 A1 | 9/2017 | Panitch et al. | |
| 2017/0283458 A1 | 10/2017 | Panitch et al. | |
| 2017/0368192 A1 | 12/2017 | Paderi et al. | |
| 2018/0030091 A1 | 2/2018 | Paderi et al. | |
| 2018/0326077 A1 | 11/2018 | Panitch et al. | |
| 2019/0022175 A1 | 1/2019 | Panitch et al. | |
| 2019/0330276 A1 | 10/2019 | Panitch et al. | |
| 2020/0078469 A1 | 3/2020 | Prestwich et al. | |
| 2021/0188915 A1 | 6/2021 | Panitch et al. | |
| 2021/0290726 A1 | 9/2021 | Paderi et al. | |

FOREIGN PATENT DOCUMENTS

| | | |
|---|---|---|
| EP | 0462194 | 12/1991 |
| EP | 1586652 | 10/2005 |
| EP | 1677807 | 7/2006 |
| EP | 2292773 | 3/2011 |
| EP | 2295582 | 3/2011 |
| JP | 2000-109500 | 4/2000 |

(56) References Cited

FOREIGN PATENT DOCUMENTS

| | | |
|---|---|---|
| JP | 2005185101 | 7/2005 |
| WO | WO-9006767 | 6/1990 |
| WO | WO-1992/012175 | 7/1992 |
| WO | WO-9216555 | 10/1992 |
| WO | WO-1999/027105 | 6/1999 |
| WO | WO-2001/019386 | 3/2001 |
| WO | WO-2004045542 | 6/2004 |
| WO | WO-2005/055800 | 6/2005 |
| WO | WO-2005/061018 | 7/2005 |
| WO | WO-2005/082430 | 9/2005 |
| WO | WO-2005/116066 | 12/2005 |
| WO | WO-2006/047758 | 5/2006 |
| WO | WO-2006/130974 | 12/2006 |
| WO | WO-2007005491 | 1/2007 |
| WO | WO-2007/044026 | 4/2007 |
| WO | WO-2007071448 | 6/2007 |
| WO | WO-2007/138291 | 12/2007 |
| WO | WO-2008/034648 | 3/2008 |
| WO | WO-2008/066816 | 6/2008 |
| WO | WO-2008/070179 | 6/2008 |
| WO | WO-2008/126092 | 10/2008 |
| WO | WO-2008/152639 | 12/2008 |
| WO | WO-2009046530 | 4/2009 |
| WO | WO-2009/120995 | 10/2009 |
| WO | WO-2009120995 | 10/2009 |
| WO | WO-2010/033564 | 3/2010 |
| WO | WO-2010/115156 | 10/2010 |
| WO | WO-2010/122232 | 10/2010 |
| WO | WO-2010/129547 | 11/2010 |
| WO | WO-2010/139953 | 12/2010 |
| WO | WO-2011/057286 | 5/2011 |
| WO | WO-2011/094149 | 8/2011 |
| WO | WO-2011/156445 | 12/2011 |
| WO | WO-2011/163492 | 12/2011 |
| WO | WO-2012/112767 | 8/2012 |
| WO | WO-2012/162534 | 11/2012 |
| WO | WO-2013/110056 | 7/2013 |
| WO | WO-2014/028209 | 2/2014 |
| WO | WO-2014/038866 | 3/2014 |
| WO | WO-2014/040591 | 3/2014 |
| WO | WO-2014/063102 | 4/2014 |
| WO | WO-2014/071132 | 5/2014 |
| WO | WO-2014/099997 | 6/2014 |
| WO | WO-2014/144969 | 9/2014 |
| WO | WO-2015/022326 | 2/2015 |
| WO | WO-2015/078880 | 6/2015 |
| WO | WO-2015/164822 | 10/2015 |
| WO | WO-2015/175565 | 11/2015 |
| WO | WO-2016/061145 | 4/2016 |
| WO | WO-2016/061147 | 4/2016 |
| WO | WO-2016/065083 | 4/2016 |
| WO | WO-2016/168743 | 10/2016 |
| WO | WO-2016161333 | 10/2016 |
| WO | WO-2017/066349 | 4/2017 |
| WO | WO-2017066349 | 4/2017 |
| WO | WO-2019/010484 | 1/2019 |
| WO | WO-2019/010485 | 1/2019 |
| WO | WO-2019/010490 | 1/2019 |

OTHER PUBLICATIONS

Adiguzel et al., "Collagens in the progression and complications of atherosclerosis," Vascular Medicine, 14, 73-89. (2009).
Allaire et al., "Endothelial Cell Injury in Cardiovascular Surgery: The Intimal Hyperplastic Response," National Center for Biotechnology Information, Ann Thorac Surg, 63(2). 582-91, (1997).
Ando, "Opinion Statement of the Effect of Mechanical Stress on Cartilage Tissue Engineering" The Open Bone Journal, 2, 32-37 (2010).
Armstrong et al., "The Role of Matrix Metalloproteinases in Wound Healing," J Am Podiatr Med Assoc, 92(1), 12-18 (2002).
Ashcroft et al.; "Aging alters the inflammatory and endothelial cell adhesion molecule profiles during human cutaneous wound healing," Laboratory Investigation 78(1), 47-58, (1998).
Basser et al., "Mechanical Properties of the Collagen Network in Human Articular Cartilage as Measured by Osmotic Stress Technique," Archives of Biochemistry and Biophysics, 351(2), 207-219 (1998).
Bernhard et al,. "Synthesis and characterization of an aggrecan mimic," Acta Biomaterialia 8(4), 1543-1550, (2012).
Biermaum et al., "Collageneous matrix coatings on titanium implants modified with decorin and chondroitin sulfate: Characterization and influence on osteoblastic cells," Journal of biomedical materials research. Part A. 77. 551-62 (2006).
Broughton et al., "The basic science of wound healing," Plastic and Reconstructive Surgery 117(7S), 12S-34S (2006).
Business Wire "ZymoGenetics Reports New Findings on Anti-thrombotic Activities of CTRP1; Novel Protein Prevents Platelet Thrombosis without Causing Bleeding," www.thefreelibrary.com/ZymoGenetics+Reports+New+Findings+on+Anti-thrombotic+Activities+of+a0105542135, pp. 1-3 (2003).
Carney et al., "The Structure and Function of Cartilage Proteoglycans," Physiological Reviews, 68(3), 858-910 (1988).
Chiang et al., "A Synthetic Peptide Derived from the Sequence of a Type I Collagen Receptor Inhibits Type I Collagen-Mediated Platelet Aggregation," The Journal of Clinical Investigation, 100(8), 2079-2084 (1997).
Chiang et al., "Cloning, Characterization, and Functional Studies of a 47-kDa Platelet Receptor for Type III Collagen," The Journal of Biological Chemistry, 277(38), 34896-34901 (2002).
Chiang et al., "Cloning, Characterization, and Functional Studies of a Nonintegrin Platelet Receptor for Type I Collagen," J. Clin. Invest., vol. 100, No. 3, pp. 514-521.
Chiang et al., "Peptides Derived From Platelet Non-Integrin Collagen-Receptors or Types I and III Collagen Inhibit Collagen-Platelet Interaction," Cardiovascular & Haematological Disorders—Drug Targets, 7(1), 71-75 (2007).
Christner, "Studies on the properties of the inextricable proteoglycans from bovine nasal cartilage," J. Biol. Chem. 258, 14335-14341 (1983).
Chung et al., "Influence of gel properties on neocartilage formation by auricular chondrocytes photoencapsulated in hyaluronic acid networks," Journal of Biomedical Materials Research Part A, 77(3), 518-525 (2006).
Chung et al. "The influence of degradation characteristics of hyaluronic acid hydrogels on in vitro neocartilage formation by mesenchymal stem cells," Biomaterials, 30(26), 4287-4296 (2009).
Chupa et al., "Vascular Cell Responses to Polysaccharide Materials: In Vitro and In Vivo Evaluations," Biomaterials, 21, 2315-2322 (2000).
Cremer, "The cartilage collagens: a review of their structure, organization and role in the pathogenesis of experimental arthritis in animals and in human rheumatic disease," J Mol Med, 76, 275-288, 1998.
Danielson et al., "Targeted Disruption of Decorin Leads to Abnormal Collagen Fibril Morphology and Skin Fragility," The Journal of Cell Biology, 136, 729-743 (1997).
Demling et al., "Small Intestinal Submucosa Wound Matric and Full-thickness Venous Ulcers: Preliminary Results," Wounds Research, 16(1), 18-22 (2004).
Di Mario et al. "The Dark Side of Percutaneous Coronary Interventions," Journal of the American College of Cardiology Interventions, 1(3):277-278 (2008).
Drachman et al., "Inflammation As a Mechanism and Therapeutic Target for In-stent Restenosis," Current Atherosclerosis Reports; 7(1), 44-49 (2005).
Examination Report for Australian Application No. 2015230796 dated Aug. 26, 2016, (3 pages).
Extended European Search Report for EP11798931, dated Dec. 12, 2013.
Extended European Search Report for European Patent Application 18827869.1 dated Mar. 24, 2021. 13 pages.
Falanga, "Wound healing and its impairment in the diabetic foot," Lancet, 366, 1736-1743 (2005).
Farb et al. "Pathology of Acute and Chronic Coronary Stenting in Humans," Circulation, 99, 44-52 (1999).

(56) References Cited

OTHER PUBLICATIONS

FDA, "Guidance for Industry Chronic Cutaneous Ulcer and Burn Wounds Developing Products for Treatment," (Jun. 2006).
Flaumenhaft et al., "Extracellular Matrix Regulation of Growth Factor and Protease Activity," 1991, Current Opinion in Cell Biology, 3, 817-823 (1991).
Fransson et al., "Periodate Oxidation and Alkaline Degradation of Heparin-Related Glycans," Carbohydrate Research, 80, 131-145 (1980).
Fraser et al., "Hyaluronan: its nature, distribution, functions and turnover," Journal of Internal Medicine, 242, 27-33 (1997).
Fulzele et al., "Study of the Biodegradation and in Vivo Biocompatibility of Novel Biomaterials," European Journal of Pharmaceutical Sciences, vol. 20, 2003, pp. 53-61.
Gallant et al., "Cytokine and Growth Factor mRNA Expression Patterns Associated with the Hypercontracted, Hyperpigmented Healing Phenotype of Red Duroc Pigs: A Model of Abnormal Human Scar Development?" J Cutan Med Surg, 9(4), 165-177 (2005).
Gallant et al., "Molecular, histologic, and gross phenotype of skin wound healing in red Duroc pigs reveals an abnormal healing phenotype of hypercontracted, hyperpigmented scarring," Wound Rep Reg, 12, 305-319 (2004).
Geng et al., "SLRP interaction can protect collagen fibrils from cleavage by collagenases," Matrix Biology, 25, 484-491 (2006).
Gercken et al., "Results of the Jostent Coronary Stent Graft Implantation in Various Clinical Settings: Procedural and Follow-Up Results," Catheterization and Cardiovascular Interventions 56:353-360 (2002).
Gerwin, "Intraarticular drug delivery in osteoarthritis," Advanced Drug Delivery Reviews, 58, 226-242 (2006).
Ghosh et al., "The Effects of Intraarticular Administration of Hyaluronan in a Model of Early Osteoarthritis in Sheep I. Gait Analysis and Radiological and Morphological Studies," Seminarsin Arthritis and Rheumatism, 22(6), 18-30 (1993).
Goldoni et al., "Biologically active decorin is a monomer in solution," J. Bio. Chem. 279(8), 6606-6612 (2004).
Grassl et al., "Fibrin as an Alternative Biopolymer to Type-1 Collagen for the Fabrication of a Media Equivalent," Journal of Biomedical Materials Research, 60(4), 607-612, (2002).
Griese et al., "Isolation and Transplantation of Autologous Circulating Endothelial Cells Into Denuded Vessels and Prosthetic Grafts: Implications for Cell-Based Vascular Therapy," Circulation, 2003, 108:2710-2715.
Griffey et al., "Particulate Dermal Matrix as an Injectable Soft Tissue Replacement Material," J. Biomed. Mater. Res., 58, 10-15 (2001).
Gutman et al., "Liposomal alendronate for the treatment of restenosis," Journal of Controlled Release, 161, 619-627 (2012).
Hantgan et al., "Platelets Interact With Fibrin Only After Activation," Blood, vol. 65, No. 6 (Jun. 1985): pp. 1299-1311.
Helms et al., "High affinity peptide based collagen targeting using synthetic phage mimics: from phage display to dendrimer display," J. Am. Chem. Soc. 131, 11683-11685 (2009).
Hemmer et al., "Minimal peptide length requirements for cd4+ t cell clones—implications for molecular mimicry and t cell survival," Int. Immunol., 12(3) 375-383 (2000).
Hempel et al., "Artificial extracellular matrices composed of collagen I and sulfated hyaluronan with adsorbed transforming growth factor β1 promote collagen synthesis of human mesenchymal stromal cells," Acta Biomaterialia 2011, vol. 8, No. 2, DD. 659-666, XP028123827.
Henn et al., "CD40 ligand on activated platelets triggers an inflammatory reaction of endothelial cells," Nature, 391,591-594 (1998).
Henrotin et al., "Intra-articular use of a medical device composed of hyaluronic acid and chondroitin sulfate (Structovial CS): effects on clinical, ultrasonographic and biological parameters," BMC Research Notes, 5(407), 1-7 (2012).
Hermanson, "Zero-Length Cross-Linkers," Academic Press, 169-186 (1996).
Hintze et al., "Sulfated hyaluronan and chondroitin sulfate derivatives interact differently with human transforming growth factor-β (TGF-β1)," Acta Biomaterialia 2012, vol. 8, No. 6, pp. 2144-2152, XP028480436.
Hollander et al., "Increased Damage to Type II Collagen in Osteoarthritic Articular Cartilage Detected by a New Immunoassay." J. Clin. Invest., 93, 1722-1732 (1994).
Huang et al., "Aggrecanase and Aggrecan Degradation in Osteoarthritis: a Review," The Journal of International Medical Research, 36, 1149-1160 (2008).
Huizinga et al., "Crystal structure of the A3 domain of human von Willebrand factor: implications for collagen binding," Structure 1997, vol. 5, No. 9, pp. 1147-1156.
Hunt et al., "Respiratory Gas Tensions and pH in Healing Wounds," American Journal of Surgery, 114, 302-307, (1967).
International Search Report and Written Opinion for Application No. PCT/US2010/033543 dated Oct. 8, 2010.
International Preliminary Examination Report and Written Opinion for PCT/US2012/039404 dated Nov. 26, 2013.
International Search Report and Written Opinion Application No. PCT/US2009/038624, dated Dec. 7, 2009.
International Search Report and Written Opinion for PCT/US2011/041654, dated Nov. 7, 2011.
International Search Report Opinion for PCT/US2014/029596, dated Jul. 28, 2014.
Written Opinion for International Application No. PCT/US2012/039404, dated Apr. 17, 2013.
International Preliminary Report on Patentability for International Application No. PCT/US2010/033543, dated Nov. 9, 2011. (9 pages).
International Search Report issued in International Application No. PCT/US2012/039404 dated Apr. 29, 2013.
International Search Report and Written Opinion for International Application No. PCT/US2018/041280 dated Nov. 15, 2018. (12 pages).
Järveläinen et al., "A role for decorin in cutaneous wound healing and angiogenesis" Wound Rep Reg, 14, 443-452 (2006).
Järvinen et al., "Target-seeking antifibrotic compound enhances wound healing and suppresses scar formation in mice" PNAS, 107(50), 21671-21676 (2010).
Jiang et al., "Targeting Heparin to Collagen within Extracellular Matrix Significantly Reduces Thrombogenicity and Improves Endothelialization of Decellularized Tissues," Biomacromolecules, 2016, vol. 17, No. 12, pp. 3940-3948, XP055592025.
Julienne et al., "Topical Treatment with a New Matrix Therapy Agent (RGTA, CACICOL-20) Improves Epithelial Wound Healing After Penetrating Keratoplasty," Acta Ophthalmological, 2014, 92(s253).
Kadler et al., "Collagen fibril formation," Biochem. J., 1996, 316, pp. 1-11.
Kalamajski et al., "The Decorin Sequence SYIRIADTNIT Binds Collagen Type 1," Journal of Biological Chemistry, 282(22), 16062-16067 (2007).
Kalamajski, "The role of small leucine-rich proteoglycans in collagen fibrillogenesis," Matrix Biology, 29(4), 248-253 (2010).
Kapoor, "Role of proinflammatory cytokines in the pathophysiology of osteoarthritis," Nat. Rev. Rheumatol, 7, 33-42 (2011).
Khorramizadeh et al., "Aging differentially modulates the expression of collagen and collagenase in dermal fibroblasts," Molecular and Cellular Biochemistry, 194, 99-108 (1999).
Kiani et al., "Review: Structure and function of aggrecan," Cell Research 12(1), 19-32 (2002).
Kipshidze et al., "Role of the Endothelium in Modulating Neointimal Formation," Journal of the American College of Cardiology, 44(4), 733-739 (2004).
Kirker et al., "Glycosaminoglycan Hydrogel Films as Biointeractive Dressings for Wound Healing," Biomaterials, 23(17):3661-3671.
Kitov, "On the nature of the multivalency effect: a thermodynamic model," J. Am. Chem. Soc., 125, 16271-16284 (2003).
Klatt, "A Critical Role for Collagen II in Cartilage Matrix Degradation: Collagen II Induces Pro-Inflammatory Cytokines and MMPs in Primary Human Chondrocytes" J. Orthop Res, (27) 65-70 (2009).

(56) References Cited

OTHER PUBLICATIONS

Knudson, "Cartilage Proteoglycans," Cell & Developmental Biology, 12, 69-78 (2001).
Koehler et al., "Sulfated Hyaluronan Derivatives Modulate TGF-β1:Receptor Complex Formation: Possible Consequences for TGF-β1 Signaling," Scientific Reports 2017, vol. 7, No. 1, XP055780190. Retrieved from the Internet: www. nature .com/articles/s41598-017-01264-8.
Kraus et al., "The OARSI Histopathology Initiative—Recommendations for Histological Assessments of Osteoarthritis in the Guinea Pig," Osteoarthritis Cartilage, 18(Suppl. 3), S35-S52 (2010).
Kraut et al., "Challenges in Enzyme Mechanism and Energetics," Annu. Rev. Biochem., 72, 2003, pp. 517-571.
Larroque et al., "New matrix therapy in chronic corneal ulcers resistant to conventional therapies," Acta Ophthalmological, 2013, 91(s252):0.
Lasser et al., "C1qTNF-related protein-1 (CTRP-1): a vascular wall protein that inhibits collagen-induced platelet aggregation by blocking VWF binding to collagen," Blood, 2006, 107, 423-430.
Lazic et al., "Bioengineered Skin Constructs and Their Use in Wound Healing," Plastic and Reconstructive Surgery, 2010, 127(1S), 75S-90S.
Le Tourneau et al., "Dose Escalation Methods in Phase I Cancer Clinical Trials," J Natl Cancer Inst 2009, 101:708-720.
Lee et al., "Dark Quenched Matrix Metalloproteinase Fluorogenic Probe for Imaging Osteoarthritis Development in Vivo," Bioconjugate Chemistry, 19(9), 1743-1747 (2008).
Lee et al. "Enhanced chondrogenesis of mesenchymal stem cells in collagen mimetic peptide-mediated microenvironment," Tissue Engineering Part A, 14(11) 1843-1851 (2008).
Lee et al., "Effect of glucosamine or chondroitin sulfate on the osteoarthritis progression: a meta-analysis," Rheumatol Int., 30, 357-363 (2010).
Lee et al., "Polymeric Nanoparticle-Based Activatable Near-Infrared Nanosensor for Protease Determination In Vivo," Nano Lett., 9(12), 4412-4416 (2009).
Lee et al., "Injectable gel with synthetic collagen-binding peptide for enhanced osteogenesis in vitro and in vivo," Biochemical and Biophysical Research Communications 357 (2007) 68-74.
Lemon et al., "Immunoprecipitation and Virus Neutralization Assays Demonstrate Qualitative Differences between Protective Antibody Responses to Inactivated Hepatitis A Vaccine and Passive Immunization with Immune Globulin," The Journal of Infectious Diseases 1997; 176:9-19.
Libby et al. "A Cascade Model for Restenosis—A Special Case of Atherosclerosis Progression," Circulation, 86(6), III-47-III-52 (1992).
Lynn et al., "Design of a Multiphase Osteochondral Scaffold. I. Control of Chemical Composition," J Biomed Mater Res A, 2010, 92(3):1057-1065.
Madry et al., "Biological aspects of early osteoarthritis," Knee Surg Sports Traumator Arthrosc, 20, 407-422 (2012).
Madsen et al., "Aggrecanase- and matrix metalloproteinase-mediated aggrecan degradation is associated with different molecular characteristics of aggrecan and separated in time ex vivo," Biomarkers, 2009; 15(3): 266-276.
Mammen et al., "Polyvalent interactions in Biological Systems: Implications for Design and Use of Multivalent Ligands and Inhibitors," Angew. Chem. Int. Ed., 37, 2754-2794 (1998).
Maroudas, "Balance between Swelling pressure and collagen tension in normal and degenerate cartilage," Nature, 260, 808-809 (1976).
Martil-Pelletier, "Review: Future therapeutics for osteoarthritis," Bone, 51, 297-311, 2012.
Martin, "Wound Healing-Aiming for Perfect Skin Regeneration," Science, vol. 276, 1997, pp. 75-81.
Masuko et al., "Anti-inflammatory effects of hyaluronan in arthritis therapy: Not just for viscosity," International Journal of General Medicine, 2, 77-81 (2009).
Moustafa et al., "A new autologous keratinocyte dressing treatment for non-healing diabetic neuropathic foot ulcers," Diabet. Med. 21, 786-789 (2004).
Mummert et al., "Development of a Peptide Inhibitor of Hyaluronan-mediated Leukocyte Trafficking," J. Exp. Med., 192(6), 769-779 (2000).
Mummert, "Immunological Roles of Hyaluronan," Immunologic Research, 31(3), 189-205 (2005).
Nagase et al., "Review: Aggrecanases and cartilage matrix degradation," Arthritis Research & Therapy, 5(2) 94-103 (2003).
Nia et al., "High-Bandwidth AFM-Based Rheology Reveals that Cartilage is Most Sensitive to High Loading Rates at Early Stages of Impairment," Biophysical Journal, 104, 1529-1537 (2013).
Nili et al., "Decorin inhibition of PDGF-stimulated vascular smooth muscle cell function: potential mechanism for inhibition of intimal hyperplasia after balloon angioplasty," The American Journal of Pathology, 163(3), 869-878 (2003).
O'Brien, et al., "The Effect of Pore Size on Cell Adhesion in Collagen-GAG Scaffolds," Biomaterials, 2005, 26(4): 433-441.
Ogden, "Clinical responses to new and reprocessed hemodialyzers," Guide to Reprocessing of Hemodialyzers, 87-97 (1986).
Orbusneich, "About the Combo Dual Therapy Stent".
Oyama et al., "Isolation of lung tumor specific peptides from a random peptide library: generation of diagnostic and cell-targeting reagents," Cancer Letters 202 (2003) 219-230.
Paderi et al., "Collagen-Binding Peptidoglycans: A Biomimetic Approach to Modulate Collagen Fibrillogenesis for Tissue Engineering Applications," Tissue Engineering Part A, 15(10), 2991-2999 (2009).
Paderi et al., "Design of a Synthetic Collagen-Binding Peptidoglycan that Modulates Collagen Fibrillogenesis," Biomacromolecules, 9, 2562-2566 (2008).
Paderi, "Design of collagen binding proteoglycan mimics," Thesis (Aug. 2008).
Paderi et al., "The Inhibition of Platelet Adhesion and Activation on Collagen During Balloon Angioplasty by Collagen-Binding Peptidoglycans," Biomaterials, 32, 2516-2523 (2011).
Penc et al., "Dermatan Sulfate Released after Injury Is a Potent Promoter of Fibroblast Growth Factor-2 Function," The Journal of Biological Chemistry, 273(43), 28116-28121 (1998).
Pentikainen et al., "The proteoglycan decorin links low density lipoproteins with collagen type I," J. Bio. Chem. 272(12), 7633-7638 (1997).
Pieper et al., "Development of Tailor-Made Collagen-Giycosaminoglycan Matrices: EDC/NHS Crosslinking, and Ultrastructural Aspects," Biomaterials, 21, 581-593 (2000).
Pierce Biotechnology Catalog (2005/2006).
Pignatelli et al., "Hydrogen peroxide is involved in collagen induced platelet activation," Blood, 91(2) 484-490 (1998).
Pizzo et al., "Extracellular Matrix (ECM) Microstructural Composition Regulates Local Cell-ECM Biomechanics and Fundamental Fibroblast Behavior: A Multidimensional Perspective," Journal Appl. Physiol, 98, 1909-1921 (2005).
Place et al., (2014), "Aggrecan-mimetic, glycosaminoglycan-containing nanoparticles for growth factor stabilization and delivery," Biomacromolecules, 15(2):680-689.
Place et al., (2014), "Synthesis and characterization of proteoglycan-mimetic graft copolymers with tunable glycosaminoglycan density," Biomacromolecules, 15(10):3772-3780.
Pratta et al., "Aggrecan Protects Cartilage Collagen from Proteolytic Cleavage," J. Biol. Chem., 278(46), 45539-45545 (2003).
Pratta et al., "Glycobiology and Extracellular Matrices: Aggrecan Protects Cartilage Collagens from Proteolytic Cleavage," J. Biol. Chem., 278(46), 45539-45545 (2003).
Puig et al., "A new decorin-like tetrapeptide for optimal organization of collagen fibres," International Journal of Cosmetic Science, 30, 97-104 (2008).
Radek et al., "FGF-10 and specific structural elements of dermatan sulfate size and sulfation promote maximal keratinocyte migration and cellular proliferation," Wound Rep Reg, 17, 118-126 (2009).
Ratcliffe, "Tissue engineering of vascular grafts," Matrix Biology, 19, 353-357 (2000).

(56) References Cited

OTHER PUBLICATIONS

Reed et al., "The role of decorin in collagen fibrillogenesis and skin homeostasis," Glycoconjugate Journal, 19, 249-255 (2003).
Roeder et al., "Tensile Mechanical Properties of Three-Dimensional Type I Collagen Extracellular Matrices With Varied Microstructure," Transactions of the ASME vol. 124, 2002, pp. 214-222.
Romijn et al., "Mapping the Collagen-Binding Site in the Von Willebrand Factor-A3 Domain," The Journal of Biological Chemistry, 278(17), 15035-15039 (2003).
Roseborough et al., "Prevention and treatment of excessive dermal scarring," J. Natl. Med. Assoc., 96, 108-116 (2004).
Rosenblum et al., "Diminished Benefits of Drug-Eluting Stents versus Bare Metal Stents in Patients with Severe Renal Insufficiency," Nephron Clinical Practice, 113, c198-c202, (2009).
Rossi et al., "Decontamination of surfaces by low pressure plasma discharges," Plasma Process. Polym. 3, 431-442 (2006).
Roth et al., "Localization of binding sites within human von willebrand factor for monomeric type III collagen," Biochemistry 25, 8357-8361 (1986).
Roy-Chaudhury et al., "Hemodialysis Vascular Access Dysfunction: A Cellular and Molecular Viewpoint," J AM Sco Nephrol, 17(4), 1112-1127 (2006).
Rudbach et al., "Physical Aspects of Reversible Inactivation of Endotoxin," Annals New York Academy of Sciences, (1966) 133, pp. 629-643.
Ruotsalainen et al., "Glycosylation catalyzed by lysyl hydroxylase 3 is essential for basement membranes," Journal of Cell Science (2006), 119, pp. 625-635.
Rutjes et al., "Viscosupplementation for Osteoarthritis of the Knee: A Systematic Review and Meta-analysis," Ann Intern Med., (157), 180-191 (2012).
Santa Cruz Biotechnology listing for phosphate buffered saline (http://www.scbt.com/datasheet-362182.html, downloaded Feb. 10, 2014) CN-101906163.
Saxena et al., "Enhancing the survival of tunneled haemodialysis catheters using an antibiotic lock in the elderly: a randomized, double blind clinical trial," Nephrology, 11, 299-305 (2006).
Schilling et al., "Wound Healing: A Comparative Study of the Histochemical Changes in Granulation Tissue Contained in Stainless Steel Wire Mesh and Polyvinyl Sponge Cylinders," Surgery, 46(4), 702-710, 1959.
Schmitz et al., "Hyaluronan oligosaccharide treatment of chondrocytes stimulates expression of both HAS-2 and MMP-3, but by different signaling pathways," Osteoarthritis Cartilage, 18(3), 447-454 (2010).
Schonherr et al., "Decorin Core Protein Fragment LEU 155-Val260 Interacts with TGF-Beta But Does Not Compete for Decorin Binding to Type I Collagen," Arch. Biochem. Biophys., 355(2), 241-248 (1998). Abstract Only.
Schultz et al., "Interactions between extracellular matrix and growth factors in wound healing," Wound Rep Reg (2009) 17, 153-162.
Schuppan et al., "Matrix as a modulator of hepatic fibrogenesis," Seminars in Liver Disease. 21(3):351-372 (2001).
Scott et al., "Molecular and Cellular Aspects of Fibrosis Following Thermal Injury," Thermal Injuries, 16(2), 271-287 (2000).
Scott et al., "Chemical characterization and quantification of proteoglycans in human post-burn hypertrophic and mature scars," Clinical Science, 90(5), 417-425 (1996).
Scott et al., "Decorin mimic inhibits vascular smooth muscle proliferation and migration," PLOS One, 8(11):e82456. (2013).
Scott et al., "Dermatan sulphate-rich proteoglycan associates with rat tail-tendon collagen at the d band in the gap region," Biochem. J., 197(1), 213-216 (1981).
Scott et al., "Proteoglycan-fibrillar collagen interactions," Biochem. J, 252, 313-323 (1988).
Sharma et al., "Biomimetic Aggrecan Reduces Cartilage Extracellular Matrix From Degradation and Lowers Catabolic Activity in Ex Vivo and In Vivo Modelsa," Macromolecular Bioscience, DOI 10.1002, 1-10 (2013).
Shin et al., "A novel collagen-binding peptide promotes osteogenic differentiation via Ca2+/calmodulin-dependent protein kinase II/ERK/ AP-1 signaling pathway in human bone marrow-derived mesenchymal stem cells," Cellular Signalling, 20, (2008) 613-624.
Singer et al., "Cutaneous Wound Healing," The New England Journal of Medicine, 341(10), 738-746 (1999).
Sini et al., "Role of decorin on in vitro fibrillogenesis of type 1 collagen," Glycoconj. J., 14, 871-874 (1997).
Smith, Jr. et al., "Effect of Intraarticular Hyaluronan Injection in Experimental Canine Osteoarthritis," Arthritis & Rheumatism, 41(6), 976-985 (1998).
Stuart et al., "Collagen-Binding peptidoglycans inhibit MMP mediated collagen degradation and reduce dermal scarring," PLOS One, 6(7), e22139, 2011.
Suki et al., "Biomechanics of the lung parenchyma: critical roles of collagen and mechanical forces," J Appl Physiol 98: 1892-1899, 2005.
Svensson et al., "Decorin-binding Sites for Collagen Type I Are Mainly Located in Leucine-rich Repeats 4-5," vol. 270, No. 35, pp. 20712-20716, 1995.
Taylor et al., "Structural and Sequence Motifs in Dermatan Sulfate for Promoting Fibroblast Growth Factor-2 (FGF-2) and FGF-7 Activity," The Journal of Biological Chemistry, 280(7), 5300-5306 (2005).
Tenni et al., "Interaction of Decorin with CNBr Peptides from Collagens I and II Evidence for Multiple Binding Sites and Essential Lysyl Residues in Collagen," Eur. J. Biochem., 269,1428-1437 (2002).
The USRDS Coordinating, "Incidence, prevalence, patient characteristics, and treatment modality," Center United States Renal Data System, 2, 215-228 (2013).
Tollefsen, "Vascular Dermatan Sulfate and Heparin Cofactor II," Progress in Molecular Biology and Translational Science, 93, 351-372 (2010).
Trengove et al., "Analysis of the acute and chronic wound environments: the role of proteases and their inhibitors," Wound Rep Reg, 7(6), 442-452 (1999).
Trowbridge et al., "Dermatan Sulfate Binds and Potentiates Activity of Keratinocyte Growth Factor (FGF-7)," The Journal of Biological Chemistry, 277(45), 42815-42820 (2002).
Trowbridge et al., "Dermatan sulfate: new functions from an old glycosaminoglycan," Glycobiology, vol. 12, No. 9, pp. 117R-125R, 2002.
Umlauf et al., "Cartilage biology, pathology, and repair," Cell. Mol. Life Sci., 67, 4197-4211 (2010).
Uniprot/Trembl Q7Z4J1, "Nonintegrin Platelet Receptor for Type I Collagen," Last Modified Feb. 10, 2009, Available on the Internet <URL: http://www.uniprot.org/uniprot/Q7Z4J1 & format=html>.
Uniprotkb, "Decorin Precursor-Bas Taurus (Bovine)," Last Modified Sep. 1, 2009, Available on the Internet <URL:http://www.uniprot.org/uniprot/P21793>.
Van Der Smissen et al., "Artificial extracellular matrix composed of collagen I and highly sulfated hyaluronan interferes with TGFb1 signaling and prevents TGFb1-induced myofibroblast differentiation," Acta Biomaterialia 2013, vol. 9, pp. 7775-7786, XP055780186. Retrieved from the Internet: josorge.com/publications/Citations/Hepatol/014.pdf.
Van Neck et al., "Heparan Sulfate Proteoglycan Mimetics Promote Tissue Regeneration: An Overview," Chapter 4 In J Davies (Ed.), Tissue Regeneration—From Basic Biology to Clinical Application, 69-92, InTech—Open Access Publisher, doi: 10.5772/25622, (2012).
Velander et al., "Impaired wound healing in an acute diabetic pig model and the effects of local hyperglycemia," Wound Rep Reg, 16, 288-293 (1999).
Vogel et al., "Specific inhibition of type I and type II collagen fibrillogenesis by the small proteoglycan of tendon," Biochem. J. (1984) 223, 587-597.
Wang et al., "Deep dermal fibroblasts contribute to hypertrophic scarring," Laboratory Investigation, 88, 1278-1290 (2008).
Wang et al., "Venous stenosis in a pig arteriovenous fistula model-anatomy, mechanisms and cellular phenotypes," Nephrol Dial Transplace, 23:525-533 (2008).
Wang et al., "Platelet, Not Endothelial, P-Selection is Required for Neointimal Formation After Vascular Injury," Arterioscler Thromb. Vase. Biol., 25, 2005, pp. 1584-1589.

(56) References Cited

OTHER PUBLICATIONS

Widgerow et al., "Multimodality Scar Management Program," Aesth Plast Surg (2009) 33:533-543.

Williams et al., "Collagen Fibril Formation," J. Biol. Chem., 253(18), 1978, pp. 6578-6585.

Winterton et al., "Heparin Interaction with Protein-Adsorbed Surfaces," J. Colloid Interface Sci., vol. 111, 314-342 (1986).

Wysocki et al., "Wound Fluid from Chronic Leg Ulcers Contains Elevated Levels of Metalloproteinases MMP-2 and MMP-9," The Society for Investigative Dematology, Inc., 101(1), 64-68 (1993).

Yampolsky et al., "The Exchangeability of Amino Acids in Proteins," Genetics (2005) 170, 1459-1472.

Zhang et al., "Preservation of the structure of enzymatically-degraded bovine vitreous using synthetic proteoglycan mimics," Invest Ophthalmol Vis Sci, 55:8153-8162 (2014).

Zhu et al., "Review of the female Duroc/Yorkshire pig model of human fibroproliferative scarring," Wound Rep. Reg., 15, S32-S39 (2007).

Zhu et al., "The female, red Duroc pig as an animal model of hypertrophic scarring and the potential role of the cones of skin," Burns, 29, 649-664 (2003).

Zhu et al., "Further similarities between cutaneous scarring in the female, red Duroc pig and human hypertrophic scarring," Burns, 30, 518-530 (2004).

Zustiak et al., "Influence of Cell-Adhesive Peptide Ligands on Poly(ethylene glycol) Hydrogel Physical, Mechanical and Transport Properties," Acta Biomater., 2010, 6(9): 3404-3414.

Elder, A. N. et al. Polymer Preprints (2010), 51(2); pp. 592-593.

International Search Report and Written Opinion for International Application No. PCT/US2016/027953 dated Jul. 12, 2016. 14 pages.

Yang, B. et al. Anal. Biochem. (1995), 228; pp. 299-306.

\* cited by examiner

Addition of spacer to vWF-2x

SEQUENCE LISTING

<160> NUMBER OF SEQ ID NOS: 132

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Ser Gly Lys Arg Arg Gly Ser Gly
1               5

```
<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Arg Arg Lys Lys Ile Gln Gly Arg Ser Lys Arg
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Arg Gly Gly Arg Lys Trp Gly Ser Phe Glu Gly
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Ser Gly Ser Gly Ser Arg Arg
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gln Leu Tyr Lys Ser Ile Leu Tyr
1               5

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gln Leu Tyr Lys Ser Ile Leu Tyr Gly Ser Gly Ser Gly Ser Arg
1               5                   10                  15

Arg

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 7

Pro Ala Pro Ala Pro Arg Arg
1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Arg Glu Pro Ser Phe Ser Ala Leu Ser
1               5                   10

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Arg Ala Asn Ala Ala Leu Lys Ala Gly Glu Leu Tyr Lys Ser Ile
1               5                   10                  15

Leu Tyr

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Glu Leu Tyr Lys Ser Ile Leu Tyr
1               5

<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Arg Ala Asn Ala Ala Leu Lys Ala Gly Glu Leu Tyr Lys Cys Ile
1               5                   10                  15

Leu Tyr

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Glu Leu Tyr Lys Cys Ile Leu Tyr
1               5
```

```
<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Arg Ala Asn Ala Ala Leu Lys Ala Gly Gln Leu Tyr Lys Ser Ile
1               5                   10                  15

Leu Tyr

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Arg Ala Asn Ala Ala Leu Lys Ala Gly Gln Leu Tyr Lys Cys Ile
1               5                   10                  15

Leu Tyr

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gln Leu Tyr Lys Cys Ile Leu Tyr
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Leu Asp Gly Asn Glu Ile Lys Arg
1               5

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala His Glu Glu Ile Ser Thr Thr Asn Glu Gly Val Met
1               5                   10

<210> SEQ ID NO 18
<211> LENGTH: 28
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 18

Asn Gly Val Phe Lys Tyr Arg Pro Arg Tyr Phe Leu Tyr Lys His Ala
1               5                   10                  15

Tyr Phe Tyr Pro Pro Leu Lys Arg Phe Pro Val Gln
            20                  25

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Cys Gln Asp Ser Glu Thr Arg Thr Phe Tyr
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Lys Lys Thr Leu Arg Thr
1               5

<210> SEQ ID NO 21
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Leu Arg Ser Lys Ser Lys Lys Phe Arg Arg Pro Asp Ile Gln Tyr
1               5                   10                  15

Pro Asp Ala Thr Asp Glu Asp Ile Thr Ser His Met
            20                  25

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Gln Asn Pro Val Gln Pro
1               5

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 23

Ser Tyr Ile Arg Ile Ala Asp Thr Asn Ile Thr
1               5                   10

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Glu Leu Asn Leu Val Tyr Thr
1               5

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Ser Ile Thr
1

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Ser Ile Thr Thr Ile Asp Val Pro Trp Asn Val
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Val Met His Gly Leu His Leu Gly Asp Asp Glu
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Cys Arg Val Met His Gly Leu His Leu Gly Asp Asp Glu Cys
1               5                   10

<210> SEQ ID NO 29

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Trp Arg Glu Pro Ser Phe Cys Ala Leu Ser
1               5                   10

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Alanine
<220> FEATURE:
<221> NAME/KEY: MOD_RES
<222> LOCATION: (16)..(16)
<223> OTHER INFORMATION: Biphenylalanine

<400> SEQUENCE: 30

Ala Trp His Cys Thr Thr Lys Phe Pro His His Tyr Cys Leu Tyr Xaa
1               5                   10                  15

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Alanine
<220> FEATURE:
<221> NAME/KEY: MOD_RES
<222> LOCATION: (17)..(17)
<223> OTHER INFORMATION: Biphenylalanine

<400> SEQUENCE: 31

Ala His Lys Cys Pro Trp His Leu Tyr Thr Thr His Tyr Cys Phe Thr
1               5                   10                  15

Xaa

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Alanine

<400> SEQUENCE: 32

Ala His Lys Cys Pro Trp His Leu Tyr Thr His Tyr Cys Phe Thr
1               5                   10                  15

<210> SEQ ID NO 33
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4-Hydroxyproline

<400> SEQUENCE: 33

Gly Arg Pro Gly Glu Arg
1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4-Hydroxyproline

<400> SEQUENCE: 34

Gly Met Pro Gly Glu Arg
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4-Hydroxyproline

<400> SEQUENCE: 35

Gly Leu Pro Gly Glu Asn
1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4-Hydroxyproline

<400> SEQUENCE: 36

Gly Leu Pro Gly Glu Arg
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37
```

```
Gly Leu Lys Gly Glu Asn
1               5
```

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4-Hydroxyproline
<220> FEATURE:
<221> NAME/KEY: MOD_RES
<222> LOCATION: (12)..(12)
<223> OTHER INFORMATION: 4-Hydroxyproline

<400> SEQUENCE: 38

```
Gly Phe Pro Gly Glu Arg Gly Val Glu Gly Pro Pro Gly Pro Ala
1               5                   10                  15
```

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
His Val Trp Met Gln Ala Pro Gly Gly Gly Lys
1               5                   10
```

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Trp Tyr Arg Gly Arg Leu
1               5
```

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
Trp Thr Cys Ser Gly Asp Glu Tyr Thr Trp His Cys
1               5                   10
```

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

```
Trp Thr Cys Val Gly Asp His Lys Thr Trp Lys Cys
1               5                   10
```

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

```
Gln Trp His Cys Thr Thr Arg Phe Pro His His Tyr Cys Leu Tyr Gly
1               5                   10                  15
```

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

```
Ser Thr Trp Thr Trp Asn Gly Ser Ala Trp Thr Trp Asn Glu Gly Gly
1               5                   10                  15

Lys
```

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
Ser Thr Trp Thr Trp Asn Gly Thr Asn Trp Thr Arg Asn Asp Gly Gly
1               5                   10                  15

Lys
```

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

```
Cys Val Trp Leu Trp Glu Gln Cys
1               5
```

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

```
Cys Val Trp Leu Trp Glu Asn Cys
1               5
```

<210> SEQ ID NO 48

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Cys Met Thr Ser Pro Trp Arg Cys
1               5

<210> SEQ ID NO 49
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Cys Pro Gly Arg Val Met His Gly Leu His Leu Gly Asp Asp Glu Gly
1               5                   10                  15

Pro Cys

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Lys Leu Trp Leu Leu Pro Lys
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Leu Ser Glu Leu Arg Leu His Glu Asn
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Thr Glu Leu His Leu Asp Asn Asn
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 53

Leu Ser Glu Leu Arg Leu His Asn Asn
1               5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Leu Ser Glu Leu Arg Leu His Ala Asn
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Arg Glu Leu His Leu Asn Asn Asn
1               5

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Glu Asp Asp Gly Leu His Leu Gly His Met Val Arg
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Val Met His Gly Leu His Leu Gly Asn Asn Gln
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Asn Asn Gly Leu His Leu Gly His Met Val Arg
1               5                   10

<210> SEQ ID NO 59
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 59

Gly Gln Leu Tyr Lys Ser Ile Leu Tyr Gly Ser Gly
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Ser Gly Gln Leu Tyr Lys Ser Ile Leu Tyr
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Ser Gly Gly Gln Leu Tyr Lys Ser Ile Leu Tyr
1               5                   10

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Lys Gln Leu Asn Leu Val Tyr Thr
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Cys Val Trp Leu Trp Gln Gln Cys
1               5

<210> SEQ ID NO 64
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly His Arg Pro Leu Asp Lys Lys Arg Glu Glu Ala Pro Ser Leu Arg
1               5                   10                  15
```

```
Pro Ala Pro Pro Pro Ile Ser Gly Gly Gly Tyr Arg
            20                  25
```

<210> SEQ ID NO 65
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

```
Gly His Arg Pro Leu Asn Lys Lys Arg Gln Gln Ala Pro Ser Leu Arg
1               5                   10                  15

Pro Ala Pro Pro Pro Ile Ser Gly Gly Gly Tyr Arg
            20                  25
```

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

```
Ser Ile Leu Tyr
1
```

<210> SEQ ID NO 67
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

```
Gly Ser Gly Ser
1
```

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

```
Arg Gly Ser Gly
1
```

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

```
Arg Gly Ser Gly Ser
1               5
```

<210> SEQ ID NO 70

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Arg Arg Gly Ser
1

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Arg Arg Gly Ser Gly
1               5

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Arg Arg Gly Ser Gly Ser
1               5

<210> SEQ ID NO 73
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Lys Gly Ser Gly
1

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Lys Lys Gly Ser Gly
1               5

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75
```

```
Lys Lys Lys Gly Ser Gly
1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: This region may encompass 0-5 residues

<400> SEQUENCE: 76

Lys Lys Lys Lys Lys Gly Ser Gly
1               5

<210> SEQ ID NO 77
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Arg Arg Ala Asn Ala Ala Leu Lys Ala Gly Glu Leu Tyr Lys Ser Ile
1               5                   10                  15

Leu Tyr Gly Ser Gly
            20

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid

<400> SEQUENCE: 78

Xaa Gln Leu Tyr Lys Ser Ile Leu Tyr
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid

<400> SEQUENCE: 79

Gly Xaa Leu Tyr Lys Ser Ile Leu Tyr
1               5

<210> SEQ ID NO 80
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 80

Gly Gln Xaa Tyr Lys Ser Ile Leu Tyr
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 81

Gly Gln Leu Xaa Lys Ser Ile Leu Tyr
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 82

Gly Gln Leu Tyr Xaa Ser Ile Leu Tyr
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid

<400> SEQUENCE: 83

Gly Gln Leu Tyr Lys Xaa Ile Leu Tyr
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid
```

<400> SEQUENCE: 84

Gly Gln Leu Tyr Lys Ser Xaa Leu Tyr
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid

<400> SEQUENCE: 85

Gly Gln Leu Tyr Lys Ser Ile Xaa Tyr
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid

<400> SEQUENCE: 86

Gly Gln Leu Tyr Lys Ser Ile Leu Xaa
1               5

<210> SEQ ID NO 87
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Leu Lys Ala Gly Gln Leu Tyr Lys Ser Ile Leu Tyr His His Leu His
1               5                   10                  15

Ser Gly Ser Gly Ser Gly Ser Arg Arg
            20                  25

<210> SEQ ID NO 88
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Lys Ala Gly Gln Leu Tyr Lys Ser Ile Leu Tyr His His Leu His Ser
1               5                   10                  15

Tyr Gly Ser Gly Ser Gly Ser Arg Arg
            20                  25

<210> SEQ ID NO 89
<211> LENGTH: 28

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Gln Leu Tyr Lys Ser Ile Leu Tyr His Leu His Ser Tyr Gln
1               5                   10                  15

Asn Ser Lys Pro Gly Ser Gly Ser Gly Ser Arg Arg
            20                  25

<210> SEQ ID NO 90
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Gln Leu Tyr Lys Ser Ile Leu Tyr Gly Gln Leu Tyr Lys Ser Ile
1               5                   10                  15

Leu Tyr Gly Ser Gly Ser Gly Ser Arg Arg
            20                  25

<210> SEQ ID NO 91
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Gln Leu Tyr Lys Ser Ile Leu Tyr Gly Ser Gly Gln Leu Tyr Lys
1               5                   10                  15

Ser Ile Leu Tyr Gly Ser Gly Ser Gly Ser Arg Arg
            20                  25

<210> SEQ ID NO 92
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: 6-aminohexanoic acid

<400> SEQUENCE: 92

Gly Gln Leu Tyr Lys Ser Ile Leu Tyr Xaa Gly Gln Leu Tyr Lys Ser
1               5                   10                  15

Ile Leu Tyr Gly Ser Gly Ser Gly Ser Arg Arg
            20                  25

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93
```

```
Lys Gly Ser Gly Ser Gly Ser Arg Arg
1               5

<210> SEQ ID NO 94
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Arg Ala Asn Ala Ala Leu Lys Ala Gly Glu Leu Tyr Lys Ser Ile
1               5                   10                  15

Leu Tyr Gly Ser Gly Arg Arg Gly Ser Gly
            20                  25

<210> SEQ ID NO 95
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Gln Leu Tyr Lys Ser Ile Leu Tyr Gly Ser Gly Arg Arg Gly Ser
1               5                   10                  15

Gly

<210> SEQ ID NO 96
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Gln Leu Tyr Lys Ser Ile Leu Tyr Gly Ser Gly Ser Gly Ser Gly
1               5                   10                  15

Ser

<210> SEQ ID NO 97
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Gln Leu Tyr Lys Ser Ile Leu Tyr Gly Ser Arg Gly Arg Gly Ser
1               5                   10                  15

Gly

<210> SEQ ID NO 98
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98
```

Gly Gln Leu Tyr Lys Ser Ile Leu Tyr Gly Arg Ser Gly Arg Gly Ser
1               5                   10                  15

Gly

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Gln Leu Tyr Lys Ser Ile Leu Tyr Gly Ser Arg Gly Ser Gly
1               5                   10                  15

<210> SEQ ID NO 100
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Gln Leu Tyr Lys Ser Ile Leu Tyr Arg Arg Gly Ser Gly Ser Gly
1               5                   10                  15

Ser

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Gln Leu Tyr Lys Ser Ile Leu Tyr Gly Ser Arg Arg Gly Ser
1               5                   10                  15

<210> SEQ ID NO 102
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Gln Leu Tyr Lys Ser Ile Leu Tyr Gly Ser Gly Arg Arg Arg Gly
1               5                   10                  15

Ser Gly

<210> SEQ ID NO 103
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Gln Leu Tyr Lys Ser Ile Leu Tyr Gly Ser Gly Arg Gly Ser Gly
1               5                   10                  15

Ser Gly Ser Gly
            20

<210> SEQ ID NO 104
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Gln Leu Tyr Lys Ser Ile Leu Tyr Gly Ser Gly Lys Lys Gly Ser
1               5                   10                  15

Gly

<210> SEQ ID NO 105
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: 6-aminohexanoic acid
<220> FEATURE:
<221> NAME/KEY: MOD_RES
<222> LOCATION: (13)..(13)
<223> OTHER INFORMATION: 6-aminohexanoic acid

<400> SEQUENCE: 105

Gly Gln Leu Tyr Lys Ser Ile Leu Tyr Xaa Arg Arg Xaa
1               5                   10

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Arg Val Met His Gly Leu His Leu Gly Asp Asp Glu Gly Ser Gly
1               5                   10                  15

<210> SEQ ID NO 107
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Cys Pro Gly Arg Val Met His Gly Leu His Leu Gly Asp Asp Glu Gly
1               5                   10                  15

Pro Cys Gly Ser Gly
            20

<210> SEQ ID NO 108
<211> LENGTH: 26
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 108

Cys Pro Gly Arg Val Met His Gly Leu His Leu Gly Asp Asp Glu Gly
1               5                   10                  15

Pro Cys Gly Ser Gly Arg Arg Gly Ser Gly
            20                  25

<210> SEQ ID NO 109
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Lys Arg Arg Gly Ser Gly
1               5

<210> SEQ ID NO 110
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Trp Arg Glu Pro Ser Phe Ser Ala Leu Ser Gly Ser Gly Ser Gly Ser
1               5                   10                  15

Arg Arg

<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Ser Gly Arg Arg
1               5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Ser Gly Ser Gly Arg Arg
1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

```
Gly Ser Gly Ser Gly Ser Gly Arg Arg
1               5

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gly Ser Gly Ser Gly Ser Gly Ser Arg Arg
1               5                   10

<210> SEQ ID NO 115
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Ser Gly Ser Gly Ser Gly Ser Gly Ser Gly Arg Arg
1               5                   10

<210> SEQ ID NO 116
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Ser Gly Ser Gly Ser Gly Ser Gly Ser Gly Ser Arg Arg
1               5                   10

<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gly Ser Gly Ser Gly Ser Gly Ser Gly Ser Gly Ser Gly Arg Arg
1               5                   10                  15

<210> SEQ ID NO 118
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Ser Arg Arg Gly Ser
1               5

<210> SEQ ID NO 119
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 119

Gly Ser Gly Arg Arg Gly Ser Gly
1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Ser Gly Arg Arg Arg Gly Ser Gly
1               5

<210> SEQ ID NO 121
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gly Ser Gly Arg Arg Arg
1               5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gly Ser Gly Arg Arg Arg Arg
1               5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Ser Gly Ser Gly Ser Arg Arg Arg
1               5

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gly Ser Gly Ser Gly Ser Arg Arg Arg Arg
1               5                   10
```

<210> SEQ ID NO 125
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gly Ser Gly Ser Gly Ser Arg Arg Arg Arg
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Ser Gly Ser Gly Ser Arg Arg Arg Arg Arg
1               5                   10

<210> SEQ ID NO 127
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Ser Gly Ser Gly Ser Gly Ser Arg Arg Arg
1               5                   10

<210> SEQ ID NO 128
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Arg Arg Ala Asn Ala Ala Leu Lys Ala Gly Glu Leu Tyr Lys Ser Ile
1               5                   10                  15

Leu Tyr Gly Ser Gly Ser Gly Ser Arg Arg
            20                  25

<210> SEQ ID NO 129
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Arg Arg Ala Asn Ala Ala Leu Lys Ala Gly Gln Leu Tyr Lys Ser Ile
1               5                   10                  15

Leu Tyr Gly Ser Gly Ser Gly Ser Arg Arg
            20                  25

<210> SEQ ID NO 130
<211> LENGTH: 6

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Lys Ser Gly Ser Arg Arg
1               5

<210> SEQ ID NO 131
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Gln Leu Tyr
1

<210> SEQ ID NO 132
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132

Gly Ser Gly Ser Arg Arg Gly Ser
1               5
```

SYNTHETIC BIOCONJUGATES

CROSS-REFERENCE TO RELATED APPLICATIONS

This application is a U.S. National Stage Application under 35 U.S.C. § 371 of International Application No. PCT/US2018/041259, filed Jul. 9, 2018, which application claims the benefit under 35 U.S.C. § 119(e) to U.S. Provisional Patent Application No. 62/530,047, filed Jul. 7, 2017, the disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Aug. 20, 2018, is named 38FE-248645-WO_SL.txt and is 35,635 bytes in size.

FIELD

Provided herein are bioconjugates comprising a backbone and at least one branched or unbranched peptide having at least one collagen-binding unit covalently bonded thereto via a spacer.

BACKGROUND

In tissues, cells are surrounded by an extracellular matrix (ECM) containing various macromolecules, such as bioconjugates, collagen, hyaluronic acid, laminin, fibronectin, etc. In mammals, bioconjugates are a major component of the extracellular matrix, where they form large complexes, both to other bioconjugates, to hyaluronic acid, and to fibrous matrix proteins (such as collagen). As mammals age and in some disease states, the extracellular matrix in certain areas of the body (e.g., in synovial joints, the vitreous humor, the spinal discs, the skin, etc.) can degrade, causing undesirable symptoms, such as various forms of arthritis, loss of vision, and the like. In addition, some tissue injuries, such as vascular injury, corneal injury and dermal wounds, result in the exposure of the extracellular matrix and/or components thereof, including collagen.

SUMMARY

It has been surprisingly found that bioconjugates having a certain linkage between the glycan and peptides leads to increased binding of certain peptides to their targets. It has also been found that having branched peptides leads to improved binding. Specifically, bioconjugates having certain spacers provided enhanced collagen binding activity.

The present disclosure provides a bioconjugate comprising a glycan and at least one binding unit of formula (I) covalently bonded thereto:

$$((X^1)_m X^2)_n X^3\text{-}L \qquad (I)$$

wherein:

$X^1$ is an amino acid sequence comprising a collagen-binding unit;

$X^2$ and $X^3$ are independently absent, an amino acid sequence having from 1 to 15 amino acids; or a moiety

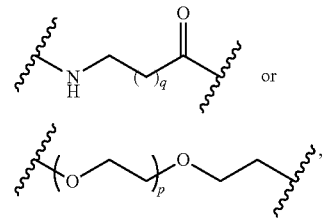

where p and q are each independently an integer from 1 to 10;

L is a spacer of 5 to 20 amino acids selected from the group consisting glycine (G), serine (S), arginine (R), and lysine (K), or a moiety

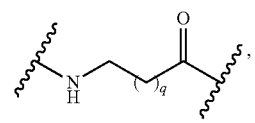

provided L comprises at least two arginines (R) within the first five amino acids from the glycan, and wherein L further comprises an optional linking moiety which covalently bonds the peptide to the glycan;

m is 1 or 2; and n is 1 or 2.

In one embodiment, L is not GSGKRRGSG (SEQ ID NO: 1).

In one embodiment, $X^1$ is the N-terminus of the peptide, and $X^3$ is at the C-terminus of the peptide.

In one embodiment, formula (I) is not RRRKKIQGRSKR (SEQ ID NO: 2) or RRGGRKWGSFEG (SEQ ID NO: 3).

In one embodiment, the linking moiety is —NHNH—.

In one embodiment, provided is a functionalized peptide of formula:

$$L\text{-NHNH}_2$$

wherein L is a spacer of from 5 to 20 amino acids selected from the group consisting glycine (G), serine (S), arginine (R), and lysine (K), or a moiety

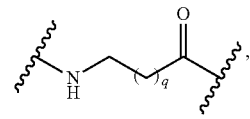

provided L comprises at least two arginines (R) within the first five amino acids from the —NHNH$_2$ moiety.

In one embodiment, L is -GSGSGSRR—NHNH— (SEQ ID NO: 4). Also provided is a peptide comprising GSGSGSRR (SEQ ID NO: 4).

The present disclosure also provides a binding unit of formula (II):

$$((X^1)_m X^2)_n X^3\text{-}L \qquad (II)$$

wherein:

$X^1$ is an amino acid sequence comprising a collagen-binding unit;

$X^2$ and $X^3$ are independently absent, an amino acid sequence having from 1 to 15 amino acids; or a moiety $$\begin{array}{c} \text{\textit{\large{}{}{}{}}} \\ \overset{O}{\underset{H}{N}} \overset{}{\overbrace{\phantom{xx}}_{q}} \end{array} \text{ or }$$

$$\begin{array}{c} \overset{}{\underset{}{O}} \overset{}{\overbrace{\phantom{xx}}_{p}} \overset{O}{\underset{}{}} \end{array},$$

where p and q are each independently an integer from 1 to 10;

L is a spacer of from 5 to 20 amino acids selected from the group consisting of glycine (G), serine (S), arginine (R), and lysine (K), or a moiety $$\begin{array}{c} \overset{O}{\underset{H}{N}} \overset{}{\overbrace{\phantom{xx}}_{q}} \end{array},$$

provided L comprises at least two arginines (R) within the first five amino acids from the terminus, and wherein L further comprises an optional linking moiety;

m is 1 or 2; and n is 1 or 2;

provided that formula (II) is not RRRKKIQGRSKR (SEQ ID NO: 2) or RRGGRKWGSFEG (SEQ ID NO: 3).

In certain embodiments, m is 1 and n is 2. In certain embodiments, m is 2 and n is 1. In certain embodiments, m is 2 and n is 2.

In certain embodiments, $X^2$ and $X^3$ are independently absent, an amino acid sequence having from 1 to 15 amino acids selected from the group consisting of glycine (G), serine (S), arginine (R), and lysine (K), or a moiety $$\begin{array}{c} \overset{O}{\underset{H}{N}} \overset{}{\overbrace{\phantom{xx}}_{q}} \end{array} \text{ or }$$

$$\begin{array}{c} \overset{}{\underset{}{O}} \overset{}{\overbrace{\phantom{xx}}_{p}} \overset{O}{\underset{}{}} \end{array},$$

wherein p and q are each independently an integer from 1 to 10. In certain embodiments, $X^2$ and $X^3$ are independently absent or an amino acid sequence having from 1 to 15 amino acids selected from the group consisting of glycine (G), serine (S), arginine (R), and lysine (K).

In certain embodiments, when m and/or n are other than 1, at least one of $X^2$ and $X^3$ comprises at least one arginine (R) or lysine (K). In certain embodiments, when m and/or n are other than 1, $X^2$ and $X^3$ do not comprise arginine (R) or lysine (K).

In certain embodiments, L comprises a hydrazide.

BRIEF DESCRIPTION OF THE DRAWINGS

Certain aspects of the present disclosure can be viewed by the accompanying figures. Included are the following:

FIG. 19 shows the effect of adding the GSGSGSRR (SEQ ID NO: 4) spacer sequence to collagen binding domain WREPSFSALS (SEQ ID NO: 8), vWF-2×.

DETAILED DESCRIPTION

Figure 1:
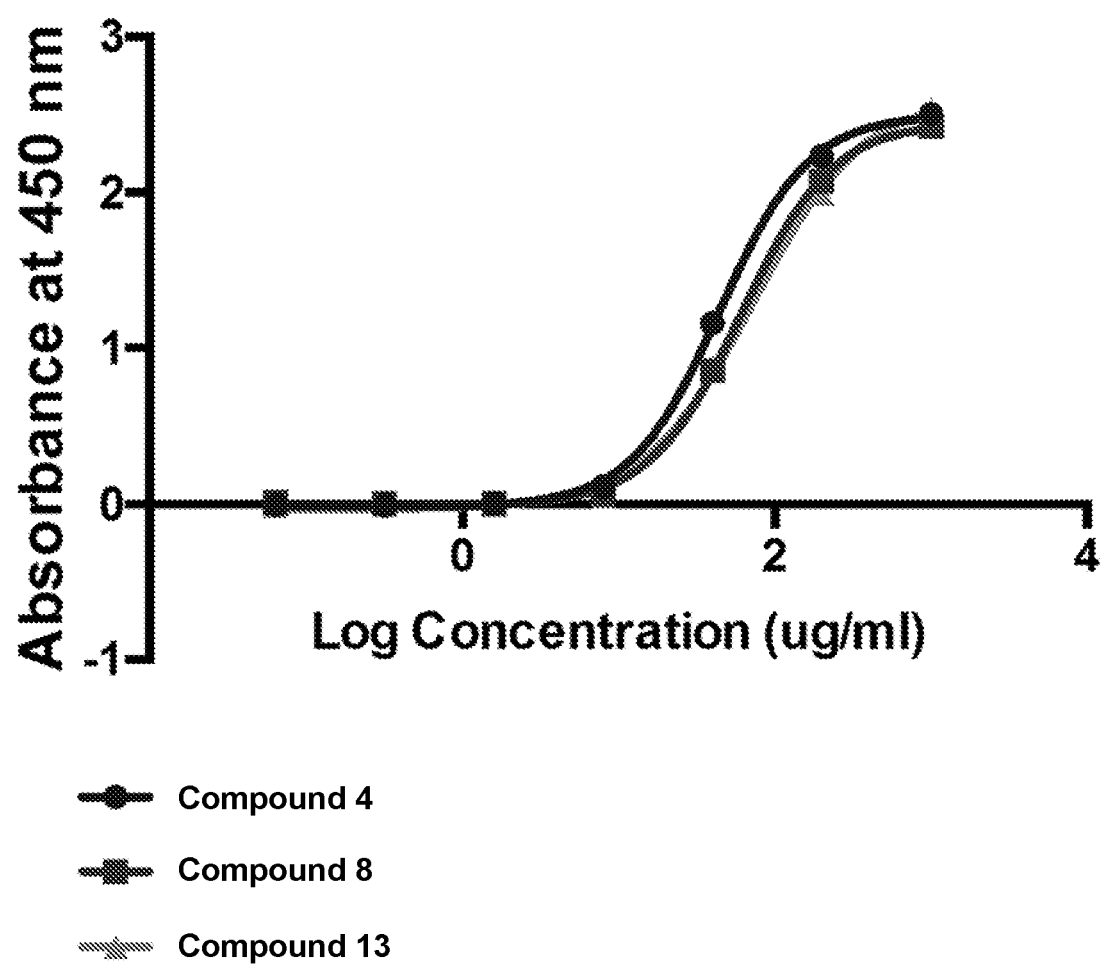
FIG. 1 shows a comparison of collagen binding for bioconjugates Compound 4, Compound 8, and Compound 13.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

I. Definitions

Unless defined otherwise, all technical and scientific terms used herein have the same meaning as commonly understood by one of ordinary skill in the art to which this disclosure belongs. It must be noted that as used herein and in the appended claims, the singular forms "a", "an", and "the" include plural referents unless the context clearly dictates otherwise. Thus, for example, reference to "a peptide" includes a plurality of peptides.

As used herein the following terms and abbreviations have the following meanings.

| | |
|---|---|
| BMPH | N-β-maleimidopropionic acid hydrazide |
| DCC | N,N'-dicyclohexylcarbodiimide |
| DIC | N,N'-diisopropylcarbodiimide |
| EDC | 1-ethyl-3-(3-dimethylaminopropyl)carbodiimide |
| BMC | N-t-butyl-N-methylcarbodiimide |
| BEC | N-t-butyl-N-ethylcarbodiimide |
| BDDC | 1,3-bis(2,2-dimethyl-1,3-dioxolan-4-ylmethyl)carbodiimide |
| HFA | Hexafluoroacetone |
| CDI | Carbonyldiimidazole |
| HOBt | Hydroxybenzotriazole |
| PyBOP | Benzotriazol-1-yl-oxytripyrrolidinophosphonium hexafluorophosphate |
| HOAt | 1-Hydroxy-7-azabenzotriazole |
| TBTU | O-(Benzotriazol-1-yl)-N,N,N'N'-tetramethyluronium tetrafluoroborate. |
| HOSu | N-hydroxysuccinimide |
| Hep | Heparin |
| DNA | Deoxyribonucleic acid |
| EDTA | Ethylenediaminetetraacetic Acid |
| ELISA | Enzyme-Linked Immunosorbent Assay |
| FGF | Fibroblast Growth Factor |
| HEPES | 2-[4-(2-hydroxyethyl)piperazin-1-yl] ethanesulfonic acid |
| HLB | Hydrophile/Lipophile/Balance |
| ITC | Isothermal Titration Calorimeters |
| kDa | KiloDalton |
| GAG | Glycosaminoglycan |
| MES | 2-ethanesulfonic acid |
| ESRD | End-stage renal disease |
| $K_d$ | Dissociation constant |
| vWF | von Willebrand factor |
| MMP | Matrix metalloproteinase enzymes |
| CVs | Column volumes |
| TMP | Trimethyl phosphate |
| PF-4 | Platelet factor 4 |
| BSA | Bovine serum albumin |
| DG | Deionized water |
| PEGDA | Polyethylene glycol diacrylate |
| MOPS | 3-(N-morpholino)propanesulfonic acid |
| PBS | Phosphate buffered saline |
| PIPES | Piperazine-N,N'-bis(2-ethanesulfonic acid) |
| SPR | Surface Plasmon Resonance |
| TAPS | 3-[[1,3-dihydroxy-2-(hydroxymethyl)propan-2-yl]amino]propane-1-sulfonic acid |
| TES | 2-[[1,3-dihydroxy-2-(hydroxymethyl)propan-2-yl] amino]ethanesulfonic acid |
| Tris | 2-Amino-2-hydroxymethyl-propane-1,3-diol |
| w/w | Weight/Weight |
| w/v | Weight/Volume |
| EC50 | concentration required to elicit half-maximal response |

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) claimed. "Consisting of" shall mean excluding more than trace elements of other ingredients and substantial method steps. Embodiments defined by each of these transition terms are within the scope of this disclosure.

The term "about" when used before a numerical designation, e.g., temperature, time, amount, and concentration, including range, indicates approximations which may vary by (+) or (−) 10%, 5% or 1%.

As used herein, the terms "bioconjugate," "peptidoglycan," and "proteoglycan," and "synthetic proteoglycan" are used interchangeably and refer to a synthetic conjugate that comprises glycan and one or more peptides covalently bonded thereto. The glycan portion can be made synthetically or derived from animal sources. The peptides are covalently bound to the glycan, in certain embodiments, via a hydrazide-carbonyl linkage (i.e., —C(O)—NH—NH—C(O)—). In certain embodiments, the hydrazide-carbonyl linkage is between a terminal hydrazide group on the peptides and a carbonyl group on the glycan. In other embodiments, the hydrazide-carbonyl linkage is between a terminal carbonyl group on the peptides and a hydrazide group on the glycan. In some embodiments, the term bioconjugate includes peptidoglycan.

As used herein, the term "glycan" refers to a compound having a large number of monosaccharides linked glycosidically. In certain embodiments, the glycan is a glycosaminoglycan (GAG), which comprise 2-aminosugars linked in an alternating fashion with uronic acids, and include polymers such as heparin, heparan sulfate, chondroitin, keratin, and dermatan. Accordingly, non-limiting examples of glycans which can be used in the embodiments described herein include alginate, agarose, dextran, dextran sulfate, chondroitin, chondroitin sulfate (CS), dermatan, dermatan sulfate (DS), heparan sulfate, heparin (Hep), keratin, keratan sulfate, and hyaluronic acid (HA), including derivatives thereof. In another embodiment, the molecular weight of the glycan is varied to tailor the effects of the bioconjugate (see e.g., Radek, K. A., et al., Wound Repair Regen., 2009, 17: 118-126; and Taylor, K. R., et al., J. Biol. Chem., 2005, 280:5300-5306). In one embodiment, the glycan is degraded by oxidation and alkaline elimination (see e.g., Fransson, L. A., et al., Eur. J. Biochem., 1980, 106:59-69) to afford degraded glycan having a lower molecular weight (e.g., from about 10 kDa to about 50 kDa). In some embodiments, the glycan is unmodified. In certain embodiments, the glycan does not contain oxidatively cleaved saccharide rings and thus does not, and has not, contain(ed) aldehyde functional groups. In certain embodiments, the glycan is derivatized.

As used herein, the term "derivatized glycan" is intended to include derivatives of glycans. For example, a derivatized glycan can include one or more chemical derivatizations, such as, but not limited to partially N-desulfated derivatives, partially O-desulfated derivatives, and/or partially O-carboxymethylated derivatives. For example, as used herein, the term "heparin" is intended to include heparin and derivatives thereof, such as, but not limited to partially N- and/or partially O-desulfated heparin derivatives, partially O-carboxymethylated heparin derivatives, or a combination thereof. In certain embodiments, the heparin is non-oxidized heparin (i.e., does not contain oxidatively cleaved saccharide rings) and does not contain aldehyde functional groups.

As used herein, the terms "bonded" and "covalently bonded" can be used interchangeably and refer to the sharing of one or more pairs of electrons by two atoms.

In one embodiment, the bioconjugates of the disclosure bind, either directly or indirectly to collagen. The terms "binding" or "bind" as used herein are meant to include interactions between molecules that may be detected using, for example, a hybridization assay, surface plasmon resonance, ELISA, competitive binding assays, isothermal titration calorimetry, phage display, affinity chromatography, rheology or immunohistochemistry. The terms are also meant to include "binding" interactions between molecules. Binding may be "direct" or "indirect." "Direct" binding comprises direct physical contact between molecules. "Indirect" binding between molecules comprises the molecules having direct physical contact with one or more molecules simultaneously. This binding can result in the formation of a "complex" comprising the interacting molecules. A "complex" refers to the binding of two or more molecules held together by covalent or non-covalent bonds, interactions or forces.

As used herein, the term "composition" refers to a preparation suitable for administration to an intended patient for therapeutic purposes that contains at least one pharmaceutically active ingredient, including any solid form thereof. The composition may include at least one pharmaceutically acceptable component to provide an improved formulation of the compound, such as a suitable carrier. In certain embodiments, the composition is formulated as a film, gel, patch, or liquid solution. As used herein, the term "topically" refers to administering a composition non-systemically to the surface of a tissue and/or organ (internal or, in some cases, external) to be treated, for local effect.

As used herein, the term "pharmaceutically acceptable" indicates that the indicated material does not have properties that would cause a reasonably prudent medical practitioner to avoid administration to a patient, taking into consideration the amount used and/or the disease or conditions to be treated and the respective route of administration. Typical pharmaceutically acceptable materials are essentially sterile. As used herein, the term "pharmaceutically acceptable carrier" refers to pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body, or to deliver an agent to the internal surface of a vein.

As used herein, the term "solution" refers to solutions, suspensions, emulsions, drops, ointments, liquid wash, sprays, and liposomes, which are well known in the art. In some embodiments, the liquid solution contains an aqueous pH buffering agent which resists changes in pH when small quantities of acid or base are added. In certain embodiments, the liquid solution contains a lubricity enhancing agent.

As used herein, the term "polymer," "polymer matrix" or "polymeric agent" refers to a biocompatible polymeric material. The polymeric material described herein may comprise, for example, sugars (such as mannitol), peptides, protein, laminin, collagen, hyaluronic acid, ionic and non-ionic water soluble polymers; acrylic acid polymers; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; poly(lactic acid), poly(glycolic acid), copolymers of lactic and glycolic acids, or other polymeric agents, both natural and synthetic.

In certain embodiments, the polymeric matrix is absorbable, such as, for example collagen, polyglycolic acid, polylactic acid, polydioxanone, and caprolactone. As used herein, the term "absorbable" refers to the ability of a material to be absorbed into the body. In other embodiments, the polymer is non-absorbable, such as, for example polypropylene, polyester or nylon.

As used herein, the term "pH buffering agent" refers to an aqueous buffer solution which resists changes in pH when small quantities of acid or base are added to it. pH Buffering solutions typically comprise a mixture of weak acid and its conjugate base, or vice versa. For example, pH buffering solutions may comprise phosphates such as sodium phosphate, sodium dihydrogen phosphate, sodium dihydrogen phosphate dihydrate, disodium hydrogen phosphate, disodium hydrogen phosphate dodecahydrate, potassium phosphate, potassium dihydrogen phosphate and dipotassium hydrogen phosphate; boric acid and borates such as, sodium borate and potassium borate; citric acid and citrates such as sodium citrate and disodium citrate; acetates such as sodium acetate and potassium acetate; carbonates such as sodium carbonate and sodium hydrogen carbonate, etc. pH Adjusting agents can include, for example, acids such as hydrochloric acid, lactic acid, citric acid, phosphoric acid and acetic acid, and alkaline bases such as sodium hydroxide, potassium hydroxide, sodium carbonate and sodium hydrogen carbonate, etc. In some embodiments, the pH buffering agent is a phosphate buffered saline (PBS) solution (i.e., containing sodium phosphate, sodium chloride and in some formulations, potassium chloride and potassium phosphate).

As used herein, the terms "peptide" and "peptide sequence" are intended to refer to a linear or branched chain of amino acids linked by peptide (or amide) bonds. In one embodiment, the peptide comprises from about 3 to about 120 amino acids, or from about 3 to about 110 amino acids, or from about 3 to about 100 amino acids, or from about 3 to about 90 amino acids, or from about 3 to about 80 amino acids, or from about 3 to about 70 amino acids, or from about 3 to about 60 amino acids, or from about 3 to about 50 amino acids, or from about 3 to about 40 amino acids, or from about 5 to about 120 amino acids, or from about 5 to about 100 amino acids, or from about 5 to about 90 amino acids, or from about 5 to about 80 amino acids, or from about 5 to about 70 amino acids, or from about 5 to about 60 amino acids, or from about 5 to about 50 amino acids, or from about 5 to about 40 amino acids, or from about 5 to about 30 amino acids, or from about 5 to about 20 amino acids, or from about 5 to about 10 amino acids.

In various embodiments described herein, the peptides can be modified by the inclusion of one or more conservative amino acid substitutions in the binding unit. As is well known to those skilled in the art, altering any non-critical amino acid of a peptide by conservative substitution should not significantly alter the activity of that peptide because the side-chain of the replacement amino acid should be able to form similar bonds and contacts to the side chain of the amino acid which has been replaced. Non-conservative substitutions may too be possible, provided that they do not substantially affect the binding activity of the peptide.

As used herein, the term "sequence identity" refers to a level of amino acid residue or nucleotide identity between two peptides or between two nucleic acid molecules. When a position in the compared sequence is occupied by the same base or amino acid, then the molecules are identical at that position. A peptide (or a polypeptide or peptide region) has a certain percentage (for example, at least about 60%, or at least about 65%, or at least about 70%, or at least about 75%, or at least about 80%, or at least about 83%, or at least about 85%, or at least about 90%, or at least about 95%, or at least about 98% or at least about 99%) of "sequence identity" to another sequence means that, when aligned, that percentage of bases (or amino acids) are the same in comparing the two sequences. It is noted that, for any sequence ("reference sequence") disclosed in this application, sequences having at least about 60%, or at least about 65%, or at least about 70%, or at least about 75%, or at least about 80%, or at least about 83%, or at least about 85%, or at least about 90%, or at least about 95%, or at least about 98% or at least about 99% sequence identity to the reference sequence are also within the disclosure. Likewise, the present disclosure also includes sequences that have one, two, three, four, or five substitution, deletion or addition of amino acid residues or nucleotides as compared to the reference sequences. In certain embodiments, in any one or more of the sequences specified herein, the sequence may be modified by having one, two, or three amino addition, deletion and/or substitution each therefrom.

As is well-known in the art, a "conservative substitution" of an amino acid or a "conservative substitution variant" of a peptide refers to an amino acid substitution which maintains: 1) the secondary structure of the peptide; 2) the charge or hydrophobicity of the amino acid; and 3) the bulkiness of the side chain or any one or more of these characteristics. Illustratively, the well-known terminologies "hydrophilic residues" relate to serine or threonine. "Hydrophobic residues" refer to leucine, isoleucine, phenylalanine, valine or alanine, or the like. "Positively charged residues" relate to lysine, arginine, ornithine, or histidine. "Negatively charged residues" refer to aspartic acid or glutamic acid. Residues having "bulky side chains" refer to phenylalanine, tryptophan or tyrosine, or the like. A list of illustrative conservative amino acid substitutions is given in Table 1.

TABLE 1

| For Amino Acid | Replace With |
| --- | --- |
| Alanine | D-Ala, Gly, Aib, β-Ala, L-Cys, D-Cys |
| Arginine | D-Arg, Lys, D-Lys, Orn, D-Orn |
| Asparagine | D-Asn, Asp, D-Asp, Glu, D-Glu, Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

In some embodiments, the sequences described herein may be modified to replace one or more glutamic acid residue(s) with glutamine and/or one or more aspartic acid residue(s) with asparagine.

Collagen-Binding Unit

As used herein, the term "collagen-binding unit" is intended to refer to an amino acid sequence within a peptide which binds to collagen. "Collagen-binding" indicates an interaction with collagen that could include hydrophobic, ionic (charge), and/or Van der Waals interactions, such that the compound binds or interacts favorably with collagen. This binding (or interaction) is intended to be differentiated from covalent bonds and nonspecific interactions with common functional groups, such that the peptide would interact with any species containing that functional group to which the peptide binds on the collagen. Peptides can be tested and assessed for binding to collagen using any method known in the art. See, e.g., Li, Y., et al., Current Opinion in Chemical Biology, 2013, 17: 968-975, Helmes, B. A., et al., J. Am. Chem. Soc. 2009, 131, 11683-11685, and Petsalaki, E., et al., PLoS Comput Biol, 2009, 5(3): e1000335. In one embodiment, the peptide, or the collagen-binding unit of the peptide, binds to collagen with a dissociation constant ($K_d$) of less than about 1 mM, or less than about 900 µM, or less than about 800 µM, or less than about 700 µM, or less than about 600 µM, or less than about 500 µM, or less than about 400 µM, or less than about 300 µM, or less than about 200 µM, or less than about 100 µM. In certain embodiments, the collagen-binding units comprise up to about 120 amino acids.

The peptide can have amino acid homology with a portion of a protein normally or not normally involved in collagen fibrillogenesis. In some embodiments, these peptides have homology or sequence identity to the amino acid sequence of a small leucine-rich bioconjugate, a platelet receptor sequence, or a protein that regulates collagen fibrillogenesis. In various embodiments, the peptide comprises an amino acid sequence selected from RRANAALKAGELYKSILY (SEQ ID NO: 9), GELYKSILY (SEQ ID NO: 10), RRANAALKAGELYKCILY (SEQ ID NO: 11), GELYKCILY (SEQ ID NO: 12), RRANAALKAGQLYKSILY (SEQ ID NO: 13), GQLYKSILY (SEQ ID NO: 5), RRANAALKAGQLYKCILY (SEQ ID NO: 14), GQLYKCILY (SEQ ID NO: 15), RLDGNEIKR (SEQ ID NO: 16), AHEEISTTNEGVM (SEQ ID NO: 17), NGVFKYRPRYFLYKHAYFYPPLKRFPVQ (SEQ ID NO: 18), CQDSETRTFY (SEQ ID NO: 19), TKKTLRT (SEQ ID NO: 20), GLRSKSKKFRRPDIQYPDATDEDITSHM (SEQ ID NO: 21), SQNPVQP (SEQ ID NO: 22), SYIRIADTNIT (SEQ ID NO: 23), KELNLVYT (SEQ ID NO: 24), GSIT (SEQ ID NO: 25), GSITTIDVPWNV (SEQ ID NO: 26), GQLYKSILY (SEQ ID NO: 5), RRANAALKAGQLYKSILY (SEQ ID NO: 13), RVMHGLHLGDDE ("GPVI") (SEQ ID NO: 27), CRVMHGLHLGDDEC (cyclic RVMHGLHLGDDE (SEQ ID NO: 27) or "cGPVI") (SEQ ID NO: 28), or a sequence having at least about 80% sequence identity, or at least about 83% sequence identity, or at least about 85% sequence identity, or at least about 90% sequence identity, or at least about 95% sequence identity, or at least about 98% sequence identity thereto, provided the sequence is capable of binding to collagen.

In certain embodiments, the peptide comprises an amino acid sequence that has at least about 80%, or at least about 83%, or at least about 85%, or at least about 90%, or at least about 95%, or at least about 98%, or at least about 100% sequence identity with the collagen-binding domain(s) of the von Willebrand factor (vWF) or a platelet collagen receptor as described in Chiang, T. M., et al. J. Biol. Chem., 2002, 277: 34896-34901, Huizinga, E. G. et al., Structure, 1997, 5: 1147-1156, Romijn, R. A., et al., J. Biol. Chem., 2003, 278: 15035-15039, and Chiang, et al., Cardio. & Haemato. Disorders-Drug Targets, 2007, 7: 71-75, each incorporated herein by reference. A non-limiting example is WREPSFCALS (SEQ ID NO: 29), derived from vWF.

Various methods for screening peptide sequences for collagen-binding affinity (or a collagen-binding domain/unit) are routine in the art. Other peptide sequences shown to have collagen-binding affinity (or a collagen-binding unit) which can be used in the bioconjugates and methods disclosed herein include but are not limited to, βAWHCTTKFPHHYCLYBip (SEQ ID NO: 30), βAHKCPWHLYTTHYCFTBip (SEQ ID NO: 31), βAHKCPWHLYTHYCFT (SEQ ID NO: 32), etc., where Bip is biphenylalanine and βA is beta-alanine (see, Abd-Elgaliel, W. R., et al., Biopolymers, 2013, 100(2), 167-173), GROGER (SEQ ID NO: 33), GMOGER (SEQ ID NO: 34), GLOGEN (SEQ ID NO: 35), GLOGER (SEQ ID NO: 36), GLKGEN (SEQ ID NO: 37), GFOGERGVEGPOGPA (SEQ ID NO: 38), etc., where O is 4-hydroxyproline (see, Raynal, N., et al., J. Biol. Chem., 2006, 281(7), 3821-3831), HVWMQAPGGGK (SEQ ID NO: 39) (see, Helms, B. A., et al., J. Am. Chem. Soc. 2009, 131, 11683-11685), WREPSFCALS (SEQ ID NO: 29) (see, Takagi, J., et al., Biochemistry, 1992, 31, 8530-8534), WYRGRL (SEQ ID NO: 40), etc. (see, Rothenfluh D. A., et al., Nat Mater. 2008, 7(3), 248-54), WTCSGDEYTWHC (SEQ ID NO: 41), WTCVGDHKTWKC (SEQ ID NO: 42), QWHCTTRFPHHYCLYG (SEQ ID NO: 43), etc. (see, U.S. 2007/0293656), STWTWNGSAWTWNEGGK (SEQ ID NO: 44), STWTWNGTNWTRNDGGK (SEQ ID NO: 45), etc. (see, WO/2014/059530), CVWLWEQC (SEQ ID NO: 46) cyclic CVWLWENC (SEQ ID NO: 47), cyclic CVWLWEQC (SEQ ID NO: 46), (see, Depraetere H., et al., Blood. 1998, 92, 4207-4211, and Duncan R., Nat Rev Drug Discov, 2003, 2(5), 347-360), CMTSPWRC (SEQ ID NO: 48), etc. (see, Vanhoorelbeke, K., et al., J. Biol. Chem., 2003, 278, 37815-37821), CPGRVMHGLHLGDDEGPC (SEQ ID NO: 49) (see, Muzzard, J., et al., PLoS one. 4 (e 5585) 1-10), KLWLLPK (SEQ ID NO: 50) (see, Chan, J. M., et al., Proc Natl Acad Sci U.S.A., 2010, 107, 2213-2218), and CQDSETRTFY (SEQ ID NO: 19), etc. (see, U.S. 2013/0243700), H-V-F/W-Q/M-Q-P/A-P/K (Helms, B. A., et al., J. Am. Chem. Soc., 2009, 131(33), 11683-11685), wherein each is hereby incorporated by reference in its entirety.

Additional peptide sequences shown to have collagen-binding affinity (or a collagen-binding unit) which can be used in the bioconjugates and methods disclosed herein include but are not limited to, LSELRLHEN (SEQ ID NO: 51), LTELHLDNN (SEQ ID NO: 52), LSELRLHNN (SEQ ID NO: 53), LSELRLHAN (SEQ ID NO: 54), and LRELHLNNN (SEQ ID NO: 55) (see, Fredrico, S., Angew. Chem. Int. Ed. 2015, 37, 10980-10984).

In certain embodiments, the peptides include one or more sequences selected from the group consisting of RVMHGLHLGDDE (SEQ ID NO: 27), D-amino acid EDDGLHLGHMVR (SEQ ID NO: 56), RVMHGLHLGNNQ (SEQ ID NO: 57), D-amino acid QNNGLHLGHMVR (SEQ ID NO: 58), RVMHGLHLGNNQ (SEQ ID NO: 57), GQLYKSILYGSG-4K2K (core peptide disclosed as SEQ ID NO: 59) (a 4-branch peptide), GSGQLYKSILY (SEQ ID NO: 60), GSGGQLYKSILY (SEQ ID NO: 61), KQLNLVYT (SEQ ID NO: 62), CVWLWQQC (SEQ ID NO: 63), WREPSFSALS (SEQ ID NO: 8), GHRPLDKKREEAPSLRPAPPPISGGGYR (SEQ ID NO: 64), and GHRPLNKKRQQAPSLRPAPPPISGGGYR (SEQ ID NO: 65).

Similarly for a collagen-binding unit, a peptide sequence derived from a phage display library selected for collagen can be generated. The peptide can be synthesized and evaluated for binding to collagen by any of the techniques such as SPR, ELISA, ITC, affinity chromatography, or others known in the art. An example could be a biotin modified peptide sequence (e.g., SILY$_{biotin}$ (SEQ ID NO: 66)) that is incubated on a microplate containing immobilized collagen. A dose response binding curve can be generated using a streptavidin-chromophore to determine the ability of the peptide to bind to collagen.

In one embodiment, the peptides comprise one or more collagen-binding units which binds any one or more of collagen type I, II, III, IV, V, VI, VII, VIII, IX, X, XI, XII, XIII, or XIV. In one embodiment, the peptide binds to type I collagen with a dissociation constant ($K_d$) of less than about 1 mM, or less than about 900 μM, or less than about 800 μM, or less than about 700 μM, or less than about 600 μM, or less than about 500 μM, or less than about 400 μM, or less than about 300 μM, or less than about 200 μM, or less than about 100 μM. In one embodiment, the peptide binds to type II collagen with a dissociation constant ($K_d$) of less than about 1 mM, or less than about 900 μM, or less than about 800 μM, or less than about 700 μM, or less than about 600 μM, or less than about 500 μM, or less than about 400 μM, or less than about 300 μM, or less than about 200 μM, or less than about 100 μM. In one embodiment, the peptide binds to type III collagen with a dissociation constant ($K_d$) of less than about 1 mM, or less than about 900 μM, or less than about 800 μM, or less than about 700 μM, or less than about 600 μM, or less than about 500 μM, or less than about 400 μM, or less than about 300 μM, or less than about 200 μM, or less than about 100 μM. In one embodiment, the peptide binds to type IV collagen with a dissociation constant ($K_d$) of less than about 1 mM, or less than about 900 μM, or less than about 800 μM, or less than about 700 μM, or less than about 600 μM, or less than about 500 μM, or less than about 400 μM, or less than about 300 μM, or less than about 200 μM, or less than about 100 μM.

In certain embodiments, any sequence described herein may be modified such that any one or more amino acids (e.g., 1, 2, 3, 4 or 5 amino acids) are added, deleted or substituted therefrom. In some embodiments, the sequence is modified such that any one or more amino acids is replaced by alanine. In some embodiments, the sequence is modified such that any one or more l-amino acid is replaced the corresponding d-amino acid scan. In some embodiments, the sequence is modified such that any one or more valine is replaced by leucine, any one or more glutamic acid is replaced by glutamine, any one or more aspartic acid is replaced by asparagine, and/or any one or more arginine is replaced by glutamine.

In any of the embodiments described herein, the peptide having a collagen-binding unit comprises any amino acid sequence described in the preceding paragraphs or an amino acid sequence having at least about 80%, or at least about 83%, or at least about 85%, or at least about 90%, or at least about 95%, or at least about 98%, or at least about 100% homology to any of these amino acid sequences. In various embodiments, the peptide components of the synthetic bioconjugates described herein can be modified by the inclusion of one or more conservative amino acid substitutions. As is well-known to those skilled in the art, altering any non-critical amino acid of a peptide by conservative substitution should not significantly alter the activity of that peptide because the side-chain of the replacement amino acid should be able to form similar bonds and contacts to the side chain of the amino acid which has been replaced.

Peptides may also be selected by phage display, utilizing positive selection for binding to collagen. A collagen-binding unit may be determined by its interaction with collagen, and measured by any of the techniques used to evaluate molecular interactions (such as surface plasmon resonance, ELISA, competitive binding assays, isothermal titration calorimetry, affinity chromatography, rheology and/or immunohistochemistry). Peptides that are considered "collagen-binding" may interact with collagen or collagen-containing tissues such that the interaction is not attributed to known chemically reactive groups. The interaction may be due to hydrophobic and charge interactions resulting from the amino acid residues in the peptide. The interaction may be measured by immobilizing collagen on a microplate and incubating with collagen-binding units followed by detection techniques such as biotin-avidin with the use of a chromophore. The interaction may also be measured by mechanical influence on collagen-containing fluids, gels, or tissues that have been incubated with the collagen-binding unit or with a bioconjugate containing an collagen-binding unit or units.

Bioconjugates

Provided herein is a bioconjugate comprising a glycan and at least one binding unit of formula (I) covalently bonded thereto:

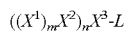 (I)

wherein:

$X^1$ is an amino acid sequence comprising a collagen-binding unit;

$X^2$ and $X^3$ are independently absent, an amino acid sequence having from 1 to 15 amino acids; or a moiety

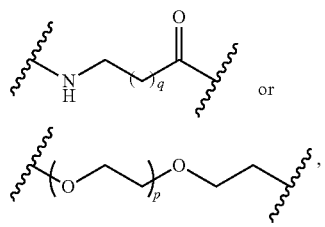

where p and q are each independently an integer from 1 to 10;

L is a spacer of from 3 to 20 amino acids selected from the group consisting glycine (G), serine (S), arginine (R), and lysine (K), or a moiety

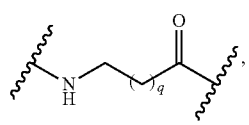

provided L comprises at least two arginines (R) within the first five amino acids from the glycan, and wherein L further comprises an optional linking moiety which covalently bonds the peptide to the glycan;

m is 1 or 2; and n is 1 or 2.

In one embodiment, provided is a bioconjugate comprising a glycan and at least one binding unit of formula (I) covalently bonded thereto:

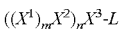 (I)

wherein:

$X^1$ is an amino acid sequence comprising a collagen-binding unit;

$X^2$ and $X^3$ are independently absent, an amino acid sequence having from 1 to 15 amino acids; or a moiety

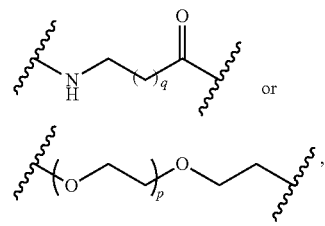

where p and q are each independently an integer from 1 to 10;

L is a spacer of from 3 to 20 amino acids selected from the group consisting glycine (G), serine (S), arginine (R), and lysine (K), or a moiety

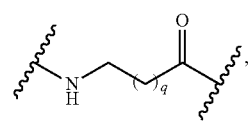

provided L comprises at least two arginines (R) within the first five amino acids from the glycan, and wherein L further comprises an optional linking moiety which covalently bonds the peptide to the glycan;

m is 1 or 2; and n is 1 or 2.

In one embodiment, $X^1$ is at the N-terminus of the peptide, and $X^3$ is at the C-terminus of the peptide.

In one embodiment, formula (I) is not RRRKKIQGRSKR (SEQ ID NO: 2) or RRGGRKWGSFEG (SEQ ID NO: 3).

In certain embodiments, m is 1 and n is 2. In certain embodiments, m is 2 and n is 1. In certain embodiments, m is 2 and n is 2.

In certain embodiments, it is contemplated that L can be a spacer of from 3 to 20 amino acids selected from the group consisting glycine (G), serine (S), arginine (R), and lysine (K), or a moiety

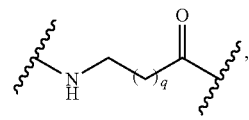

provided L comprises at least two arginines (R) within the first three amino acids from a terminus, and wherein L further comprises an optional linking moiety.

In certain embodiments, $X^2$ and $X^3$ are independently absent, an amino acid sequence having from 1 to 15 amino acids selected from the group consisting of glycine (G), serine (S), arginine (R), and lysine (K), or a moiety

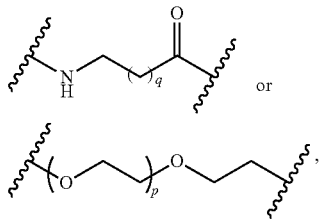

wherein p and q are each independently an integer from 1 to 10. In certain embodiments, $X^2$ and $X^3$ are independently absent or an amino acid sequence having from 1 to 15 amino acids selected from the group consisting of glycine (G), serine (S), arginine (R), and lysine (K).

In certain embodiments, when m and/or n are other than 1, at least one of $X^2$ and $X^3$ comprises at least one arginine (R) or lysine (K). In certain embodiments, when m and/or n are other than 1, $X^2$ and $X^3$ do not comprise arginine (R) or lysine (K).

In some embodiments, $X^2$, $X^3$, and L, collectively, include more than two arginines. In some embodiments, $X^3$ includes two or more arginines. In some embodiments, L includes more than two or more arginines.

In some embodiments, $X^2$ is from 2 to 5 amino acids in length where each amino acid is selected from glycine and/or serine. In some embodiments; $X^3$ is from 2 to 5 amino acids in length, where at least two amino acids are independently selected from arginine, lysine, and/or a natural or non-natural amino acid having a side chain capable of forming an amide bond.

In some embodiments, $X^2$ is from 2 to 5 amino acids, where each amino acid is selected from glycine and/or serine. In some embodiments; $X^3$ is from 2 to 5 amino acids, where each amino acid is selected from glycine and/or serine.

In some embodiments, the total number of amino acid residues in $X^2$, $X^3$, and/or L is 6 or more. In some embodiments, the total number of amino acid residues in $X^2$, $X^3$, and/or L is 8 or more. In some embodiments, the total number of amino acid residues in $X^2$, $X^3$, and/or L is from 6 to 15.

In some embodiments, L comprises the amino acid sequence GSGSGSRR (SEQ ID NO: 4). Accordingly, in certain embodiments, provided is an amino acid comprising the amino acid sequence GSGSGSRR (SEQ ID NO: 4).

In some embodiments, L comprises the amino acid sequence GSGSRRGS (SEQ ID NO: 132). Accordingly, in certain embodiments, provided is an amino acid comprising the amino acid sequence GSGSRRGS (SEQ ID NO: 132).

In some embodiments, L is an amino acid sequence selected from the group comprising GSGRR (SEQ ID NO: 111), GSGSGRR (SEQ ID NO: 112), GSGSGSRR (SEQ ID NO: 4), GSGSGSGRR (SEQ ID NO: 113), GSGSGSGSRR (SEQ ID NO: 114), GSGSGSGSGSRR (SEQ ID NO: 115), GSGSGSGSGSGSRR (SEQ ID NO: 116), GSGSGSGSGSGSGRR (SEQ ID NO: 117), GSRRGS (SEQ ID NO: 118), GSGRRGSG (SEQ ID NO: 119), GSGRRRGSG (SEQ ID NO: 120), GSGRRR (SEQ ID NO: 121), GSGRRRR (SEQ ID NO: 122), GSGSGSRRR (SEQ ID NO: 123), GSGSGSRRRR (SEQ ID NO: 124), GSGSGSRRRRR (SEQ ID NO: 125), GSGSGSRRRRRR (SEQ ID NO: 126), and GSGSGSGSRRR (SEQ ID NO: 127).

Also provided herein is a bioconjugate comprising a glycan and at least one binding unit of formula $X^1$-GSGSGSRR (spacer disclosed as SEQ ID NO: 4), where $X^1$ is an amino acid sequence comprising a collagen-binding unit covalently bonded thereto.

Also provided herein is a bioconjugate comprising a glycan and at least one binding unit of formula $X^1$-GSGSGSRR—NHNH— (spacer disclosed as SEQ ID NO: 4), where $X^1$ is an amino acid sequence comprising a collagen-binding unit covalently bonded thereto.

Also provided herein is a bioconjugate comprising a glycan and at least one binding unit of formula $X^1$-GSGSGSRR (spacer disclosed as SEQ ID NO: 4), where $X^1$ is an amino acid sequence comprising a collagen-binding unit covalently bonded thereto.

Also provided herein is a bioconjugate comprising a glycan and at least one binding unit of formula $X^1$-GSGSGSRR—NHNH— (spacer disclosed as SEQ ID NO: 4), where $X^1$ is an amino acid sequence comprising a collagen-binding unit covalently bonded thereto.

Also provided herein is a bioconjugate comprising a glycan and a collagen-binding unit as described herein, wherein L is a spacer of from 5 to 20 amino acids selected from the group consisting glycine (G), serine (S), arginine (R), and lysine (K), a moiety

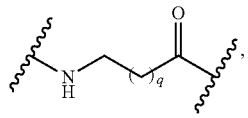

or a positively charged moiety, provided L comprises at least two positively charged moieties within the first five amino acids from the glycan, and wherein L further comprises an optional linking moiety which covalently bonds the peptide to the glycan.

In certain embodiments, the peptide comprises an amino acid sequence $X^1$, which includes a collagen-binding unit and at least one of $X^2$, $X^3$, and L to control the number and arrangement of the binding units within the peptide (e.g., being linear or branched) and the distance between each binding unit and an amino acid for conjugation to a glycan.

In certain embodiments, formula (I) comprises a —C(O)—NH—NH—C(O)— (i.e. a hydrazide-carbonyl) linkage to the glycan. In certain embodiments, L comprises a hydrazide. The —C(O)—NH—NH—C(O)— may include a carbonyl —C(O)— group from an amino acid of L and/or a carbonyl —C(O)— group from the glycan.

In certain embodiments, the peptides are bound to glycans, such as dermatan sulfate, by utilizing oxidation chemistry to cleave one or more of the saccharide ring within the glycan backbone in order to provide aldehyde binding sites on the glycan. The aldehyde binding sites were then used to conjugate the peptides (e.g., via a —C(O)—NH—N=C bond).

In certain embodiments, the peptides are bound to the glycan via a hydrazide-carbonyl linkage, where a carbonyl group of the hydrazide-carbonyl is an exocyclic carbonyl group present on the glycan. The exocyclic carbonyl group may be present on the native glycan, or alternatively, the glycan can be modified to include such a functional group. Such methods are further detailed below. It is contemplated that the beneficial effects exhibited by the bioconjugates bound in this way (such as increased binding affinity) is at least partially due to the glycan not containing oxidatively cleaved saccharide rings.

In certain embodiments, the bioconjugate can comprise a polymer backbone (e.g., a biocompatible polymer other than glycan), comprised of any single or combination of monomeric units, provided there are at least one, and in some instances, between 1 and about 50, suitable functional groups present thereon, such that the peptide(s) as described herein can be covalently bound thereto. The polymer can be linear, branched, or can contain side chains (e.g., other than the 1 to 50 peptides). The polymers can be neutral, cationic, anionic, or Zwitterionic. In certain embodiments, the polymer is a glycopolymer. The polymer can be a copolymer, including a block copolymer of the formula A-B-A, for example. Methods for providing such polymers are known in the art, and include for example, living polymerizations. In one embodiment, the polymer is a poly(ethylene glycol) (PEG). In another embodiment, the polymer is not a poly(ethylene glycol) (PEG). In certain embodiments, the polymer is not a glycan or a nanoparticle. In certain embodiments, the polymer is a glycan.

In certain embodiments of the bioconjugates described herein, the glycan can be alginate, chondroitin, dermatan, dermatan sulfate, heparan, heparan sulfate, heparin, dextran, dextran sulfate, or hyaluronan. In one embodiment, the glycan is dermatan sulfate. In one embodiment, the glycan is not dermatan sulfate. In another embodiment, the glycan is chondroitin sulfate. In another embodiment, the glycan is heparin. Various molecular weights for the heparin can be used in the bioconjugates described herein, such as from a single disaccharide unit of about 650-700 Da, to a glycan of about 50 kDa. In some embodiments, the heparin is from about 10 to about 20 kDa. In some embodiments, the heparin is up to about 15, or about 16, or about 17, or about 18, or about 19, or about 20 kDa.

In one embodiment, the bioconjugate comprises a peptide having a collagen-binding unit which binds to one or more of collagen type I, II, III, IV, V, VI, VII, VIII, IX, X, XI, XII, XIII, or XIV. In one embodiment, the collagen-binding unit promotes or inhibits fibrillogenesis upon binding to collagen. In one embodiment, the collagen-binding unit does not promote or inhibit fibrillogenesis upon binding to collagen. In some embodiments, the peptide binds to type I collagen. In other embodiments, the peptide binds to type IV collagen. In certain embodiments, one or more peptide(s) having a specified binding affinity for collagen can be used in the bioconjugates described herein. For example, the synthetic bioconjugates can comprise at least one peptide which has binding affinity to type I collagen and at least one peptide which has binding affinity to type IV collagen. In another embodiment, the peptides have binding affinity to type I collagen. In another embodiment, the peptides have binding affinity to type IV collagen. In certain embodiments, the peptides have binding affinity to type II collagen. In certain embodiments, the peptides have binding affinity to type III collagen. In certain embodiments, the peptide binds to more than one type of collagen, where the relative affinity to each collagen type may vary. In one embodiment, the collagen-binding unit binds to collagen with a dissociation constant ($K_d$) of less than about 1 mM, or less than about 900 μM, or less than about 800 μM, or less than about 700 μM, or less than about 600 μM, or less than about 500 μM, or less than about 400 μM, or less than about 300 μM, or less than about 200 μM, or less than about 100 μM.

Depending on the desired properties of the bioconjugate, the total number of binding units bonded to the glycan can be varied. In certain embodiments, the total number of binding units present in the bioconjugate is from about 1 to about 50, or from about 1 to about 40, or from about 1 to about 30, or from about 1 to about 25, or from about 2 to about 30, or from about 2 to about 25, or from about 3 to about 25, or from about 4 to about 25, or from about 5 to about 25, or from about 5 to about 30, or from about 1 to about 25, or from about 2 to about 25, or from about 11 to about 14, or from about 1 to about 8, or from about 1 to about 5, or about 1, or about 2, or about 3, or about 4, or about 5, or about 6, or about 7, or about 8 binding units. In some embodiments, the bioconjugate comprises from about 10 to about 40 binding units. In other embodiments, the bioconjugate comprises from about 5 to about 30 binding units. In certain embodiments, the bioconjugate comprises less than about 20 binding units. In certain embodiments, the bioconjugate comprises less than about 18 binding units. In various embodiments, the bioconjugate comprises from about 4 to about 18 binding units. In certain embodiments, the bioconjugate comprises less than about 15 binding units. In certain embodiments, the bioconjugate comprises less than about 10 binding units. In certain embodiments, the bioconjugate comprises less than about 30 binding units. In certain embodiments, the bioconjugate comprises about 25 binding units. In certain embodiments, the bioconjugate comprises from about 5 to about 40, or from about 10 to about 40, or from about 5 to about 20, or from about 4 to about 18, or about 10, or about 11, or about 18, or about 20 binding units, or about 25 binding units, or about 30 binding units, or about 40 binding units, or about 50 binding units. In certain embodiments, the bioconjugate comprises about 2 binding units, about 4 binding units, or about 8 binding units.

The binding units as described herein may further comprise a hydrazide moiety for conjugation to the glycan. The hydrazide group can be bound to the binding units at any suitable point of attachment, such as for example, the C-terminus, the N-terminus or via a side chain on an amino acid. For example, when a binding units is bound to the glycan via a side chain of an amino acid of the binding unit, the side chain is glutamic acid or aspartic acid. The hydrazide can be formed between a hydrazine (—NHNH$_2$) bound to a carbonyl group present on an amino acid in the peptide sequence (e.g., a C-terminal carbonyl group).

In certain embodiments, a bioconjugate comprising a glycan covalently bonded to a binding unit of formula (I)

$$((X^1)_m X^2)X^3\text{-}L \tag{I}$$

where $X^1$ and L are as defined herein, includes amino acid sequences $X^2$ and/or $X^3$ comprising from 2 to about 5 amino acids selected from the group consisting of glycine (G), serine (S), arginine (R), lysine (K), and a natural or non-natural amino acid having a side chain capable of forming an amide bond. For example, $X^2$ and/or $X^3$ may comprise an amino acid sequence such as GS, GSG, GSGS (SEQ ID NO: 67), RG, RGS, RGSG (SEQ ID NO: 68), RGSGS (SEQ ID NO: 69), RR, RRG, RRS, RRGS (SEQ ID NO: 70), RRGSG (SEQ ID NO: 71), RRGSGS (SEQ ID NO: 72), RGR, RSR, RRR, and the like.

In certain embodiments, $X^2$ and/or $X^3$ are amino acid sequences comprising more than one binding site (may be linear or branched) such that more than one peptide sequence can be bound thereto, thus creating a branched construct. In addition, since the peptide can be bound to the glycan via a terminal or non-terminal amino acid moiety, the peptide will be branched when bound to the glycan via a non-terminal amino acid moiety. The binding sites can be the same or different, and can be any suitable binding site, such as an amine or carboxylic acid moiety, such that a desired peptide sequence can be bound thereto (e.g. via an amide bond). Thus in certain embodiments, at least one of $X^2$ and/or $X^3$ contains one or more lysine, glutamic acid or aspartic acid residues. For example, $X^2$ and/or $X^3$ amino acid sequence such as KGSG (SEQ ID NO: 73), KKGSG (SEQ ID NO: 74), or KKKGSG (SEQ ID NO: 75), etc., providing 2, 3, or 4 binding sites, respectively.

In certain embodiments, $X^2$ and/or $X^3$ comprise one or more amino acids which contain a side chain capable of linking additional peptides or collagen-binding units. Exemplary amino acids for including in such spacers include, but are not limited to, lysine, glutamic acid, aspartic acid, etc. In certain embodiments, the $X^2$ and/or $X^3$ comprises one or more amino acid sequences of the formula KXX, where each X is independently a natural or unnatural amino acid. Specific examples of amino acid sequences which can be used alone or in combination to make branched constructs include, but are not limited to, KRR, KKK, $(K)_n$GSG (SEQ ID NO: 76), and $(KRR)_n$-KGSG (core peptide disclosed as SEQ ID NO: 73), where n is 0 to 5, or 1, 2, 3, 4, or 5.

A schematic of $X^2$ and/or $X^3$ is shown in the table below.

| Amino Acid Sequence | Number of peptides (i.e., binding sites) | Structure of Amino Acid Sequence |
|---|---|---|
| KGSG (SEQ ID NO: 73) | 2 | 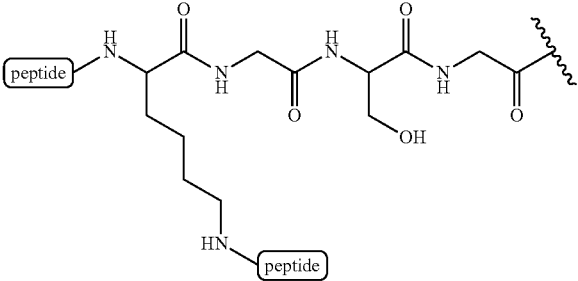 [SMILES: *C(=O)CNC(=O)C(CO)NC(=O)CNC(=O)C(CCCCNC)NC] |
| KKGSG (SEQ ID NO: 74) | 3 | 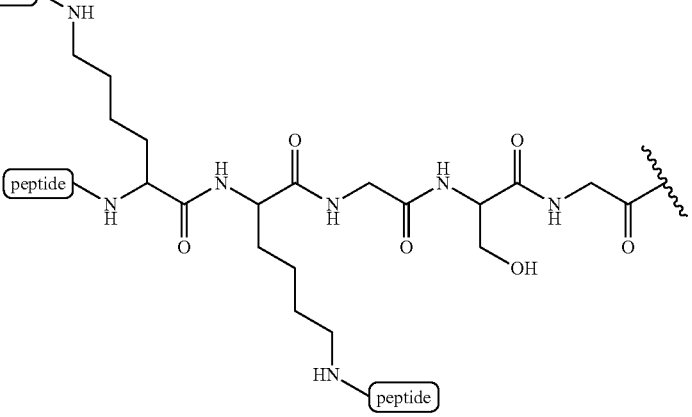 |
| KKKGSG (SEQ ID NO: 75) | 4 | 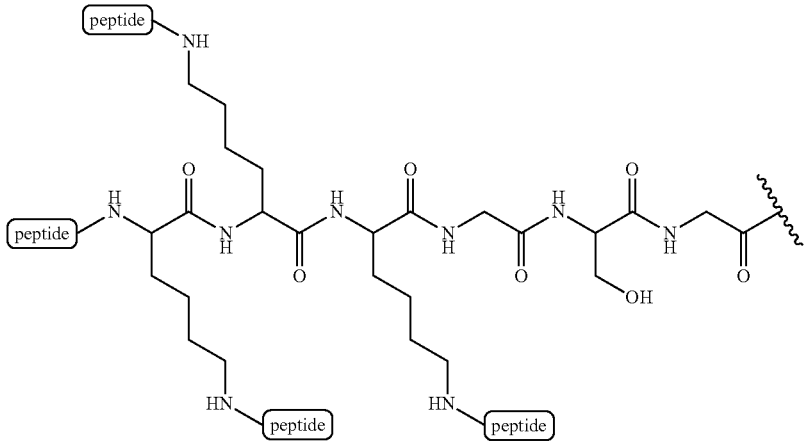 [SMILES: *C(=O)CNC(=O)C(CO)NC(=O)CNC(=O)C(CCCCNC)NC(=O)C(CCCCNC)NC(=O)C(CCCCNC)NC] |

-continued

| Amino Acid Sequence | Number of peptides (i.e., binding sites) | Structure of Amino Acid Sequence |
|---|---|---|
| K₂KGSG (SEQ ID NO: 74) | 4 | (branched peptide structure with four "peptide" groups attached to a K₂KGSG backbone) |

In certain embodiments, the hydrazide group is bonded to the peptide(s) N-terminus. In certain embodiments, the hydrazide group is bonded to the peptide(s) C-terminus. In certain embodiments, the hydrazide group is bonded to a side chain of an amino acid in the peptide(s), such as a glutamic acid and/or aspartic acid.

In any of the embodiments described herein, the number of peptides per glycan is an average, where certain bioconjugates in a composition may have more peptides per glycan and certain bioconjugates have less peptides per glycan. Accordingly, in certain embodiments, the number of peptides as described herein is an average in a composition of bioconjugates. For example, in certain embodiments, the bioconjugates are a composition where the average number of peptides per glycan is about 5. In other embodiments, the average number of peptides per glycan is about 6, or about 7, or about 8, or about 9, or about 10, or about 11, or about 12, or about 13, or about 14, or about 15, or about 16, or about 17, or about 18, or about 19, or about 20, or about 25, or about 30.

In certain embodiments, the number of peptides per glycan may be described as a "percent (%) functionalization" based on the percent of disaccharide units which are functionalized with peptide on the glycan backbone. For example, the total number of available disaccharide units present on the glycan can be calculated by dividing the molecular weight (or the average molecular weight) of the glycan (e.g., about 25 kDa up to about 70 kDa, or even about 100 kDa) by the molecular weight a single disaccharide unit (e.g., about 550-800 Da, or from about 650-750 Da). In embodiments where the glycan does not contain conventional "disaccharide units" (e.g., alginic acid), the total number of available disaccharide units present on the glycan to be used in the calculations presented herein, can be calculated by dividing the molecular weight (or the average molecular weight) of the glycan by the molecular weight of a single saccharide unit, and multiplying by 2.

In some embodiments, the number of available disaccharide units present on the glycan is from about 10 to about 80, or from about 10 to about 70, or from about 15 to about 70, or from about 20 to about 70, or from about 30 to about 70, or from about 35 to about 70, or from about 40 to about 70, or from about 10 to about 75, or from about 15 to about 75, or from about 20 to about 75, or from about 30 to about 75, or from about 35 to about 75, or from about 40 to about 75, or from about 10 to about 50, or from about 20 to about 50, or from about 25 to about 50, or from about 10 to about 35, or from about 15 to about 35, or from about 20 to about 35, or from about 10 to about 30, or from about 15 to about 30, or from about 20 to about 30, or about 15, or about 20, or about 25, or about 30, or about 35, or about 40, or about 45, or about 50, or about 55, or about 60, or about 65, or about 70.

Therefore, in certain embodiments, the glycan comprises from about 1 to about 50, or from about 5 to about 40% functionalization, or from about 5 to about 30% functionalization, or from about 1 to about 15% functionalization, or from about 1 to about 5% functionalization, or from about 5 to about 15% functionalization, or from about 10 to about 25% functionalization, or from about 25 to about 40% functionalization, or about 32% functionalization, or about 25% functionalization, or about 16% functionalization, or about 10% functionalization, or about 8% functionalization, or about 5% functionalization, or about 2.5% functionalization, wherein the percent (%) functionalization is determined by a percent of disaccharide units on the glycan which are functionalized with peptide. In some embodiments, the percent (%) functionalization of the glycan is from about 1% to about 50%, or from about 3% to about 40%, or from about 5% to about 30%, or from about 10% to about 20%, or about 1%, or about 2%, or about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95%, or about 100%.

In certain embodiments, the glycan is functionalized with a branched peptide. In some embodiments the peptide has from 2 to 4 branches. Therefore, in certain embodiments, the glycan comprises from about 1 to about 50% functionalizations, or from about 5 to about 40% functionalization, or from about 5 to about 30% functionalization, or from about 1 to about 15% functionalization, or from about 1 to about 5% functionalization, or from about 5 to about 15% functionalization, or from about 10 to about 25% functionalization, or from about 25 to about 40% functionalization, or about 2.5% functionalization, or about 5% functionalization, or about 8% functionalization, or about 10% functionalization or about 16% functionalization, or about 32% functionalization, wherein the percent (%) functionalization is determined by a percent of disaccharide units on the glycan which are functionalized with peptide.

In certain embodiments, provided is a composition comprising a bioconjugate as described herein and peptide, where the peptide is closely associated (e.g., via ionic bonding) to the bioconjugate. In certain embodiments, a bioconjugate aggregate may be formed thereby. It is contemplated that the bioconjugate aggregate (comprising bioconjugate and non-covalently bound peptide) may comprise from 1% to 200% functionalization (determined by a percent of disaccharide units on the glycan which are functionalized with peptide). In some embodiments, the percent (%) functionalization of the bioconjugate is from about 1% to about 50%, or from about 3% to about 40%, or from about 5% to about 30%, or from about 10% to about 20%, or about 1%, or about 2%, or about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95%, or about 100%.

It is contemplated that any glycan can be utilized in the various embodiments described herein, including, but not limited to, alginate, agarose, dextran, dextran sulfate, chondroitin, chondroitin sulfate (CS), dermatan, dermatan sulfate (DS), heparan sulfate, heparin (Hep), keratin, keratan sulfate, and hyaluronic acid (HA). The glycan can be naturally occurring or chemically derivatized, such as, but not limited to, partially N-desulfated derivatives, partially O-desulfated derivatives, and/or partially O-carboxymethylated derivatives.

In some embodiments, the glycan is unmodified. In certain embodiments, the glycan does not contain oxidatively cleaved saccharide rings and thus does not contain aldehyde functional groups. It is contemplated that the beneficial effects exhibited by the bioconjugates as disclosed herein may be at least partially be attributed to the glycan not containing oxidatively cleaved saccharide rings.

Such a linkage can result from coupling a hydrazide group on the peptide and a carbonyl group (e.g., a carboxylic acid group, or activated derivative thereof) on the glycan, or alternatively, a hydrazide group on the glycan and a carbonyl group (e.g., a carboxylic acid group, or activated derivative thereof) on the peptide. In certain embodiments, the hydrazide-carbonyl linkage is between a terminal hydrazide group on the peptide(s) and a carbonyl group on the glycan.

In one embodiment, the glycan is heparin, where the heparin may include heparin derivatives, such as, but not limited to partially N- and/or partially O-desulfated heparin derivatives, partially O-carboxymethylated heparin derivatives, or a combination thereof. In certain embodiments, the heparin is non-oxidized heparin (i.e., does not contain oxidatively cleaved saccharide rings) and does not contain aldehyde functional groups. Heparin derivatives and/or methods for providing heparin derivatives, such as partially N-desulfated heparin and/or partially O-desulfated heparin (i.e., 2-O and/or 6-O-desulfated heparin) are known in the art (see, e.g., Kariya et al., J. Biol. Chem., 2000, 275:25949-5958; Lapierre, et al. Glycobiology, 1996, 6(3):355-366). It is also contemplated that partially O-carboxymethylated heparin (or any glycan) derivatives, such as those which could be prepared according to Prestwich, et al. (US 2012/0142907; US 2010/0330143), can be used to provide the bioconjugates disclosed herein.

In certain embodiments, the molecular weight of the glycan is varied to tailor the effects of the bioconjugate (see e.g., Radek, K. A., et al., Wound Repair Regen., 2009, 17: 118-126; and Taylor, K. R., et al., J. Biol. Chem., 2005, 280:5300-5306). In another embodiment, the glycan is degraded by oxidation and alkaline elimination (see e.g., Fransson, L. A., et al., Eur. J. Biochem., 1980, 106:59-69) to afford degraded glycan having a lower molecular weight (e.g., from about 10 kDa to about 50 kDa).

In one embodiment, the glycan is dermatan sulfate (DS). The biological functions of DS is extensive, and includes the binding and activation of growth factors FGF-2, FGF-7, and FGF-10, which promote endothelial cell and keratinocyte proliferation and migration. In some embodiments, the weight range of the dermatan sulfate is from about 10 kDa to about 70 kDa. In one embodiment, the molecular weight of the dermatan sulfate is about 46 kDa. In another embodiment, the dermatan sulfate is degraded by oxidation and alkaline elimination (see e.g., Fransson, L. A., et al., Eur. J. Biochem., 1980, 106:59-69) to afford degraded dermatan sulfate having a low molecular weight (e.g., about 10 kDa).

In another embodiment, the glycan is heparin. Various molecular weights for the heparin can be used in the bioconjugates described herein, such as from a single disaccharide unit of about 650-700 Da to about 50 kDa. In some embodiments, the heparin is from about 10 to about 20 kDa. In some embodiments, the heparin is up to about 15, or about 16, or about 17, or about 18, or about 19, or about 20 kDa. In certain embodiments, the heparin may be oxidized under conditions that do not cleave one or more of the saccharide rings (see, e.g., Wang, et al. Biomacromolecules 2013, 14(7):2427-2432).

In one embodiment, the bioconjugate comprises a glycan and from about 5 to about 10, or about 5, binding units, wherein the binding units comprise at least one sequence of RRANAALKAGELYKSILY (SEQ ID NO: 9) or RRA-NAALKAGELYKSILYGSG (SEQ ID NO: 77), and are bound to the glycan via a hydrazide-carbonyl linkage. The binding units can be within the same or different peptides. In certain embodiments, the hydrazide-carbonyl linkage is between a terminal hydrazide group on the peptides and a carbonyl group on the glycan. In one embodiment, the glycan is heparin. In certain embodiments, the heparin does not contain oxidatively cleaved saccharide rings and thus does not contain aldehyde functional groups.

In one embodiment, the bioconjugate comprises a glycan and from about 5 to about 10, or about 8, or about 5, binding units, wherein the binding units comprise at least one sequence of GQLYKSILY (SEQ ID NO: 5), and are bound to the glycan via a hydrazide-carbonyl linkage. In one embodiment, the bioconjugate comprises a glycan and from about 5 to about 10, or about 8, or about 5, binding units, wherein the binding units comprise at least one sequence of GQLYKSILYGSGSGSRR (SEQ ID NO: 6), and are bound to the glycan via a hydrazide-carbonyl linkage. In one embodiment, the bioconjugate comprises a glycan and from about 5 to about 10, or about 8, or about 5, binding units, wherein the binding units comprise at least one sequence of GQLYKSILYGSGSGSRR—NHNH— (SEQ ID NO: 6), and are bound to the glycan via a hydrazide-carbonyl linkage. In certain embodiments, the hydrazide-carbonyl linkage is between a terminal hydrazide group on the binding units and a carbonyl group on the glycan. In one embodiment, the glycan is heparin. In certain embodiments, the heparin does not contain oxidatively cleaved saccharide rings and thus does not contain aldehyde functional groups.

Figure 17:
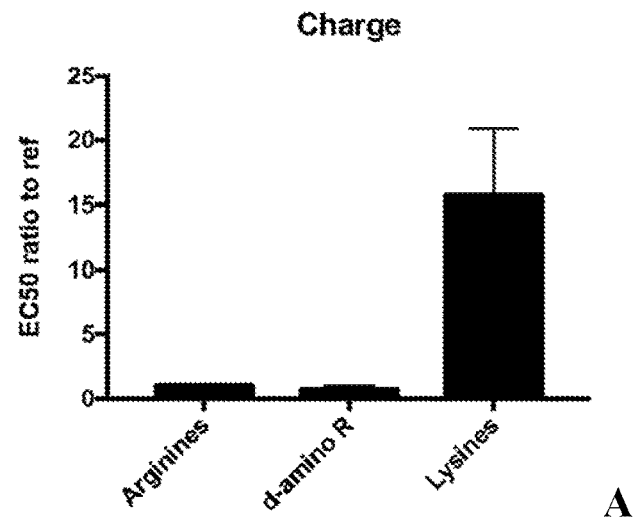
FIG. 17 shows the effect of amino acid sequence changes on collagen binding in GQLYKSILY (SEQ ID NO: 5) collagen binding domain. (A) shows effects of replacement of Arginine residues with Lysine or D-Arginine. (B) shows the collagen binding affinity of the GSGSGSRR (SEQ ID NO: 4) spacer compared to GQLYKSILYGSGSGSRR (SEQ ID NO: 6). Figure discloses "GQLY" as SEQ ID NO: 131. (C) shows the effect of inserting specific sequences or chemicals within the spacer. PAPAPRR (SEQ ID NO: 7) is Proline-Alanine-Proline-Alanine-Proline-Arginine-Arginine (SEQ ID NO: 7), AhxRR is 6-aminohexanoic acid-Arginine-Arginine, PEG6RR is (polyethylene glycol)$_6$-Arginine-Arginine, ahxRRAhx is 6-aminohexanoic acid-Arginine-Arginine-6-aminohexanoic acid.
Figure 17:
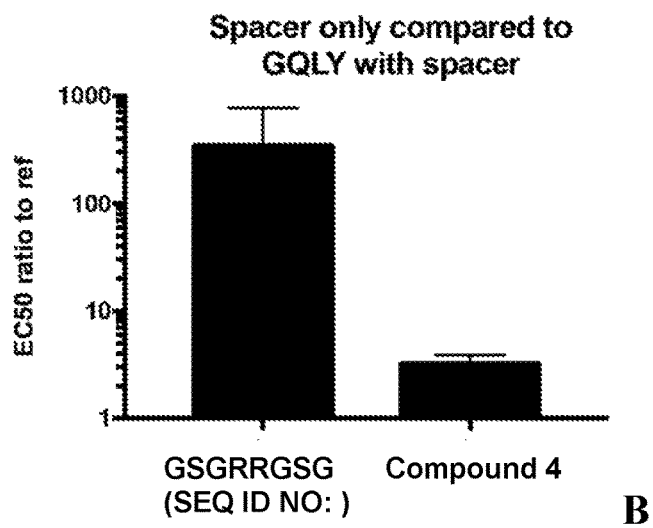
Figure 17:
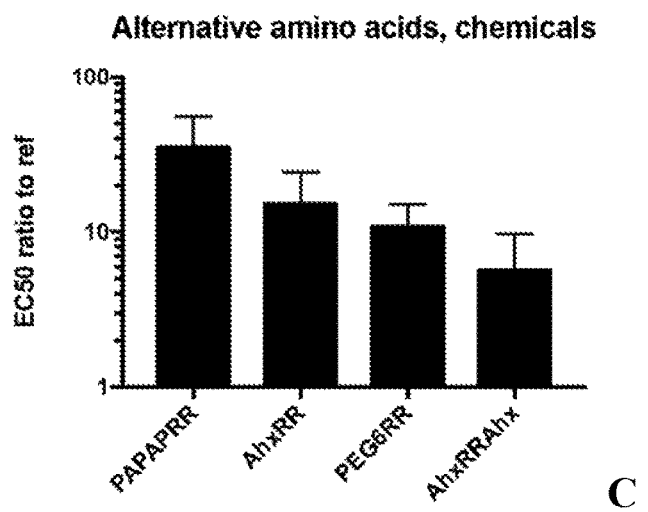

It has been found that the addition of amino acids to the C-terminus of the collagen binding unit GQLYKSILY (SEQ ID NO: 5) positively correlates with increased binding affinity (FIG. 17). It is contemplated that increasing the distance between the glycan and the binding site may reduce steric hinderance between the regions of the bound complex. Once the spacer reaches a sufficient length to reduce steric repulsions between regions of the bound complex there may be a diminishing effect to increasing the spacer further. Increasing spacer length beyond this threshold may even decrease avidity.

Figure 15:
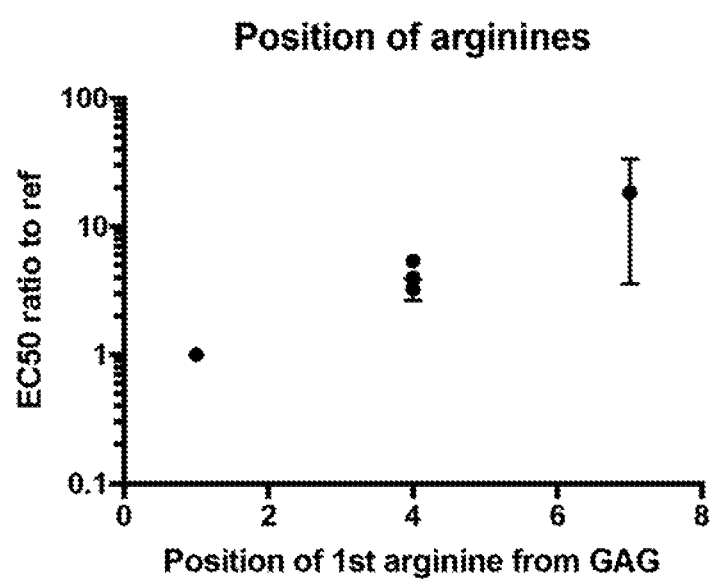
FIG. 15 shows the effect of placement of the first arginine residue from glycan (GAG) on collagen binding sequence GQLYKSILY (SEQ ID NO: 5).

The placement of arginine residues in the spacer sequence also affects the binding affinity, as shown by FIG. 15. Positioning a first arginine closer to the glycan backbone increases binding affinity. This may be due to the positive charge shielding the binding site from the negatively charged backbone.

In some embodiments, the collagen binding unit comprises the sequence GQLYKSILY (SEQ ID NO: 5), wherein one amino acid is substituted by a synthetic or naturally occurring D- or L-amino acid residue. In some embodiments, the collagen binding unit comprises the sequence XQLYKSILY (SEQ ID NO: 78); GXLYKSILY (SEQ ID NO: 79); GQXYKSILY (SEQ ID NO: 80); GQLXKSILY (SEQ ID NO: 81); GQLYXSILY (SEQ ID NO: 82); GQLYKXILY (SEQ ID NO: 83); GQLYKSXLY (SEQ ID NO: 84); GQLYKSILY (SEQ ID NO: 85); or GQLYKSILX (SEQ ID NO: 86), wherein X can be any amino acid residue, D or L. Each of these sequences may be followed with a spacer of any embodiment listed herein. In some embodiments, X is L-alanine. In some embodiments the spacer is GSGSGSRR (SEQ ID NO: 4).

In some embodiments, the binding unit and spacer comprises the sequence LKAGQLYKSILYHHLHSGSGSGSRR (SEQ ID NO: 87), KAGQLYKSILYHHLHSYGSGSGSRR (SEQ ID NO: 88), GQLYKSILYHHLHSYQNS-KPGSGSGSRR (SEQ ID NO: 89).

In some embodiments, the binding unit and spacer comprises the sequence GQLYKSILYGQLYKSILYGSGS-GSRR (SEQ ID NO: 90), GQLYKSILYGSGQLYKSI-LYGSGSGSRR (SEQ ID NO: 91), GQLYKSILY-Ahx-GQLYKSILYGSGSGSRR (SEQ ID NO: 92), or (GQLYKS-ILY)$_2$KGSGSGSRR (core peptide disclosed as SEQ ID NO: 5, linker disclosed as SEQ ID NO: 93).

2. Synthesis of Bioconjugates

The peptides as used herein may be purchased from a commercial source or partially or fully synthesized using methods well known in the art (e.g., chemical and/or biotechnological methods). In certain embodiments, the peptides are synthesized according to solid phase peptide synthesis protocols that are well known in the art. In another embodiment, the peptide is synthesized on a solid support according to the well-known Fmoc protocol, cleaved from the support with trifluoroacetic acid and purified by chromatography according to methods known to persons skilled in the art. In other embodiments, the peptide is synthesized utilizing the methods of biotechnology that are well known to persons skilled in the art. In one embodiment, a DNA sequence that encodes the amino acid sequence information for the desired peptide is ligated by recombinant DNA techniques known to persons skilled in the art into an expression plasmid (for example, a plasmid that incorporates an affinity tag for affinity purification of the peptide), the plasmid is transfected into a host organism for expression, and the peptide is then isolated from the host organism or the growth medium, e.g., by affinity purification. Recombinant DNA technology methods are described in Sambrook et al., "Molecular Cloning: A Laboratory Manual", 3rd Edition, Cold Spring Harbor Laboratory Press, (2001), incorporated herein by reference, and are well-known to the skilled artisan.

As shown in Scheme 1, the peptides as described herein can be covalently bound to the glycan (e.g., heparin) 1A through a carboxylic acid moiety to provide a bioconjugate 1B as disclosed herein. As is typical in peptide coupling reactions, an activating agent may be used to facilitate the reaction. Suitable coupling agents (or activating agents) are known in the art and include for example, carbodiimides (e.g., N,N'-dicyclohexylcarbodiimide (DCC), N,N'-dicyclopentylcarbodiimide, N,N'-diisopropylcarbodiimide (DIC), 1-ethyl-3-(3-dimethylaminopropyl)carbodiimide (EDC), N-t-butyl-N-methylcarbodiimide (BMC), N-t-butyl-N-ethylcarbodiimide (BEC), 1,3-bis(2,2-dimethyl-1,3-dioxolan-4-ylmethyl)carbodiimide (BDDC), etc.), anhydrides (e.g., symmetric, mixed, or cyclic anhydrides), activated esters (e.g., phenyl activated ester derivatives, p-hydroxamic activated ester, hexafluoroacetone (HFA), etc.), acylazoles (acylimidazoles using CDI, acylbenzotriazoles, etc.), acyl azides, acid halides, phosphonium salts (HOBt, PyBOP, HOAt, etc), aminium/uronium salts (e.g., tetramethyl aminium salts, bispyrrolidino aminium salts, bispiperidino aminium salts, imidazolium uronium salts, pyrimidinium uronium salts, uronium salts derived from N,N,N'-trimethyl-N'-phenylurea, morpholino-based aminium/uronium coupling reagents, antimoniate uronium salts, etc.), organophosphorus reagents (e.g., phosphinic and phosphoric acid derivatives), organosulfur reagents (e.g., sulfonic acid derivatives), triazine coupling reagents (e.g., 2-chloro-4,6-dimethoxy-1,3,5-triazine, 4-(4,6-dimethoxy-1,3,5-triazin-2-yl)-4 methyl-morpholinium chloride, 4-(4,6-dimethoxy-1,3,5-triazin-2-yl)-4 methylmorpholinium tetrafluoroborate, etc.), pyridinium coupling reagents (e.g., Mukaiyama's reagent, pyridinium tetrafluoroborate coupling reagents, etc.), polymer-supported reagents (e.g., polymer-bound carbodiimide, polymer-bound TBTU, polymer-bound 2,4,6-trichloro-1,3,5-triazine, polymer-bound HOBt, polymer-bound HOSu, polymer-bound IIDQ, polymer-bound EEDQ, etc.), and the like (see, e.g., El-Faham, et al. Chem. Rev., 2011, 111(11): 6557-6602; Han, et al. Tetrahedron, 2004, 60:2447-2467).

In one embodiment, the peptide coupling reaction proceeds via an activated glycan intermediate by reacting a carboxylic acid moiety of the glycan with a coupling agent (e.g., a carbodiimide reagent, such as but not limited to, N,N'-dicyclohexylcarbodiimide (DCC), N,N'-diisopropylcarbodiimide (DIC), 1-ethyl-3-(3-dimethylaminopropyl) carbodiimide (EDC), etc.) to form an O-acylisourea intermediate. Such carbodiimide chemistry is well known in the art and suitable coupling agents can be purchased from commercial sources. Contacting the O-acylisourea intermediate with the desired peptide yields the bioconjugate. The glycan can be contacted with activating agent prior to, or in the presence of, the peptide. In some embodiments, the reaction is carried out in the presence of N-hydroxysuccinimide (NHS) or derivatives thereof. In certain embodiments, the peptide sequence can modified to include a reactive moiety (e.g., a hydrazide functional group) to aid in the coupling reaction with the glycan, or O-acylisourea intermediate thereof. In addition, in certain instances where one or more amino acids in the peptides contain reactive functional groups (e.g., carboxylic acid side chains), standard protecting group chemistry may be used to protect one or more side chains facilitate the coupling reaction. In addition, non-amino acid spacers may also be employed alone, or in combination with amino acid spacers (e.g., aminohexanoic acid).

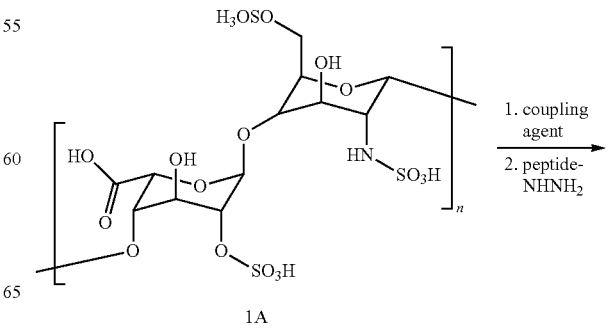

Scheme 1. Synthesis of Bioconjugates

1A

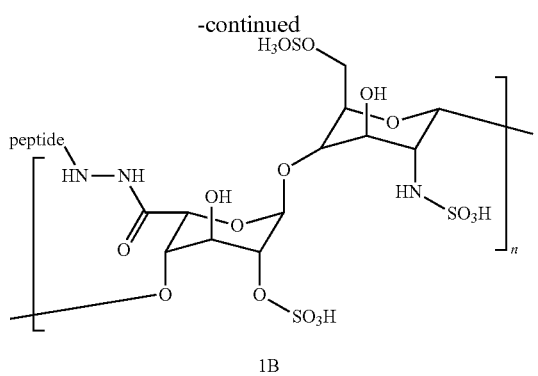

1B

In certain embodiments, the bioconjugates are derived from modified glycan derivatives (e.g., heparin) (Scheme 2). Various glycan derivatives suitable for use in the bioconjugates described herein are known in the art, such as partially N-desulfated heparin and partially O-desulfated heparin (i.e., 2-O and/or 6-O-desulfated heparin, see, e.g., Kariya et al., J. Biol. Chem., 2000, 275:25949-5958; Lapierre, et al. Glycobiology, 1996, 6(3):355-366). Exemplary methods are shown below in Scheme 2. As shown in Scheme 2, glycan (e.g., heparin) 1A can be reacted with a suitable desulfating agent, such as for example, a base (e.g., NaOH) or a silylating reagent (e.g., N,O-bis(trimethylsilyl)acetamide (BTSA), N-methyl-N-(trimethylsilyl)trifluoro acetamide (MTSTFA), etc.) to provide one or more desulfated glycan derivative(s) 2A. As is apparent to one of skill in the art, the glycan derivative 2A can be tailored depending on the reagents and reaction conditions employed, such that partial, complete or a mixture of desulfated glycan derivative(s) 2A can be obtained. The desulfated glycan derivative(s) 2A can then be reacted with peptide, optionally in the presence of a coupling agent, as described above for Scheme 1, under typical peptide coupling reaction conditions to provide bioconjugate 2B. In addition, as shown in Scheme 2, glycan derivatives having at least one hydroxyl group (e.g., 6-O-desulfated heparin) can be converted to an O-carboxymethylated glycan derivative(s) (e.g., 6-O— carboxymethylated heparin) 2C (see, e.g., Prestwich, et al. in US 2012/0142907 and US 2010/0330143). Reaction of 2C with peptide, optionally in the presence of a coupling agent as described above for Scheme 1 under typical peptide coupling reaction conditions can provide bioconjugates 2D and/or 2E.

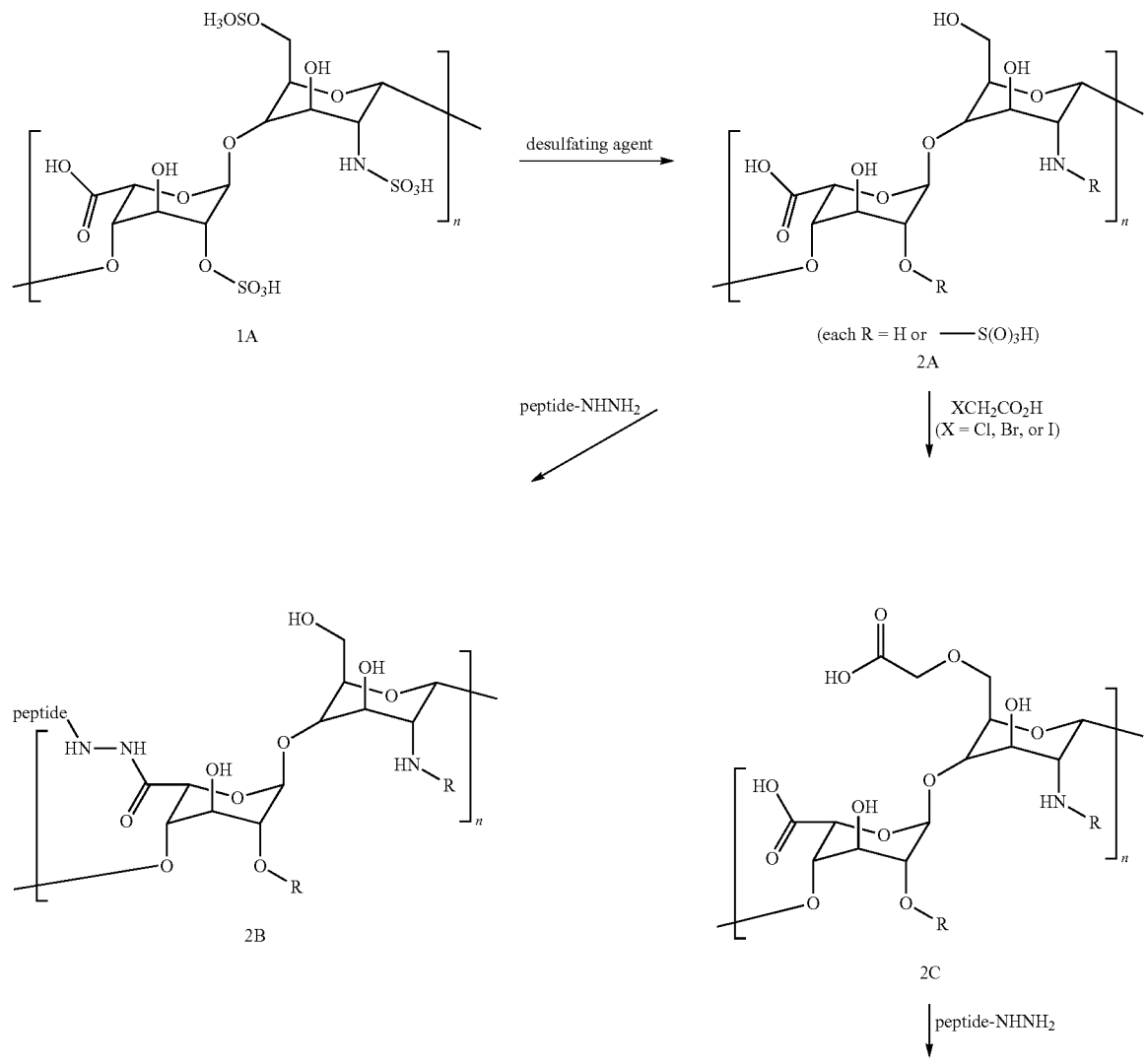

Scheme 2. Alternative Synthesis of Bioconjugates

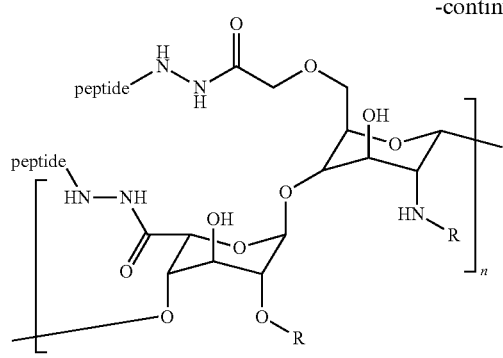

2D

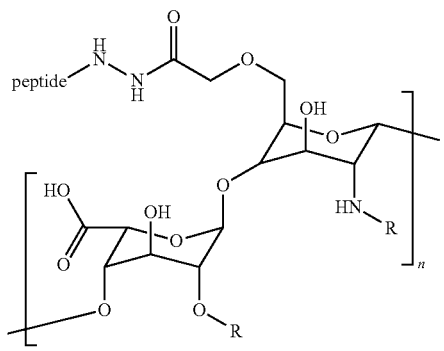

2E

In certain embodiments, the bioconjugates can be prepared according to Scheme 3. As shown in Scheme 3, the glycan (e.g., chondroitin sulfate "CS") is oxidized using a periodate reagent, such as sodium periodate, to provide aldehyde functional groups on the glycan (e.g., "ox-CS") for covalently bonding the peptides to the glycan. The peptides are then covalently bonded to the glycan (e.g., chondroitin sulfate "CS") by reacting an aldehyde function of the oxidized glycan (e.g., "ox-CS") with N-[β-maleimidopropionic acid]hydrazide (BMPH) to form a glycan intermediate (e.g., "BMPH-CS") and further reacting the glycan intermediate with peptides containing at least one free thiol group (i.e., —SH group) to yield the synthetic peptidoglycan.

Scheme 3. Synthesis of CS-BMPH-Peptide$_n$

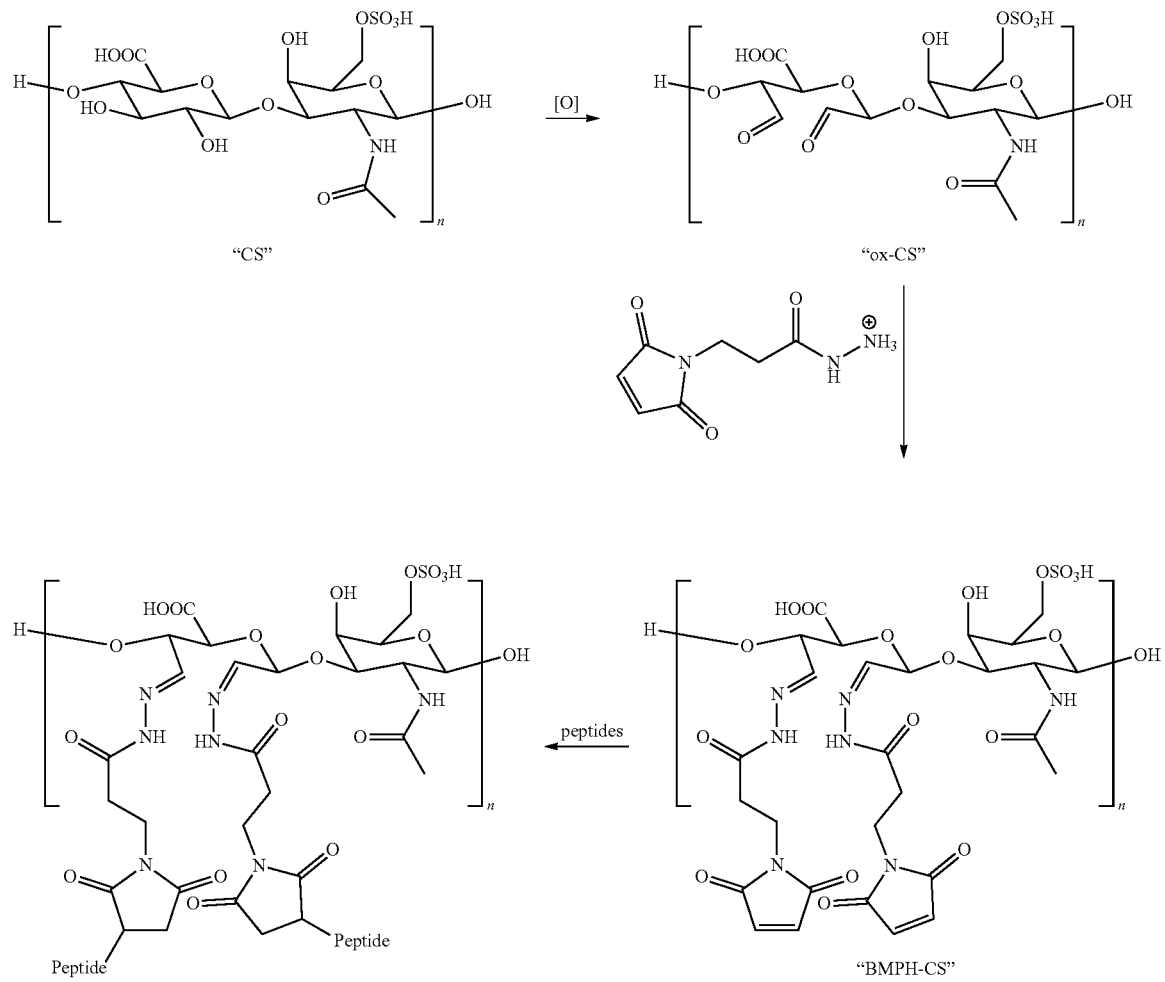

3. Methods of Use

3.1 Graft Failure

One embodiment of the present disclosure provides methods and associated compositions for improving the success rate and/or reducing failure of a surgical bypass procedure. Bypass grafts are used as one form of treatment of arterial blockage in both coronary artery disease (CAD) and peripheral artery disease (PAD). As used herein, the term "treating" refers to preventing, curing, reversing, attenuating, alleviating, minimizing, inhibiting, suppressing and/or halting one or more clinical symptoms of a disease or disorder. Approximately 500,000 coronary artery bypass graft (CABG) procedures and over 70,000 peripheral bypass graft procedures are performed annually in the US. Most commonly, an autologous vessel graft is harvested, often from the saphenous vein.

Despite the prevalence of surgical bypass with autologous vein grafts to restore blood flow, there are a large number of vein graft failures (VGF) in both CAD and PAD. In the periphery alone, vein graft failure rates reach levels of 50% failure within 5 years. While 5% to 10% of vein grafts fail shortly after implantation due to technical factors and acute thrombosis, mid-term failure (3 to 24 months) may occur in another 20% to 30% of cases and can lead to costly surveillance, reintervention procedures and amputation. The 12-month incidence of vein graft failure in CLI patients (n=1219) was 29% during a two-decade experience at the Brigham and Women's Hospital. The consequences of vein graft failure are often severe for the patient, including recurrent ischemic symptoms, debilitating surgery and limb loss. To date, pharmacotherapies and technical innovations have had little impact on reducing vein graft failure.

It is contemplated that injuries to the fragile endothelial layer of vein graft conduits, whether caused by vein graft harvesting, preservation media, excessive manipulation in preparation for bypass, or ischemia and reperfusion injury, result in a platelet mediated inflammatory response within the vessel wall after implantation. Such endothelial injuries and ECM-platelet activation cascade can result in early VGF via acute inflammation and thrombosis, or delayed VGF via neointimal hyperplasia. Limiting the exposure of the vein graft sub-endothelial matrix to circulating platelets after implantation, therefore, can help reduce acute vessel wall inflammation, improve re-epithelialization and limit excessive neointimal hyperplasia that may lead to vessel occlusion and VGF. The bioconjugate as described herein can be used as a vein graft preservation solution for patients with cardiovascular disease undergoing surgical bypass with autologous vein grafts. The bioconjugates, and compositions comprising the same, as described herein can be used to treat and/or prevent coronary artery disease and/or peripheral artery disease in a patient in need thereof.

In accordance with one embodiment of the present disclosure, therefore, provided is a method for preparing a vascular graft (e.g., a vein graft) by contacting the internal wall of a section of a blood vessel with a solution that contains a synthetic bioconjugate of the disclosure. One way of implementing the contact is to soak the section in the solution. Conditions for this contact can vary but can be readily determined, depending on the concentration of the synthetic bioconjugate and the characteristics of the blood vessel, such that there is a suitable amount of the synthetic bioconjugate bound to the internal wall. The vascular graft prepared with such a method is also within the scope of the present disclosure.

Once the graft is prepared, it can be implanted to a patient in need thereof. The surgical bypass procedure can be readily carried out by a medical professional. Once implanted, the synthetic bioconjugate bound to the internal wall of the grant can help reduce acute vessel wall inflammation, improve re-epithelialization of the graft and limit excessive neointimal hyperplasia of the graft, resulting in reduced graft failure.

In one embodiment, when the graft has been treated with a synthetic bioconjugate as described above, during or following the bypass procedure, a solution of the synthetic bioconjugate can be injected into the lumen of the graft such that the synthetic bioconjugate will bind to the internal wall of the graft. In one aspect, the injection is done before blood flow is restored or started through the graft. In another aspect, the injection is done shortly after (e.g., within 10 minutes, within 5 minutes, or within 1 minute) the blood flow is restored or started.

In some embodiments, the method is effective in inhibiting negative remodeling of the blood vessel. Coronary artery disease, also known as ischemic or coronary heart disease, occurs when part of the smooth, elastic lining inside a coronary artery (the arteries that supply blood to the heart muscle) develops atherosclerosis, effectively restricting blood flow to the heart. Peripheral arterial disease, also known as atherosclerosis or hardening of the arteries, is a disorder that occurs in the arteries of the circulatory system. Negative remodeling includes the physiologic or pathologic response of a blood vessel to a stimulus resulting in a reduction of vessel diameter and lumen diameter. Such a stimulus could be provided by, for example, a change in blood flow or an angioplasty procedure. In some embodiments, the injection of the bioconjugates described herein, and compositions comprising the same, leads to an increase of vessel diameter by about any of 10%, 20%, 30%, 40%, 60%, 70%, 80%, 95%, or more, compared to the diameter of a vessel of without the injection. Negative remodeling can be quantified, for example, angiographically as the percent diameter stenosis at the lesion site (or disease site). Another method of determining the degree of remodeling involves measuring in-lesion external elastic lamina area using intravascular ultrasound (IVUS). IVUS is a technique that can image the external elastic lamina as well as the vascular lumen. In some embodiments, the negative remodeling is associated with a vascular interventional procedure, such as angioplasty, stenting, or atherectomy. The bioconjugates, and compositions comprising the same, as described herein can therefore be injected before, during and/or after the vascular interventional procedure. In certain embodiments, provided is a method of treating stenosis, or occlusion within the femoropopliteal artery, in a patient in need thereof, comprising applying a solution to the internal wall of a lumen before, during and/or after a balloon angioplasty, wherein the solution comprises an effective amount of a bioconjugate as described herein or a composition comprising the same.

The present disclosure thus provides a method of inhibiting negative remodeling in a blood vessel (e.g., artery) in an individual in need thereof, comprising injecting into the blood vessel wall or tissue surrounding the blood vessel wall an effective amount of a bioconjugate as described herein or a composition comprising the same. In some embodiments, the bioconjugate or composition is injected at or adjacent to a site of potential or actual negative remodeling (such as no more than about 2, 1, or 0.5 cm away from the site). In some embodiments, the nanoparticle composition is injected remotely from a site of potential or actual negative remodeling (for example at least about any of 1, 2, 3, 4, 5, 6, 7, 8, 9, or 10 cm away from the site). In some embodiments, the injection is via a catheter with a needle. In some embodiments, the site is a coronary artery or a peripheral artery. In some embodiments, the artery is selected from the group consisting of renal artery, cerebral artery, pulmonary artery, and artery in the leg. In some embodiments, the artery is a balloon injured artery. Further examples, include, but are not limited to, abdominal aorta, anterior tibial artery, arch of aorta, arcuate artery, axillary artery, brachial artery, carotid artery, celiac artery, circumflex fibular artery, common hepatic artery, common iliac artery, deep femoral artery, deep palmar arterial arch, dorsal digital artery, dorsal metatarsal artery, external carotid artery, external iliac artery, facial artery, femoral artery, inferior mesenteric artery, internal iliac artery, intestinal artery, lateral inferior genicular artery, lateral superior genicular artery, palmar digital artery, peroneal artery, popliteal artery, posterior tibial artery, *profunda* femoris artery, pulmonary artery, radial artery, renal artery, splenic artery, subclavian artery, superficial palmar arterial arch, superior mesenteric artery, superior ulnar collateral artery, and/or ulnar artery. In certain embodiments, the artery is part of the coronary vasculature.

In one embodiment, the bioconjugate used in the methods described above comprises heparin and from about 5 to about 10, or about 5, peptides, wherein the peptides comprise at least one sequence of GQLYKSILYGSGSGSRR (SEQ ID NO: 6). In one embodiment, the bioconjugate used in the methods described above comprises heparin and from about 5 to about 10, or about 5, peptides, wherein the peptides comprise at least one sequence of GQLYKSILYGSGSGSRR (SEQ ID NO: 6), and are bound to the heparin via a hydrazide-carbonyl linkage.

3.2 Fibrosis

In one embodiment, provided herein are bioconjugates and methods for preventing and/or treating fibrosis. Fibrosis is an inflammatory disease in which inflammatory cells migrate into tissue and organs, leading to cellular responses that result in scarring. Fibrosis can occur in many tissues within the body, typically as a result of inflammation or damage. By preventing inflammatory cell extravasation, fibrosis can be attenuated or prevented.

In one embodiment, the bioconjugates and methods provided herein can be used to prevent and/or treat pulmonary fibrosis. In lungs, types of fibrosis include pulmonary fibrosis such as cystic fibrosis and idiopathic pulmonary fibrosis. Pulmonary fibrosis is a respiratory disease in which scars are formed in the lung tissues, leading to serious breathing problems. Scar formation leads to thickening of the walls, and causes reduced oxygen supply in the blood. As a consequence patients suffer from perpetual shortness of breath.

In one embodiment, the bioconjugates and methods provided herein can be used to treat liver fibrosis. Liver fibrosis may result from a wide variety of conditions including chronic alcohol exposure, hepatitis B virus (HBV) infection, non-alcoholic fatty liver disease (NAFLD), Nonalcoholic steatohepatitis (NASH), hepatitis C virus (HCV) infection, Wilson's disease, alpha-1-antitrypsin deficiency, hemochromatosis, primary biliary cirrhosis, primary sclerosing cholangitis, and autoimmune hepatitis. Chronic HCV is the leading contributor to chronic liver disease and the liver elicits a persistent inflammatory and fibrosis, which is characterized by the formation of fibrous tissue and scarring on the liver. NAFLD and NASH also cause inflammation and fibrosis in the liver.

Cirrhosis is fibrosis in the liver in which the liver does not function properly due to long-term damage. Typically, the disease comes on slowly over months or years. Early on, there are often no symptoms. As the disease worsens, a person may become tired, weak, itchy, have swelling in the lower legs, develop yellow skin, bruise easily, have fluid buildup in the abdomen, or develop spider-like blood vessels on the skin. The fluid build-up in the abdomen may become spontaneously infected. Other complications include hepatic encephalopathy, bleeding from dilated veins in the esophagus or dilated stomach veins, and liver cancer. Hepatic encephalopathy results in confusion and possibly unconsciousness. Cirrhosis can result in liver dysfunction. The following symptoms or features are direct consequences of liver dysfunction and thus can also be treated or ameliorated by the presently disclosed compositions and methods.

It has been shown that that direct interaction between hepatic stellate cells (HSCs) and tumor cells promotes tumor growth via multiple mechanisms. Therefore, targeting HSCs to lessen or eliminate their tumor-supporting role presents a potential therapeutic strategy to prevent, inhibit or treat hepatocellular carcinoma (HCC). In certain embodiments, provided is a method of preventing or inhibiting the development of hepatocellular carcinoma (HCC) in a patient in need thereof, comprising administering to the patient an effective amount of a bioconjugate as described herein. In certain embodiments, the development of hepatocellular carcinoma (HCC) is a result of liver cirrhosis. In certain embodiments, the method comprises inhibiting hepatic stellate cell proliferation and/or fibrotic phenotype transition. In certain embodiments, the bioconjugate is administered locally to the liver, such as during a transcatheter arterial chemoembolization (TACE) procedure.

Spider angiomas or spider nevi are vascular lesions consisting of a central arteriole surrounded by many smaller vessels and occur due to an increase in estradiol. Palmar erythema is a reddening of palms at the thenar and hypothenar eminences also as a result of increased estrogen. Gynecomastia, or increase in breast gland size in men that is not cancerous, is caused by increased estradiol and can occur in up to two thirds of patients. Hypogonadism, a decrease in sex hormones manifest as impotence, infertility, loss of sexual drive, and testicular atrophy, can result from primary gonadal injury or suppression of hypothalamic/pituitary function. Hypogonadism is associated with cirrhosis due to alcoholism and hemochromatosis. Liver size can be enlarged, normal, or shrunken in people with cirrhosis.

In one embodiment, the bioconjugates and methods provided herein can be used to prevent and/or treat renal fibrosis. Renal fibrosis can result from acute or sustained injury to the kidney. The injury can lead to excessive deposition of extracellular matrix. Over time, this can result in kidney failure, requiring patients to undergo dialysis or kidney transplant.

Ascites, accumulation of fluid in the peritoneal cavity, gives rise to flank dullness. This can be visible as increase in abdominal girth. Fetor hepaticus is a musty breath odor resulting from increased dimethyl sulfide. Jaundice is yellow discoloration of the skin and mucous membranes due to increased bilirubin. In addition, liver cirrhosis increases resistance to blood flow and higher pressure in the portal venous system, resulting in portal hypertension.

In one embodiment, the bioconjugates and methods provided herein can be used to prevent and/or treat fibrosis in the heart. Fibrosis in the heart is present in the form of atrial fibrosis, endomyocardial fibrosis, or myocardial infarction. Glial scar is fibrosis in the brain. Other types of fibrosis include, without limitation, arthrofibrosis (knee, shoulder, other joints), Crohn's disease (intestine), Dupuytren's contracture (hands, fingers), keloid (skin), mediastinal fibrosis (soft tissue of the mediastinum), myelofibrosis (bone marrow), Peyronie's disease (penis), nephrogenic systemic fibrosis (skin), progressive massive fibrosis (lungs), retroperitoneal fibrosis (soft tissue of the retroperitoneum), scleroderma/systemic sclerosis (skin, lungs), and some forms of adhesive capsulitis (shoulder).

It is contemplated that the compositions and methods of the present disclosure are suitable for preventing and/or treating any of these diseases or symptoms or features associated with these diseases. Development of fibrosis involves stimulated cells laying down connective tissue, including collagen and glycosaminoglycans. The bioconjugates of the present disclosure can interact with the collagen or glycosaminoglycans and thus disrupt the formation of such excessive connective tissue. The bioconjugates can also protect the endothelial barrier. This can be by interacting with exposed extracellular matrix due to microvascular injury. Protecting the endothelial barrier prevents inflammatory cells from extravating into the tissue to cause the excessive ECM deposition that leads to the fibrotic tissue. Accordingly, the bioconjugates can prevent, inhibit, delay, and/or reverse fibrosis.

In certain embodiments, the fibrosis is post ischemic, post infectious, or idiopathic (e.g., renal, hepatic, cardiac, pulmonary). See, e.g., Guerrot, D., et al. Fibrogenesis & tissue repair 5.Suppl 1 (2012): S15, and Yamaguchi, I., et al. Nephron Experimental Nephrology 120.1 (2012): e20-e31. In certain embodiments, the fibrosis is retroperitoneal. In certain embodiments, the fibrosis is dermal (e.g., scleroderma). See, e.g., Maurer, B., et al. Annals of the rheumatic diseases (2013): annrheumdis-2013.

In one embodiment, the disease is not acute tubular necrosis, diabetic chronic renal failure, lupus nephritis, renal fibrosis, or acute glomerulonephritis. In one embodiment, the disease is not idiopathic pulmonary fibrosis (IPF), chronic obstructive pulmonary disease, asthma, or emphysema.

In certain embodiments, the fibrosis is caused by, or otherwise related to, a lysosomal storage disorder, including but not limited to, Fabry disease, Gaucher disease, Niemann-Pick disease, and Hunter syndrome (mucopolysaccharidoses). Therefore, in certain embodiments, provided herein a method for preventing fibrosis caused by, or otherwise related to, a lysosomal storage disorder in a patient in need thereof.

In one embodiment, provided herein is a use of the bioconjugate(s) disclosed herein for the prevention or treatment of fibrosis. In one embodiment, provided herein is a use of the bioconjugate(s) disclosed herein for the preparation of a medicament for the prevention or treatment of fibrosis. In one embodiment, provided herein is a use of the bioconjugate(s) disclosed herein for the prevention or treatment of liver fibrosis. In one embodiment, provided herein is a use of the bioconjugate(s) disclosed herein for the prevention or treatment of pulmonary fibrosis. In one embodiment, the bioconjugate used in the methods described above comprises heparin and from about 5 to about 10, or about 5, peptides, wherein the peptides comprise at least one sequence of GQLYKSILYGSGSGSRR (SEQ ID NO: 6), or an amino acid sequence having one, two, or three amino additions, deletions and/or substitutions each therefrom. In one embodiment, the bioconjugate used in the methods described above comprises heparin and from about 5 to about 10, or about 5, peptides, wherein the peptides comprise at least one sequence of GQLYKSILYGSGSGSRR (SEQ ID NO: 6). In one embodiment, the peptide(s) are bond to the heparin or other glycan via a hydrazide-carbonyl linkage.

In one embodiment, provided herein is a method for preventing or treating liver fibrosis or pulmonary fibrosis in a patient in need thereof, comprising administering to the patient an effective amount of a bioconjugate comprising heparin and from about 5 to about 10, or about 5, peptides, wherein the peptides comprise at least one sequence of GQLYKSILYGSGSGSRR (SEQ ID NO: 6). In one embodiment, provided herein is a use of the bioconjugate(s) disclosed herein for the prevention or treatment of liver fibrosis or pulmonary fibrosis in a patient in need thereof. In one embodiment, an effective amount of the bioconjugate is administered.

Also provided herein are methods for preventing and/or treating vasculitis. Vasculitis is defined by inflammation of the blood-vessel wall and forms the pathological foundation of a diverse group of individual disease entities. Vasculitis is one of the intractable pathological conditions commonly observed in autoimmune diseases, and many cases thereof are refractory to conventionally-used therapeutic methods such as steroids and immunosuppressants. In the vasculitis syndrome, inflammation occurs in arteries of various sizes, and fever, pain in muscles and joints, vascular occlusion, skin ulcer, and mononeuritis multiplex may develop. The methods may be used to treat large vessel vasculitis (LVV), medium vessel vasculitis (MVV), small vessel vasculitis (SVV), variable vessel vasculitis (VVV), single-organ vasculitis (SOV), vasculitis associated with systemic disease, and/or vasculitis associated with probable etiology. Non-limiting examples of large vessel vasculitis (LVV) include takayasu arteritis (TAK) and giant cell arteritis (GCA). Non-limiting examples of medium vessel vasculitis (MVV) include polyarteritis nodosa (PAN) and kawasaki disease (KD). Non-limiting examples of small vessel vasculitis (SVV) include antineutrophil cytoplasmic antibody (ANCA)-associated vasculitis (AAV), microscopic polyangiitis (MPA), granulomatosis with polyangiitis (Wegener's) (GPA), eosinophilic granulomatosis with polyangiitis (Churg-Strauss) (EGPA), immune complex SVV, anti-glomerular basement membrane (anti-GBM) disease, gryoglobulinemic vasculitis (CV), IgA vasculitis (Henoch-Schönlein) (IgAV), and hypocomplementemic urticarial vasculitis (HUV)) (anti-C1q vasculitis). Non-limiting examples of variable vessel vasculitis (VVV) include Behcet's disease (BD) and Cogan's syndrome (CS). Non-limiting examples of single-organ vasculitis (SOV) include cutaneous leukocytoclastic angiitis, cutaneous arteritis, primary central nervous system vasculitis, and isolated aortitis. Non-limiting examples of vasculitis associated with systemic disease include lupus vasculitis, rheumatoid vasculitis, and sarcoid vasculitis. Non-limiting examples of vasculitis associated with probable etiology include hepatitis C virus-associated cryoglobulinemic vasculitis, hepatitis B virus-associated vasculitis, syphilis-associated aortitis, drug-associated immune complex vasculitis, drug-associated ANCA-associated vasculitis, and cancer-associated vasculitis. Other examples of vasculitis include antiphospholipid syndrome, Buerger's disease (thromboangiitis obliterans), cryoglobulinemia, cryopyrin-associated autoinflammatory syndrome (CAPS) (juvenile), goodpastures, localized scleroderma (juvenile), polymyalgia rheumatica, Raynaud's phenomenon, scleroderma, Sjogren's syndrome, and systemic lupus erythematosus. It is contemplated that the bioconjugates and methods disclosed herein can be used to inhibiting and/or treating vasculitis.

In one embodiment, provided herein are methods for preventing and/or treating vessel vasculitis. In one embodiment, provided herein are methods for preventing and/or treating small vessel vasculitis, including antineutrophil cytoplasmic antibody (ANCA)-associated vasculitis (AAV), microscopic polyangiitis (MPA), granulomatosis with polyangiitis (Wegener's) (GPA), eosinophilic granulomatosis with polyangiitis (Churg-Strauss) (EGPA), immune complex SVV, anti-glomerular basement membrane (anti-GBM) disease, gryoglobulinemic vasculitis (CV), IgA vasculitis (Henoch-Schönlein) (IgAV), and/or hypocomplementemic urticarial vasculitis (HUV)) (anti-Clq vasculitis). Such diseases affect small vessels (e.g., very small arteries, arterioles, capillaries, and small veins).

Combination Therapy

In some embodiments, the compositions of the present disclosure can be used in combination with a second agent useful for preventing or treating fibrosis. Accordingly, in one embodiment, a combination, composition, package or kit is provided that includes any composition of the present disclosure and one or more such second agent. In one embodiment, any treatment method of the present disclosure further includes administration of one or more such second agent.

The second agent can be any pharmaceutical or biologic agent that is useful for preventing, treating or otherwise ameliorating symptoms of fibrosis. Non-limiting examples include steroids such as predonine, reducing agents such as N-acetylcysteine, antifibrotic drugs such as pirfenidone and nintedanib, immunosuppressive drugs such as corticosteroids, cyclophosphamide, azathioprine, methotrexate, penicillamine, and cyclosporine A and FK506, and other agents like colchicine, IFN-γ and mycophenolate mofetil.

In some embodiments, the compositions of the present disclosure can be used in combination with a second agent useful for preventing or treating vasculitis. Accordingly, in one embodiment, a combination, composition, package or kit is provided that includes any composition of the present disclosure and one or more such second agent. In one embodiment, any treatment method of the present disclosure further includes administration of one or more such second agent.

The second agent can be any pharmaceutical or biologic agent that is useful for preventing, treating or otherwise ameliorating symptoms of vasculitis. Non-limiting examples include prednisone, Cyclophosphamide (Cytoxan), methylprednisolone, methotrexate sodium, Medrol (Pak), Medrol, dexamethasone, prednisolone, DexPak, Deltasone, cortisone, Prednisone Intensol, dexamethasone sodium phosphate, Orapred ODT, Trexall, Rheumatrex, methotrexate sodium (PF), Veripred 20, Dexamethasone Intensol, prednisolone sodium phosphate, Pediapred, Millipred, Rayos, Millipred, and DoubleDex.

4. Compositions

In one embodiment, the bioconjugate is administered in a composition. The present disclosure provides compositions comprising a bioconjugate and a pharmaceutically acceptable carrier. Pharmaceutically acceptable carriers are known to one having ordinary skill in the art may be used, including water or saline. As is known in the art, the components as well as their relative amounts are determined by the intended use and method of delivery. Diluent or carriers employed in the compositions can be selected so that they do not diminish the desired effects of the bioconjugate. Examples of suitable compositions include aqueous solutions, for example, a solution in isotonic saline, 5% glucose. Other well-known pharmaceutically acceptable liquid carriers such as alcohols, glycols, esters and amides, may be employed. In certain embodiments, the composition further comprises one or more excipients, such as, but not limited to ionic strength modifying agents, solubility enhancing agents, sugars such as mannitol or sorbitol, pH buffering agent, surfactants, stabilizing polymer, preservatives, and/or co-solvents.

In certain embodiments, the composition is an aqueous solution. Aqueous solutions are suitable for use in composition formulations based on ease of formulation, as well as an ability to easily administer such compositions by means of instilling the solution in. In certain embodiments, the compositions are suspensions, viscous or semi-viscous gels, or other types of solid or semi-solid compositions. In some embodiments, the composition is in the form of foams, ointments, liquid wash, gels, sprays and liposomes, which are very well known in the art. Alternatively, the topical administration is an infusion of the provided bioconjugate to the treatment site via a device selected from a pump-catheter system, a continuous or selective release device, or an adhesion barrier. In certain embodiments, the composition is a solution that is directly applied to or contacts the internal wall of a vein or artery. In some embodiments, the composition comprises a polymer matrix. In other embodiments, the composition is absorbable. In certain embodiments, the composition comprises a pH buffering agent. In some embodiments, the composition contains a lubricity enhancing agent.

In certain embodiments, a polymer matrix or polymeric material is employed as a pharmaceutically acceptable carrier or support for the composition. The polymeric material described herein may comprise natural or unnatural polymers, for example, such as sugars, peptides, protein, laminin, collagen, hyaluronic acid, ionic and non-ionic water soluble polymers; acrylic acid polymers; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; poly(lactic acid), poly(glycolic acid), copolymers of lactic and glycolic acids, or other polymeric agents both natural and synthetic. In certain embodiments, the compositions provided herein is formulated as films, gels, foams, or and other dosage forms.

Suitable ionic strength modifying agents include, for example, glycerin, propylene glycol, mannitol, glucose, dextrose, sorbitol, sodium chloride, potassium chloride, and other electrolytes.

In certain embodiments, the solubility of the bioconjugate may need to be enhanced. In such cases, the solubility may be increased by the use of appropriate formulation techniques, such as the incorporation of solubility-enhancing compositions such as mannitol, ethanol, glycerin, polyethylene glycols, propylene glycol, poloxamers, and others known in the art.

In certain embodiments, the composition contains a lubricity enhancing agent. As used herein, lubricity enhancing agents refer to one or more pharmaceutically acceptable polymeric materials capable of modifying the viscosity of the pharmaceutically acceptable carrier. Suitable polymeric materials include, but are not limited to: ionic and non-ionic water soluble polymers; hyaluronic acid and its salts, chondroitin sulfate and its salts, dextrans, gelatin, chitosans, gellans, other bioconjugates or polysaccharides, or any combination thereof; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; collagen and modified collagens; galactomannans, such as guar gum, locust bean gum and tara gum, as well as polysaccharides derived from the foregoing natural gums and similar natural or synthetic gums containing mannose and/or galactose moieties as the main structural components (e.g., hydroxypropyl guar); gums such as tragacanth and xanthan gum; gellan gums; alginate and sodium alginate; chitosans; vinyl polymers; hydrophilic polymers such as polyethylene oxides, polyoxyethylene-polyoxypropylene copolymers, and polyvinylalcohol; carboxyvinyl polymers or crosslinked acrylic acid polymers such as the "carbomer" family of polymers, e.g., carboxypolyalkylenes that may be obtained commercially under the Carbopol™ trademark; and various other viscous or viscoelastomeric substances. In one embodiment, a lubricity enhancing agent is selected from the group consisting of hyaluronic acid, dermatan, chondroitin, heparin, heparan, keratin, dextran, chitosan, alginate, agarose, gelatin, hydroxypropyl cellulose, hydroxyethyl cellulose, hydroxypropyl methylcellulose, hydroxypropyl methylcellulose phthalate, methyl cellulose, carboxymethyl cellulose, and etherified cellulose, polyvinyl alcohol, polyvinylpyrrolidinone, povidone, carbomer 941, carbomer 940, carbomer 971P, carbomer 974P, or a pharmaceutically acceptable salt thereof. In one embodiment, a lubricity enhancing agent is applied concurrently with the bioconjugate. Alternatively, in one embodiment, a lubricity enhancing agent is applied sequentially to the bioconjugate. In one embodiment, the lubricity enhancing agent is chondroitin sulfate. In one embodiment, the lubricity enhancing agent is hyaluronic acid. The lubricity enhancing agent can change the viscosity of the composition.

For further details pertaining to the structures, chemical properties and physical properties of the above lubricity enhancing agents, see e.g., U.S. Pat. Nos. 5,409,904, 4,861,760 (gellan gums), U.S. Pat. Nos. 4,255,415, 4,271,143 (carboxyvinyl polymers), WO 94/10976 (polyvinyl alcohol), WO 99/51273 (xanthan gum), and WO 99/06023 (galactomannans) Typically, non-acidic lubricity enhancing agents, such as a neutral or basic agent are employed in order to facilitate achieving the desired pH of the formulation.

In some embodiments, the bioconjugates can be combined with minerals, amino acids, sugars, peptides, proteins, vitamins (such as ascorbic acid), or laminin, collagen, fibronectin, hyaluronic acid, fibrin, elastin, or aggrecan, or growth factors such as epidermal growth factor, platelet-derived growth factor, transforming growth factor beta, or fibroblast growth factor, and glucocorticoids such as dexamethasone or viscoelastic altering agents, such as ionic and non-ionic water soluble polymers; acrylic acid polymers; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; poly(lactic acid), poly(glycolic acid), copolymers of lactic and glycolic acids, or other polymeric agents both natural and synthetic.

Suitable pH buffering agents for use in the compositions herein include, for example, acetate, borate, carbonate, citrate, and phosphate buffers, as well as hydrochloric acid, sodium hydroxide, magnesium oxide, monopotassium phosphate, bicarbonate, ammonia, carbonic acid, hydrochloric acid, sodium citrate, citric acid, acetic acid, disodium hydrogen phosphate, borax, boric acid, sodium hydroxide, diethyl barbituric acid, and proteins, as well as various biological buffers, for example, TAPS, Bicine, Tris, Tricine, HEPES, TES, MOPS, PIPES, cacodylate, or MES. In certain embodiments, an appropriate buffer system (e.g., sodium phosphate, sodium acetate, sodium citrate, sodium borate or boric acid) is added to the composition to prevent pH drift under storage conditions. In some embodiments, the buffer is a phosphate buffered saline (PBS) solution (i.e., containing sodium phosphate, sodium chloride and in some formulations, potassium chloride and potassium phosphate). The particular concentration will vary, depending on the agent employed. In certain embodiments, the pH buffer system (e.g., sodium phosphate, sodium acetate, sodium citrate, sodium borate or boric acid) is added to maintain a pH within the range of from about pH 4 to about pH 8, or about pH 5 to about pH 8, or about pH 6 to about pH 8, or about pH 7 to about pH 8. In some embodiments, the buffer is chosen to maintain a pH within the range of from about pH 4 to about pH 8. In some embodiments, the pH is from about pH 5 to about pH 8. In some embodiments, the buffer is a saline buffer. In certain embodiments, the pH is from about pH 4 and about pH 8, or from about pH 3 to about pH 8, or from about pH 4 to about pH 7. In some embodiments, the composition is in the form of a film, gel, patch, or liquid solution which comprises a polymeric matrix, pH buffering agent, a lubricity enhancing agent and a bioconjugate wherein the composition optionally contains a preservative; and wherein the pH of said composition is within the range of about pH 4 to about pH 8.

Surfactants are employed in the composition to deliver higher concentrations of bioconjugate. The surfactants function to solubilize the inhibitor and stabilize colloid dispersion, such as micellar solution, microemulsion, emulsion and suspension. Suitable surfactants comprise c polysorbate, poloxamer, polyoxyl 40 stearate, polyoxyl castor oil, tyloxapol, triton, and sorbitan monolaurate. In one embodiment, the surfactants have hydrophile/lipophile/balance (HLB) in the range of 12.4 to 13.2 and are acceptable for ophthalmic use, such as TritonX114 and tyloxapol.

In certain embodiments, stabilizing polymers, i.e., demulcents, are added to the composition. The stabilizing polymer should be an ionic/charged example, more specifically a polymer that carries negative charge on its surface that can exhibit a zeta-potential of (−)10-50 mV for physical stability and capable of making a dispersion in water (i.e. water soluble). In one embodiment, the stabilizing polymer comprises a polyelectrolyte or polyelectrolytes if more than one, from the family of cross-linked polyacrylates, such as carbomers and Pemulen®, specifically Carbomer 974p (polyacrylic acid), at a range of about 0.1% to about 0.5% w/w.

In one embodiment, the composition comprises an agent which increases the permeability of the bioconjugate to the extracellular matrix of blood vessels. Preferably the agent which increases the permeability is selected from benzalkonium chloride, saponins, fatty acids, polyoxyethylene fatty ethers, alkyl esters of fatty acids, pyrrolidones, polyvinylpyrrolidone, pyruvic acids, pyroglutamic acids or mixtures thereof.

The bioconjugate may be sterilized to remove unwanted contaminants including, but not limited to, endotoxins and infectious agents. Sterilization techniques which do not adversely affect the structure and biotropic properties of the bioconjugate can be used. In certain embodiments, the bioconjugate can be disinfected and/or sterilized using conventional sterilization techniques including propylene oxide or ethylene oxide treatment, sterile filtration, gas plasma sterilization, gamma radiation, electron beam, and/or sterilization with a peracid, such as peracetic acid. In one embodiment, the bioconjugate can be subjected to one or more sterilization processes. Alternatively, the bioconjugate may be wrapped in any type of container including a plastic wrap or a foil wrap, and may be further sterilized.

In some embodiments, preservatives are added to the composition to prevent microbial contamination during use. Suitable preservatives added to the compositions comprise benzalkonium chloride, benzoic acid, alkyl parabens, alkyl benzoates, chlorobutanol, chlorocresol, cetyl alcohols, fatty alcohols such as hexadecyl alcohol, organometallic compounds of mercury such as acetate, phenylmercury nitrate or borate, diazolidinyl urea, diisopropyl adipate, dimethyl polysiloxane, salts of EDTA, vitamin E and its mixtures. In certain embodiments, the preservative is selected from benzalkonium chloride, chlorobutanol, benzododecinium bromide, methyl paraben, propyl paraben, phenylethyl alcohol, edentate disodium, sorbic acid, or polyquarternium-1. In certain embodiments, the compositions comprise a preservative. In some embodiments, the preservatives are employed at a level of from about 0.001% to about 1.0% w/v. In certain embodiments, the compositions do not contain a preservative and are referred to as "unpreserved". In some embodiments, the unit dose compositions are sterile, but unpreserved.

In some embodiments, separate or sequential administration of the bioconjugate and other agent is necessary to facilitate delivery of the composition. In certain embodiments, the bioconjugate and the other agent can be administered at different dosing frequencies or intervals. For example, the bioconjugate can be administered daily, while the other agent can be administered less frequently. Additionally, as will be apparent to those skilled in the art, the bioconjugate and the other agent can be administered using the same route of administration or different routes of administration.

Any effective regimen for administering the bioconjugate can be used. For example, the bioconjugate can be administered as a single dose, or as a multiple-dose daily regimen. Further, a staggered regimen, for example, one to five days per week can be used as an alternative to daily treatment.

In various embodiments, the bioconjugate can be administered topically, such as by film, gel, patch, or liquid solution. In some of the embodiments, the compositions provided are in a buffered, sterile aqueous solution. In certain embodiments, the solutions have a viscosity of from about 1 to about 100 centipoises (cps), or from about 1 to about 200 cps, or from about 1 to about 300 cps, or from about 1 to about 400 cps. In some embodiments, the solutions have a viscosity of from about 1 to about 100 cps. In certain embodiments, the solutions have a viscosity of from about 1 to about 200 cps. In certain embodiments, the solutions have a viscosity of from about 1 to about 300 cps. In certain embodiments, the solutions have a viscosity of from about 1 to about 400 cps. In certain embodiments, the solution is in the form of an injectable liquid solution. In other embodiments, the compositions are formulated as viscous liquids, i.e., viscosities from several hundred to several thousand cps, gels or ointments. In these embodiments, the bioconjugate is dispersed or dissolved in an appropriate pharmaceutically acceptable carrier.

Exemplary compositions for use with the bioconjugates for catheter-based delivery may comprise: a) a synthetic bioconjugate as described herein; b) a pharmaceutically acceptable carrier; c) a polymer matrix; d) a pH buffering agent to provide a pH in the range of about pH 4 to about pH 8; and e) a water soluble lubricity enhancing agent in the concentration range of about 0.25% to about 10% total formula weight or any individual component a), b), c), d) or e), or any combinations of a), b), c), d) or e).

Exemplary formulations may comprise: a) bioconjugate as described herein; b) pharmaceutically acceptable carrier; c) polymer matrix; and d) pH buffering agent to provide a pH in the range of about pH 4 to about pH 8, wherein said solution has a viscosity of from about 3 to about 30 cps for a liquid solution.

Exemplary compositions contemplated by the present disclosure may also be for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present disclosure. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the component in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In making pharmaceutical compositions that include bioconjugates described herein, the active ingredient is usually diluted by an excipient or carrier and/or enclosed within such a carrier that can be in the form of a capsule, sachet, paper or other container. When the excipient serves as a diluent, it can be a solid, semi-solid, or liquid material (as above), which acts as a vehicle, carrier or medium for the active ingredient. Thus, the compositions can be in the form of films, gels, patches, powders, lozenges, sachets, cachets, elixirs, suspensions, emulsions, solutions, syrups, aerosols (as a solid or in a liquid medium), ointments containing, for example, up to 10% by weight of the active compounds, soft and hard gelatin films, gels, patches, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

Films used for drug delivery are well known in the art and comprise non-toxic, non-irritant polymers devoid of leachable impurities, such as polysaccharides (e.g., cellulose, maltodextrin, etc.). In some embodiments, the polymers are hydrophilic. In other embodiments, the polymers are hydrophobic. The film adheres to tissues to which it is applied, and is slowly absorbed into the body over a period of about a week. Polymers used in the thin-film dosage forms described herein are absorbable and exhibit sufficient peel, shear and tensile strengths as is well known in the art. In some embodiments, the film is injectable. In certain embodiments, the film is administered to the patient prior to, during or after surgical intervention.

Gels are used herein refer to a solid, jelly-like material that can have properties ranging from soft and weak to hard and tough. As is well known in the art, a gel is a non-fluid colloidal network or polymer network that is expanded throughout its whole volume by a fluid. A hydrogel is a type of gel which comprises a network of polymer chains that are hydrophilic, sometimes found as a colloidal gel in which water is the dispersion medium. Hydrogels are highly absorbent and can contain a high degree of water, such as, for example greater than 90% water. In some embodiments, the gel described herein comprises a natural or synthetic polymeric network. In some embodiments, the gel comprises a hydrophilic polymer matrix. In other embodiments, the gel comprises a hydrophobic polymer matrix. In some embodiments, the gel possesses a degree of flexibility very similar to natural tissue. In certain embodiments, the gel is biocompatible and absorbable. In certain embodiments, the gel is administered to the patient prior to, during or after surgical intervention.

Liquid solution as used herein refers to solutions, suspensions, emulsions, drops, ointments, liquid wash, sprays, liposomes which are well known in the art. In some embodiments, the liquid solution contains an aqueous pH buffer agent which resists changes in pH when small quantities of acid or base are added. In certain embodiments, the liquid solution is administered to the patient prior to, during or after surgical intervention.

Exemplary formulations may comprise: a) one or more bioconjugate as described herein; b) pharmaceutically acceptable carrier; and c) hydrophilic polymer as matrix network, wherein said compositions are formulated as viscous liquids, i.e., viscosities from several hundred to several thousand cps, gels or ointments. In these embodiments, the bioconjugate is dispersed or dissolved in an appropriate pharmaceutically acceptable carrier.

In certain embodiments, the bioconjugate, or a composition comprising the same, is lyophilized prior to, during or after, formulation. Accordingly, also provided herein is a lyophilized composition comprising a bioconjugate or composition comprising the same as described herein.

5. Dosing

Suitable dosages of the bioconjugate can be determined by standard methods, for example by establishing dose-response curves in laboratory animal models or in clinical trials and can vary significantly depending on the patient condition, the disease state being treated, the route of administration and tissue distribution, and the possibility of co-usage of other therapeutic treatments. The effective amount to be administered to a patient is based on body surface area, patient weight or mass, and physician assessment of patient condition. In various exemplary embodiments, a dose ranges from about 0.01 µg to about 10 g. For example, for systemic delivery, the dose can be about 10 g, or about 5 g, or about 1 g. In other illustrative embodiments, effective doses ranges from about 100 µg to about 10 g per dose, or from about 100 µg to about 1 g per dose, or from about 100 µg to about 500 mg per dose, from about 0.01 µg to about 100 mg per dose, or from about 100 µg to about 50 mg per dose, or from about 500 µg to about 10 mg per dose, or from about 1 mg to 10 mg per dose, or from about 1 to about 100 mg per dose, or from about 1 mg to 500 mg per dose, or from about 1 mg to 200 mg per dose, or from about 10 mg to 100 mg per dose, or from about 10 mg to 75 mg per dose, or from about 10 mg to 50 mg per dose, or about 10 mg per dose, or about 20 mg per dose, or about 30 mg per dose, or about 40 mg per dose, or about 50 mg per dose, or about 60 mg per dose, or about 70 mg per dose, or about 80 mg per dose, or about 90 mg per dose, or about 100 mg per dose. In any of the various embodiments described herein, effective doses ranges from about 0.01 µg to about 1000 mg per dose, 1 µg to about 100 mg per dose, about 100 µg to about 1.0 mg, about 50 µg to about 600 µg, about 50 µg to about 700 µg, about 100 µg to about 200 µg, about 100 µg to about 600 µg, about 100 µg to about 500 µg, about 200 µg to about 600 µg, or from about 100 µg to about 50 mg per dose, or from about 500 µg to about 10 mg per dose or from about 1 mg to about 10 mg per dose.

In some embodiments, the compositions are packaged in multidose form. Preservatives are thus required to prevent microbial contamination during use. In certain embodiments, suitable preservatives as described above can be added to the compositions. In some embodiments, the composition contains a preservative. In certain embodiments the preservatives are employed at a level of from about 0.001% to about 1.0% w/v. In some embodiments, the unit dose compositions are sterile, but unpreserved.

EXAMPLES

Example 1. Synthesis of Bioconjugates

Bioconjugates can be prepared according to the following protocol. A suitable reaction buffer is prepared (e.g., 2-(N-morpholino)ethanesulfonic acid (MES)) with an appropriate concentration of a chaotropic agent, such as butanol, ethanol, guanidinium chloride, lithium perchlorate, lithium acetate, magnesium chloride, phenol, propanol, sodium dodecyl sulfate, thiourea, or urea (e.g., from about 5 M to about 10 M urea). The final pH is adjusted to a pH of from about 4.5 to about 6 with 1 N HCl.

A hydrazide functionalized peptide (e.g., Peptides 1-20 in Table 2), were dissolved in reaction buffer to 3 mg/mL. The peptide solution was freshly prepared prior to the coupling reaction. The corresponding biotinylated peptide was dissolved in reaction buffer to 3 mg/mL. The resulting biotin-labeled peptide solution was freshly prepared prior to the coupling reaction. Glycan (e.g., heparin (MW$_{avg}$=16 kDa)) is dissolved in reaction buffer to 20 mg/mL and either stored at −20° C. or prepared freshly prior to the coupling reaction. EDC (1-Ethyl-3-(3-dimethylaminopropyl)carbodiimide) is dissolved to 75 mg/mL in reaction buffer immediately before adding to the glycan. Alternatively, the bioconjugate can be synthesized using only unlabeled peptide, and optionally labeled using biotin hydrazide.

Heparin was activated by adding 1-ethyl-3-(3-dimethyl-aminopropyl)carbodiimide (EDC) (59.3 mg or 0.79 mL dissolved at 75 mg/mL in water) in a 50 molar excess to heparin. The starting materials were reacted at room temperature for about 5 minutes. The biotin-labeled peptide was then added to the activated heparin in a 1:1 molar ratio (heparin:labeled peptide) (15.3 mg or 5.1 mL at 3 mg/mL in reaction buffer). The reaction mixture was then shaken for about 5 minutes at room temperature. While shaking, unlabeled peptide was added in a given molar ratio (heparin:

peptide, see Table 2 for details) in reaction buffer. The components were then allowed to react for about 2 hours at room temperature while shaking. After the allotted time, the reaction was quenched by raising the pH to 8 with 0.5 M NaOH (approximately 4.5 mL) for about 30 minutes at room temperature while shaking.

The resulting bioconjugate was purified via diafilter (Spectrum-MidiKros mPES 10 K hollow tube filter) using 5 column volumes (CVs) of reaction buffer (approximately 250 mL), followed by 10 CVs of water (approximately 500 mL) at a flow rate of 35 mL/min with TMP at approximately 15 psi. The retentate, which is the final product, was then frozen at −80° C. Optionally, the final product is lyophilized to dryness. About 5 peptides were conjugated to the glycan using the procedure outlined above.

The following bioconjugates were prepared from heparin as described above, and the hydrazide functionalized peptides shown in the table (Table 2).

TABLE 2

| Compound | Hydrazide Functionalized Peptide | SEQ ID NO: |
|---|---|---|
| Compound 1 (1:8, glycan to peptide) | RRANAALKAGELYKSILYGSG-NHNH$_2$ (Peptide 1) | 77 |
| Compound 2 (1:8, glycan to peptide) | RRANAALKAGELYKSILYGSGRRGSG-NHNH$_2$ (Peptide 2) | 94 |
| Compound 3 (1:8, glycan to peptide) | GQLYKSILYGSG-NHNH$_2$ (Peptide 3) | 59 |
| Compound 4 (1:8, glycan to peptide) | GQLYKSILYGSGRRGSG-NHNH$_2$ (Peptide 4) | 95 |
| Compound 5 (1:8, glycan to peptide) | GQLYKSILYGSGSGSGS-NHNH$_2$ (Peptide 5) | 96 |
| Compound 6 (1:8, glycan to peptide) | GQLYKSILYGSRGRGSG-NHNH$_2$ (Peptide 6) | 97 |
| Compound 7 (1:8, glycan to peptide) | GQLYKSILYGRSGRGSG-NHNH$_2$ (Peptide 7) | 98 |
| Compound 8 (1:8, glycan to peptide) | GQLYKSILYGSRGSG-NHNH$_2$ (Peptide 8) | 99 |
| Compound 9 (1:8, glycan to peptide) | GQLYKSILYRRGSGSGS-NHNH$_2$ (Peptide 9) | 100 |
| Compound 10 (1:8, glycan to peptide) | GQLYKSILYGSGSGSRR-NHNH$_2$ (Peptide 10) | 6 |
| Compound 11 (1:8, glycan to peptide) | GQLYKSILYGSRRGS-NHNH$_2$ (Peptide 11) | 101 |
| Compound 12 (1:8, glycan to peptide) | GQLYKSILYGSGRRRGSG-NHNH$_2$ (Peptide 12) | 102 |
| Compound 13 (1:8, glycan to peptide) | GQLYKSILYGSGRGSGSGSG-NHNH$_2$ (Peptide 13) | 103 |
| Compound 14 (1:8, glycan to peptide) | GQLYKSILYGSGKKGSG (Peptide 14) | 104 |
| Compound 15 (1:8, glycan to peptide) | GQLYKSILYAhxRRAhx-NHNH$_2$ (Peptide 15)* | 105 |
| Compound 16 (1:8, glycan to peptide) | RVMHGLHLGDDEGSGNHNH$_2$ (Peptide 16) | 106 |
| Compound 17 (1:8, glycan to peptide) | CPGRVMHGLHLGDDEGPCGSG-NHNH$_2$ (Peptide 17) | 107 |
| Compound 18 (1:8 or 1:12, glycan to peptide) | CPGRVMHGLHLGDDEGPCGSGRRGSG-NHNH$_2$ (Peptide 18) | 108 |
| Compound 19 (1:4, glycan to peptide) | (RVMHGLHLGDDEGSG)2-KRRGSG-NHNH$_2$ (Peptide 19) | 106 & 109 |
| Compound 20 (1:6, glycan to peptide) | H$_2$NNH-Succinic Acid-GSGGQLYKSILY (Peptide 20) | 61 |

*Ahx = 6-aminohexanoic acid

Compounds 1-17 and 20 were synthesized by reacting peptide at a ratio of about 1:8, or about 1:6, peptides per glycan, and it is contemplated that the average number of peptides conjugated to glycan is about 5 peptides per glycan, corresponding to about 22% peptide functionalization. Compound 18 was synthesized by reacting peptide at a ratio of about 1:8, or about 1:9, or about 1:12, peptides per glycan, and it is contemplated that the average number of peptides conjugated to glycan is about 8 peptides per glycan, corresponding to about 33% peptide functionalization. Compound 19 was synthesized by reacting peptide at a ratio of about 1:4, or about 1:3, peptides per glycan, and it is contemplated that the average number of peptides conjugated to glycan is about 3 peptides per glycan, corresponding to about 11% peptide functionalization.

Example 2. Collagen-Binding Plate Assay

The following method is used to assess the binding affinity of bioconjugates disclosed herein for collagen.

Collagen-binding of bioconjugate variants is compared by a plate-assay, in which collagen is coated on 96-well plates. Collagen is coated on high-bind plates at 50 µg/mL in 0.02 N acetic acid for 1 hour at room temperature. Unbound collagen is rinsed with 1×PBS pH 7.4. Plates are then blocked in 1% milk in 1×PBS solution for 1 hour at room temperature.

Bioconjugate variants containing biotinlyated peptides are dissolved to a final concentration of 1 mg/mL in 1% milk in 1×PBS pH 7.4. From this solution, a 10× serial dilution is performed. Molecules are then incubated on the blocked collagen-coated plates and incubated for 15 minutes at room temperature. Plates are then rinsed 3 times with 1×PBS in 1% BSA and 0.2% Tween20.

Bound molecules are detected by streptavidin-HRP, which was diluted 1:500 in 1× PBS with 1% BSA and 0.2% Tween20 and incubated 200 µL/well for 20 minutes at room temperature. Streptavidin solution is rinsed from the plates 3 times with 1×PBS with 0.2% Tween20. TMB Substrate solution is then added to each well 100 µL/well for 15 minutes at room temperature, and the color evolution was stopped with 100 µL sulfuric acid solution (0.16 M). Absorbance in the well is then measured at 450 nm and binding affinity plotted in a dose-response by absorbance vs. concentration.

This method was used to compare collagen binding affinity of various collagen-binding bioconjugates by comparing $EC_{50}$ values. More specifically, the $EC_{50}$ values for each bioconjugate was compared to the $EC_{50}$ for Compound 4.

FIG. 1 shows a comparison of collagen binding for bioconjugates Compound 4, Compound 8, and Compound 13. FIG. 1 shows that decreasing the number of arginines increases $EC_{50}$.

Figure 2:
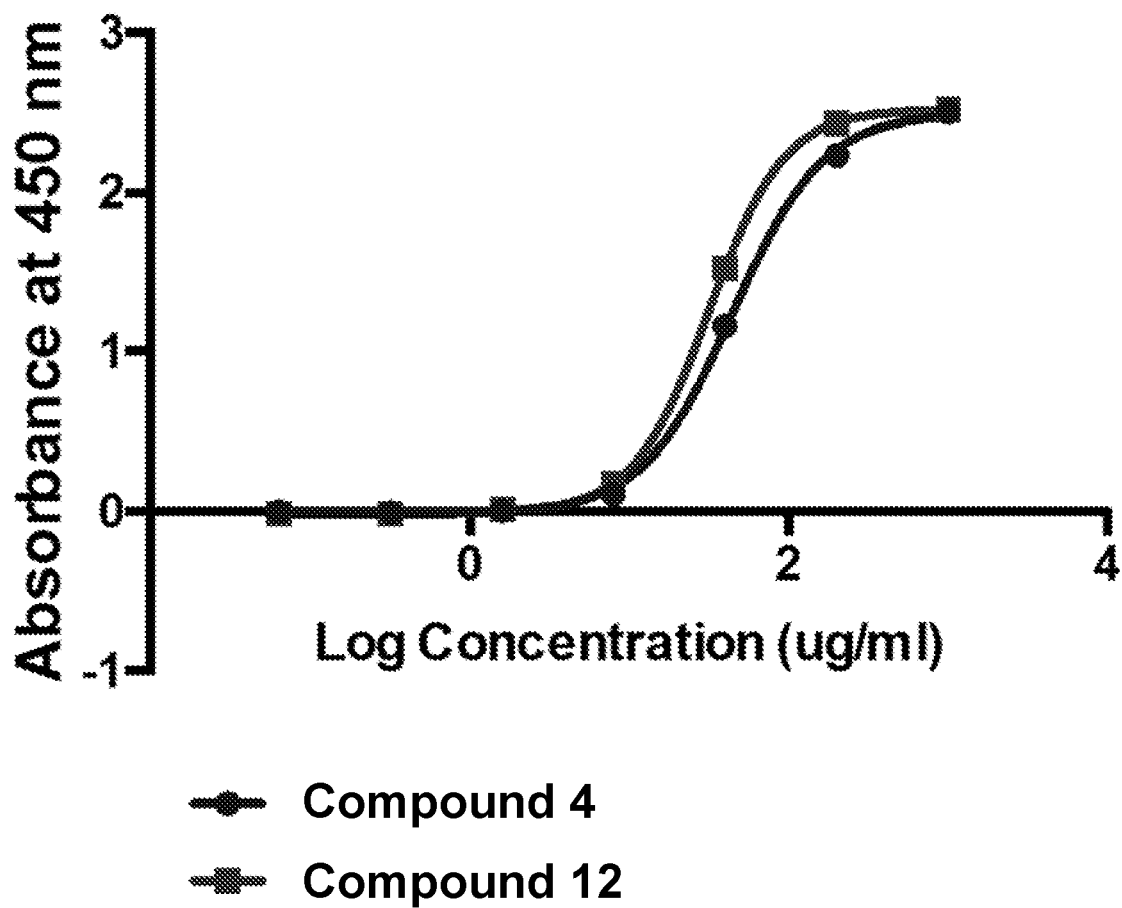
FIG. 2 shows a comparison of collagen binding for bioconjugates Compound 4 and Compound 12.

FIG. 2 shows a comparison of collagen binding for bioconjugates Compound 4 and Compound 12. FIG. 2 shows that increasing the number of arginines decreases $EC_{50}$.

Figure 3:
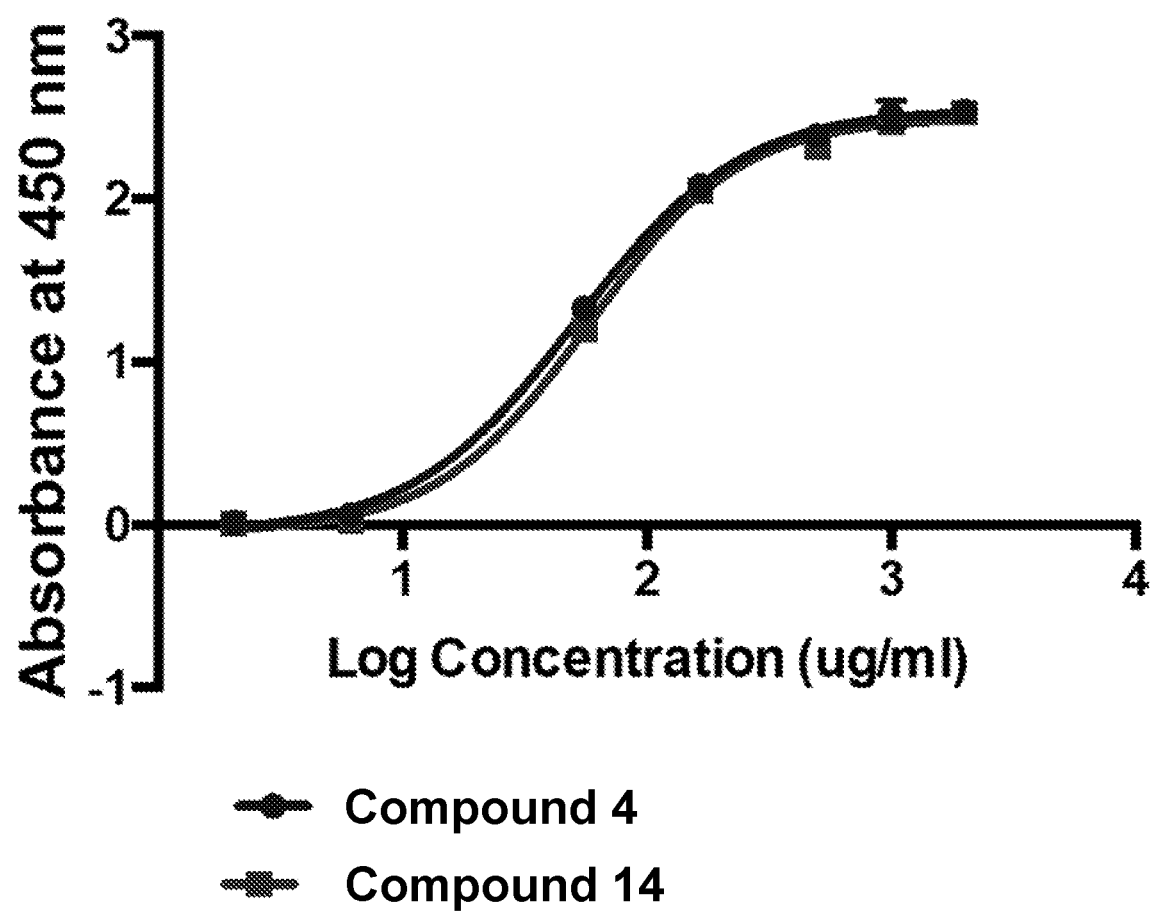
FIG. 3 shows a comparison of collagen binding for bioconjugates Compound 4 and Compound 14.

FIG. 3 shows a comparison of collagen binding for bioconjugates Compound 4 and Compound 14. FIG. 3 shows that substituting arginine with another positively charged amino acid (specifically, lysine) does not affect binding $EC_{50}$.

Figure 4:
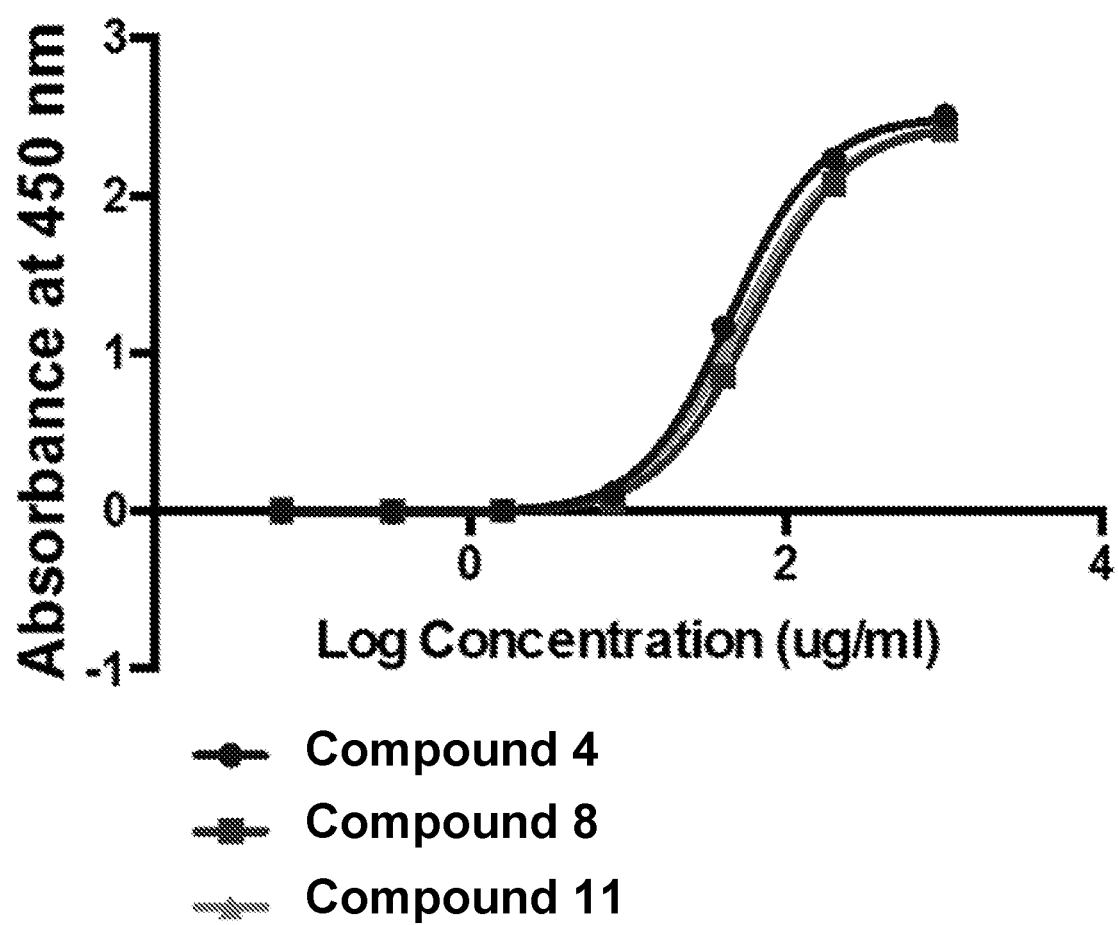
FIG. 4 shows a comparison of collagen binding for bioconjugates Compound 4, Compound 8, and Compound 11.

FIG. 4 shows a comparison of collagen binding for bioconjugates Compound 4, Compound 8, and Compound 11. FIG. 4 shows that decreasing the number of amino acids slightly increases $EC_{50}$.

Figure 5:
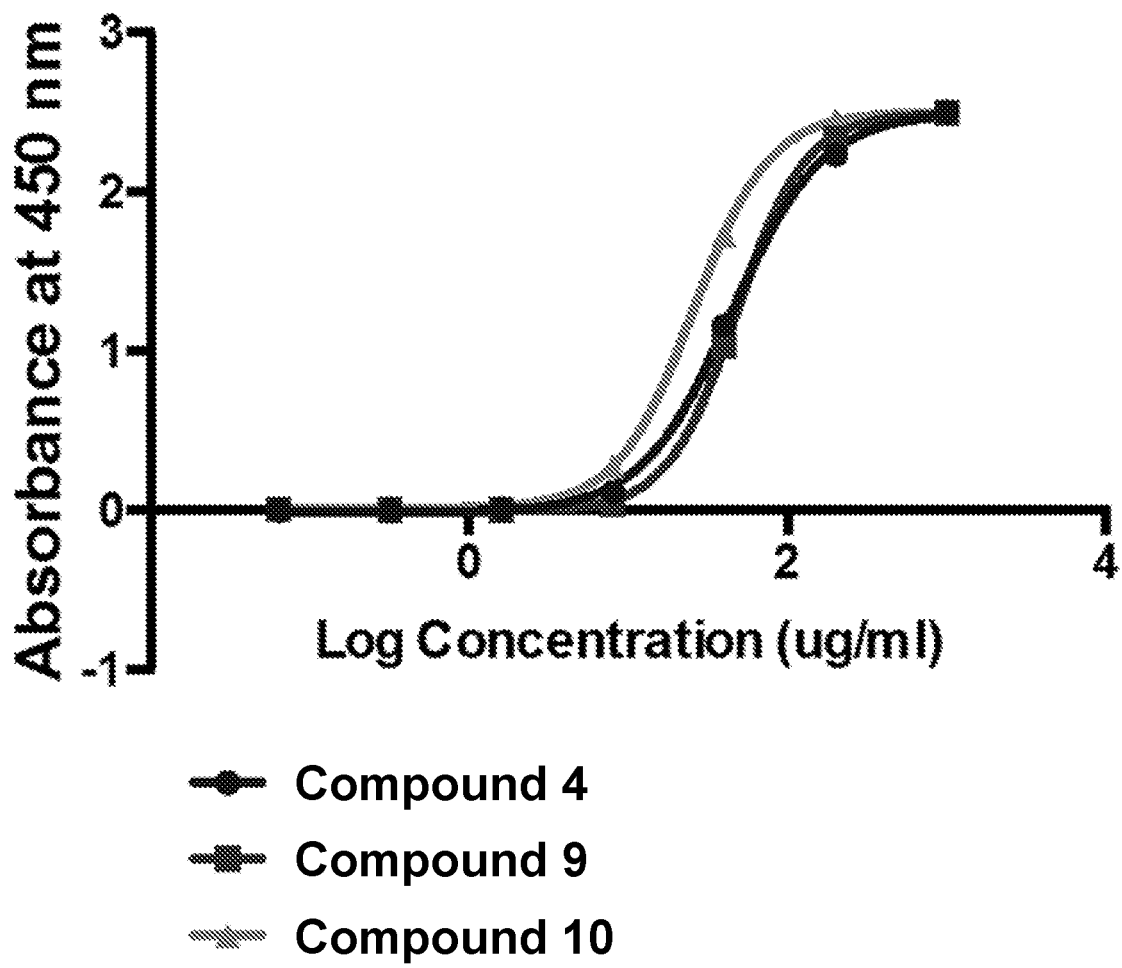
FIG. 5 shows a comparison of collagen binding for bioconjugates Compound 4, Compound 9, and Compound 10.

FIG. 5 shows a comparison of collagen binding for bioconjugates Compound 4, Compound 9, and Compound 10. FIG. 5 shows that placing arginine residues closer to the glycan decreases the $EC_{50}$.

FIGS. 1-5 indicate that there is a correlation to the quantity and location (with respect to the glycan) of positively charged amino acid residues in the peptide portion of the bioconjugate.

Figure 6:
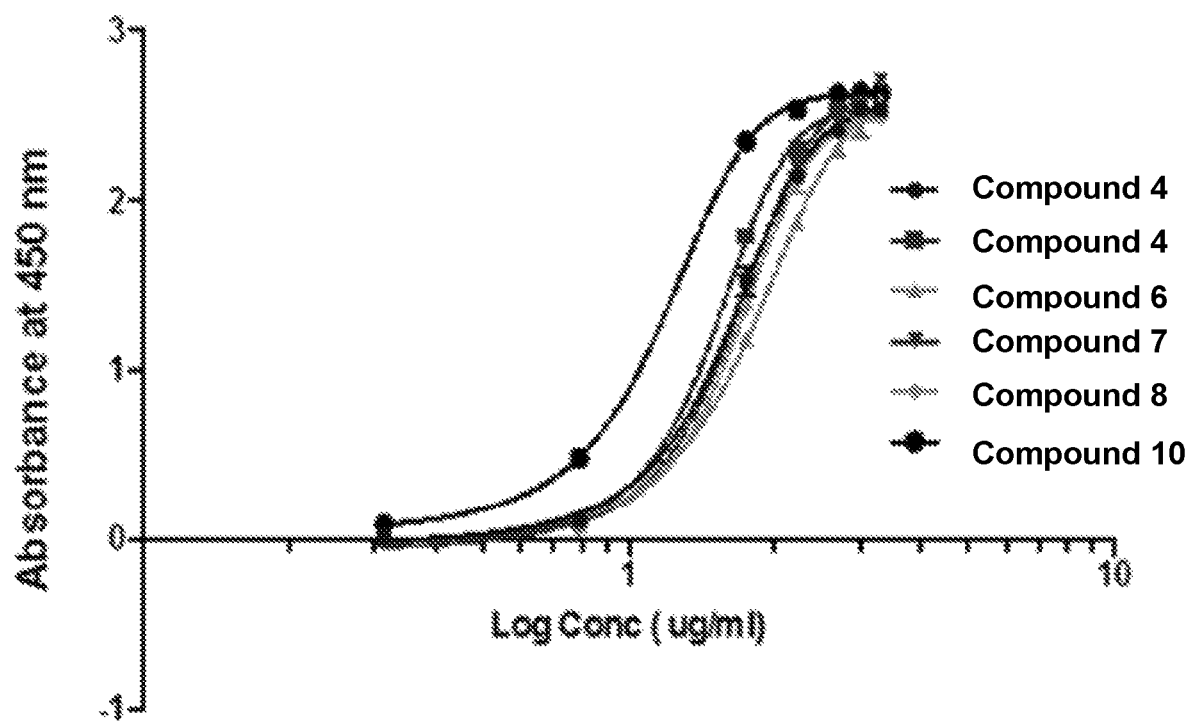
FIG. 6 shows a comparison of collagen binding for some of the bioconjugates of FIGS. 1-5 and FIG. 7 shows a bar graph comparing the corresponding $EC_{50}$ values.
Figure 7:
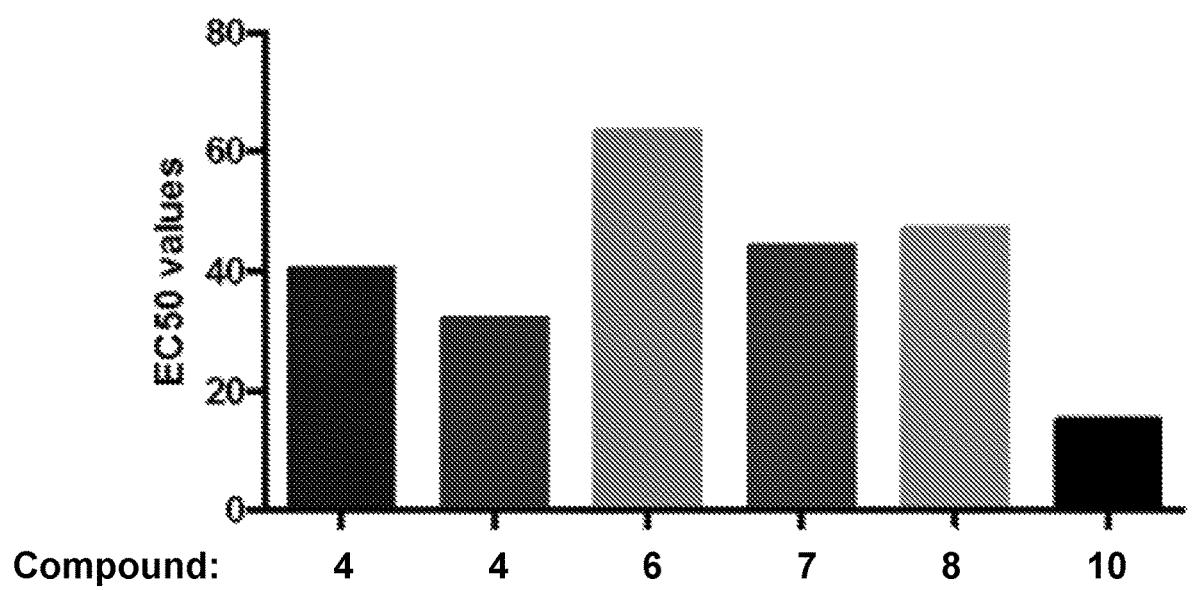

FIG. 6 shows a comparison of collagen binding for bioconjugates Compound 4 (two batches), Compound 6, Compound 7, Compound 8, and Compound 10 of FIGS. 1-5 and FIG. 7 shows a bar graph comparing the corresponding $EC_{50}$ values thereof.

Figure 8:
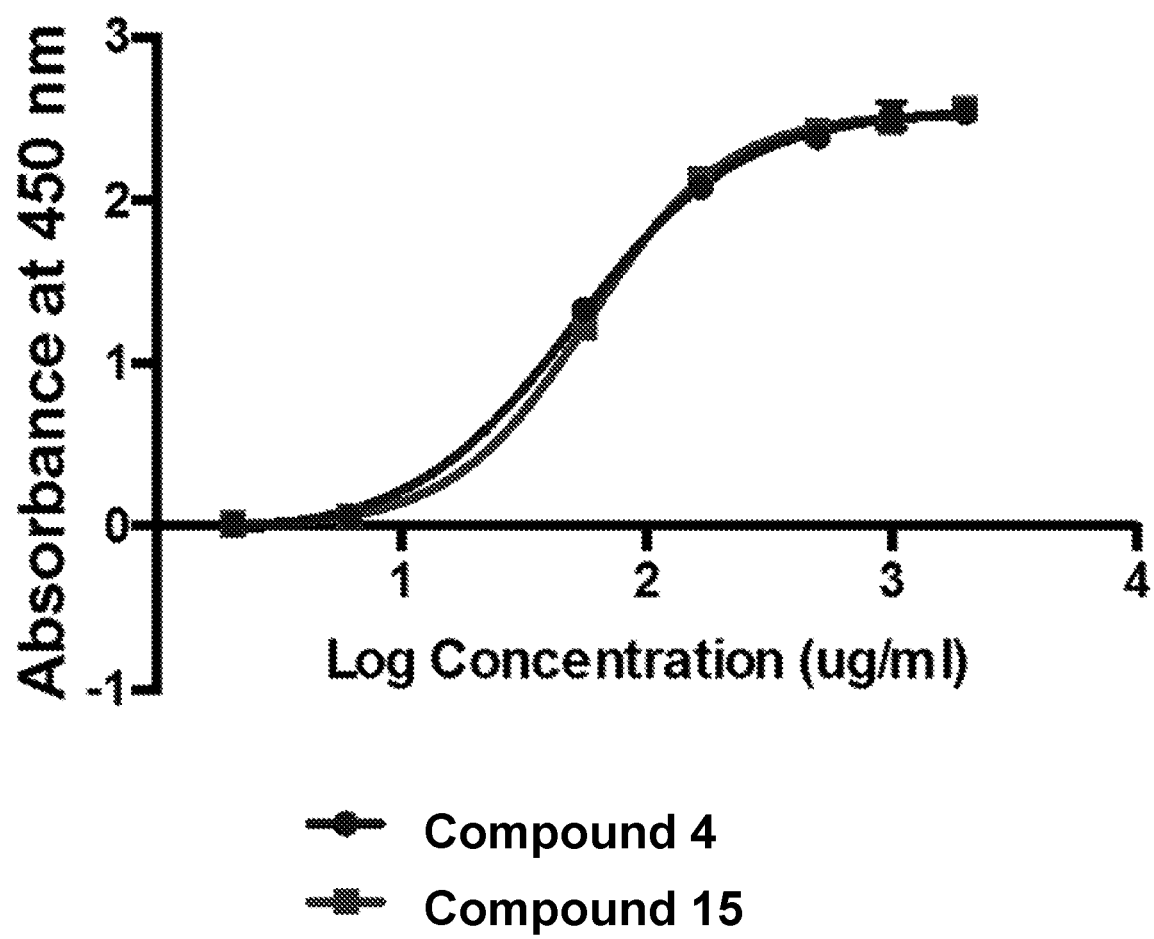
FIG. 8 shows a comparison of collagen binding for bioconjugates Compound 4 and Compound 11.

FIG. 8 shows a comparison of collagen binding for bioconjugates Compound 4 and Compound 15. FIG. 8 shows that substitution of GSG with 6-amino-1-hexanoic acid does not significantly affect $EC_{50}$, which indicates that binding is dependent on length in this region of the peptide, not the particular sequence.

Figure 9:
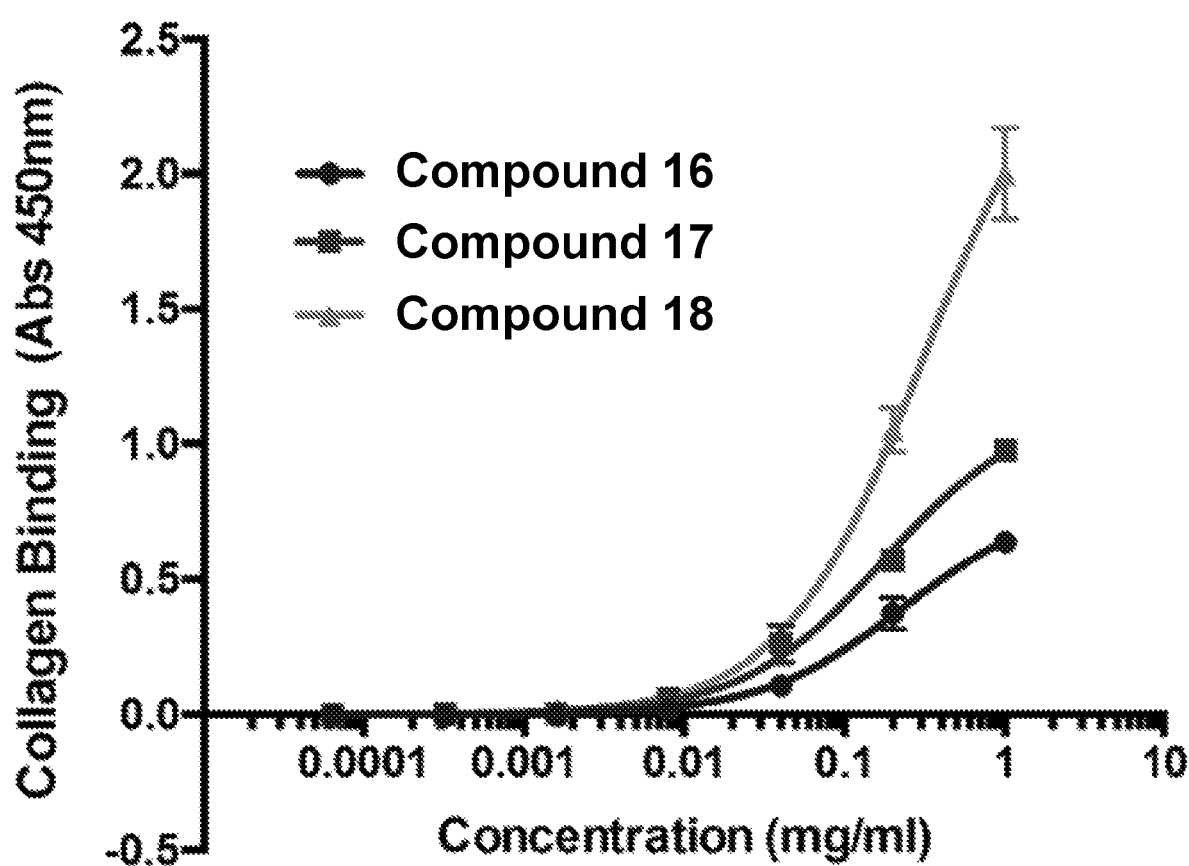
FIG. 9 shows a comparison of collagen binding for Compound 16, Compound 17, and Compound 18.

FIG. 9 shows a comparison of collagen binding for a linear bioconjugate (Compound 16), a cyclic bioconjugate (Compound 17), and Compound 18. Compound 18 showed a significant increase in collagen-binding affinity (lower $EC_{50}$).

Figure 10:
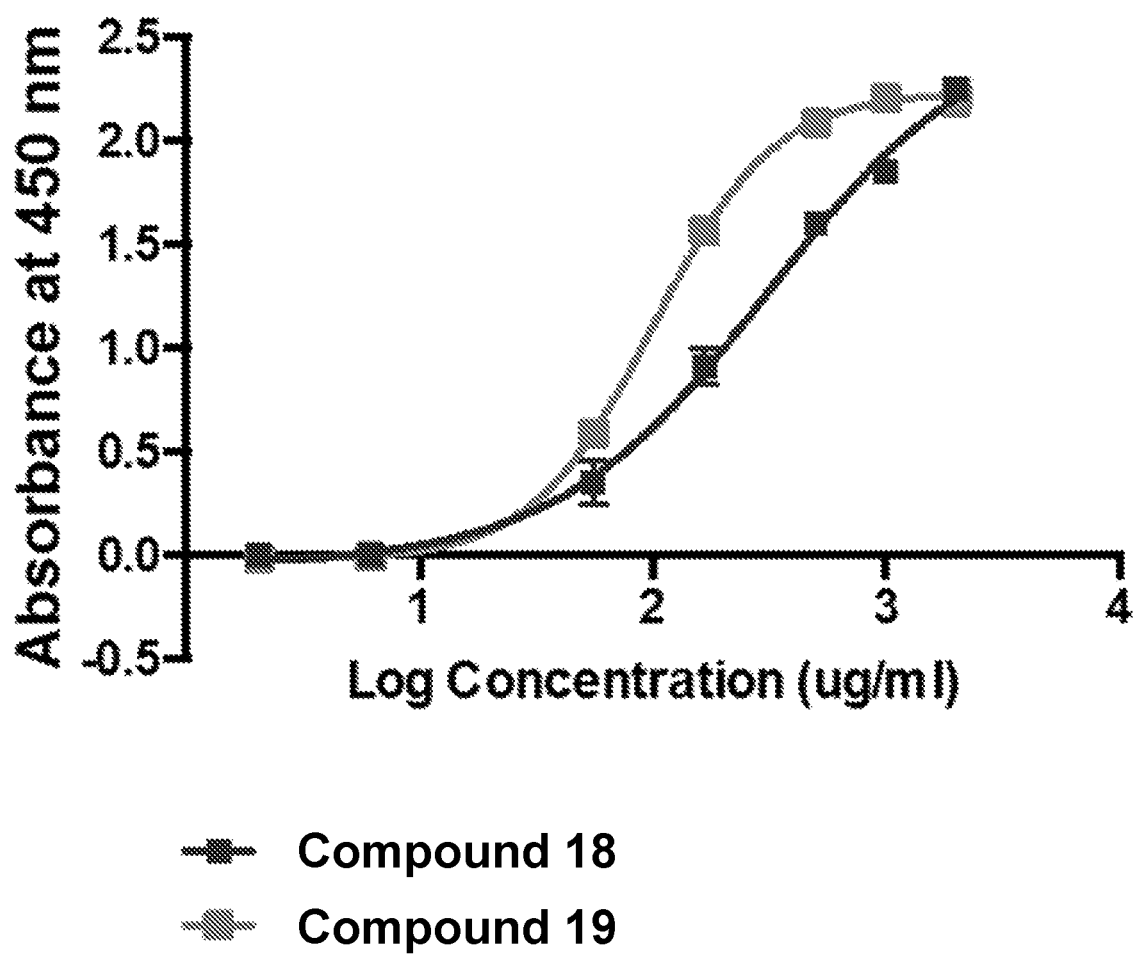
FIG. 10 shows a comparison of collagen binding for bioconjugates Compound 18 and Compound 19.

FIG. 10 shows a comparison of collagen binding for bioconjugates Compound 18 and Compound 19. Compound 19 show an increase in collagen binding affinity (lower $EC_{50}$).

Figure 11:
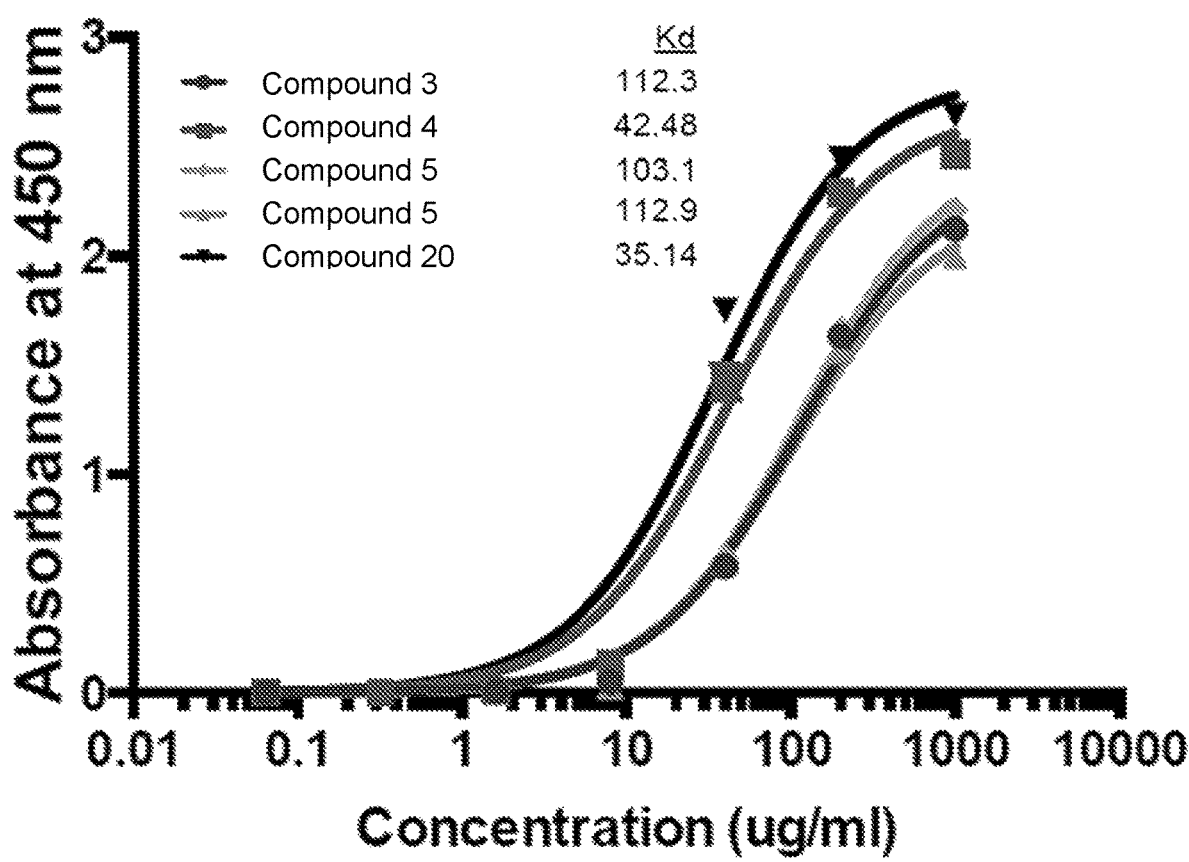
FIG. 11 shows a comparison of collagen binding for Compound 20, Compound 4, Compound 5, and Compound 3.

FIG. 11 shows a comparison of collagen binding for Compound 4, Compound 5 (two batches), and Compound 3. Compound 4 showed a significant increase in collagen binding affinity (lower Kd) compared to Compound 5 and Compound 3.

Example 3. Platelet Aggregation

Figure 12:
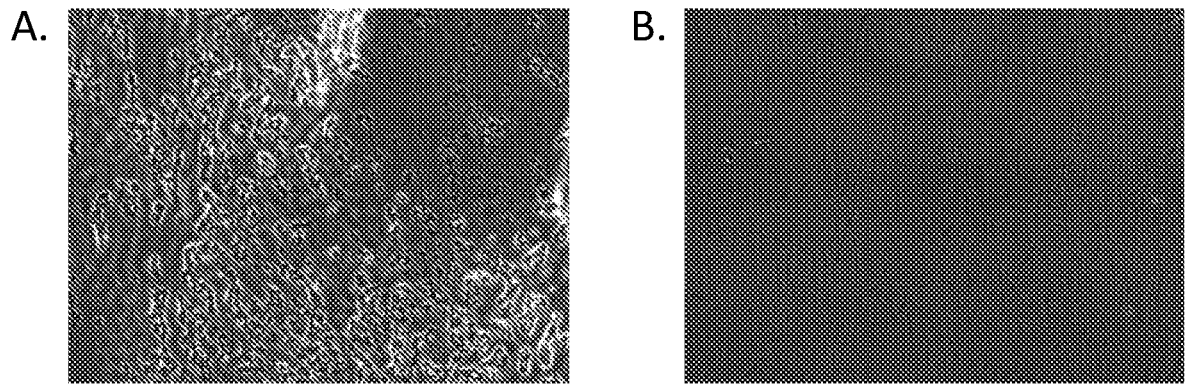
FIG. 12, panels A and B, show the effect of Compound 10 (panel B) on platelet binding to collagen as compared to Compound 1 (panel A).

Type I fibrillar collagen was adsorbed to Ibidi µ-slides by overnight incubation at 2-8° C. The Ibidi µ-slides were rinsed with Phosphate Buffer Saline (PBS), and then blocked with 1% BSA in 1×PBS. Compound 10 (shown in FIG. 12B) and Compound 1 at 2 mg/mL (shown in 12A) were applied to Ibidi µ-slides and left to incubate. After 1 hour excess conjugates were rinsed away with 1×PBS. Freshly drawn human whole blood was prestained with Calcein AM (Live Fluorescent cell marker). Blood was pumped across the channels at a sheer rate of 1000 s−1 using a syringe pump for 10 minutes. As blood flows across the Ibidi µ-Slides, Fluorescent microscope was used to take images of aggregated fluorescently labeled platelets. FIG. 12 shows that Compound 10 (panel 12B) inhibits platelet binding to Type I fibrillar collagen.

Example 4: Bioconjugates for Treatment or Prevention of Neointimal Hyperplasia or Peripheral Artery Disease (PAD)

Neointimal hyperplasia is evaluated in a rabbit angioplasty model in which a bioconjugate as described herein is delivered. Multiple (e.g., six) rabbits are enrolled in the study. Each animal receives a balloon angioplasty-mediated injury to both the right and left iliac artery. Animals are divided into test group (Heparin-SILY) or vehicle control (1×PBS). In each group, both iliac arteries are injured and treated with test article or control immediately following balloon injury.

After a given time (e.g., 28 days) following injury, animals are euthanized and the artery segments evaluated histologically. Several (e.g., three) histological sections with the most severe neointimal response from each vessel are typically selected for morphometry. Cross-sectional areas of the extranal elastic lamina (EEL), internal elastic lamina (IEL), and lumen are measured with digital morphometry (IPLab software, Rockville, Md.) from Movat stained slides. Neointimal thickness is measured as the distance from the IEL to the lumen, at minimal and maximal sites, and then averaged. The cross-sectional areas are used to calculated the following:

Medial area=EEL area−IEL area

Neointimal area=IEL area−Lumen area

Medial-Intimal Area=EEL area−lumen area

% Stenosis=[1−(Lumen area/IEL Area)]*100

The means of the variables are compared using analysis of variance (ANOVA). A p-value of less than 0.05 is typically considered statistically significant.

It is contemplated that the bioconjugates as described herein will be effective in inhibiting neointimal hyperplasia, and thus can be used to treat or prevent peripheral artery disease (PAD).

Example 5: Non-Alcoholic Steatohepatitis (NASH) Model

The ability of the compounds to affect liver fibrosis was tested in a mouse model of Non-Alcoholic Steatohepatitis (NASH). C57BL/6 mice received a single subcutaneous injection of 200 μg streptozotocin after birth. Beginning at 4 weeks of age, animals were fed a high fat diet. Beginning at week 5 and continuing for 4 weeks until week 9, animals received 3×/week intravenous treatment with saline or Compound 10. A separate group of animals received daily oral administration of Telmisartan during the same period Animals were sacrificed at 9 weeks of age and the livers were collected for histological and biochemical analysis.

Figure 13:
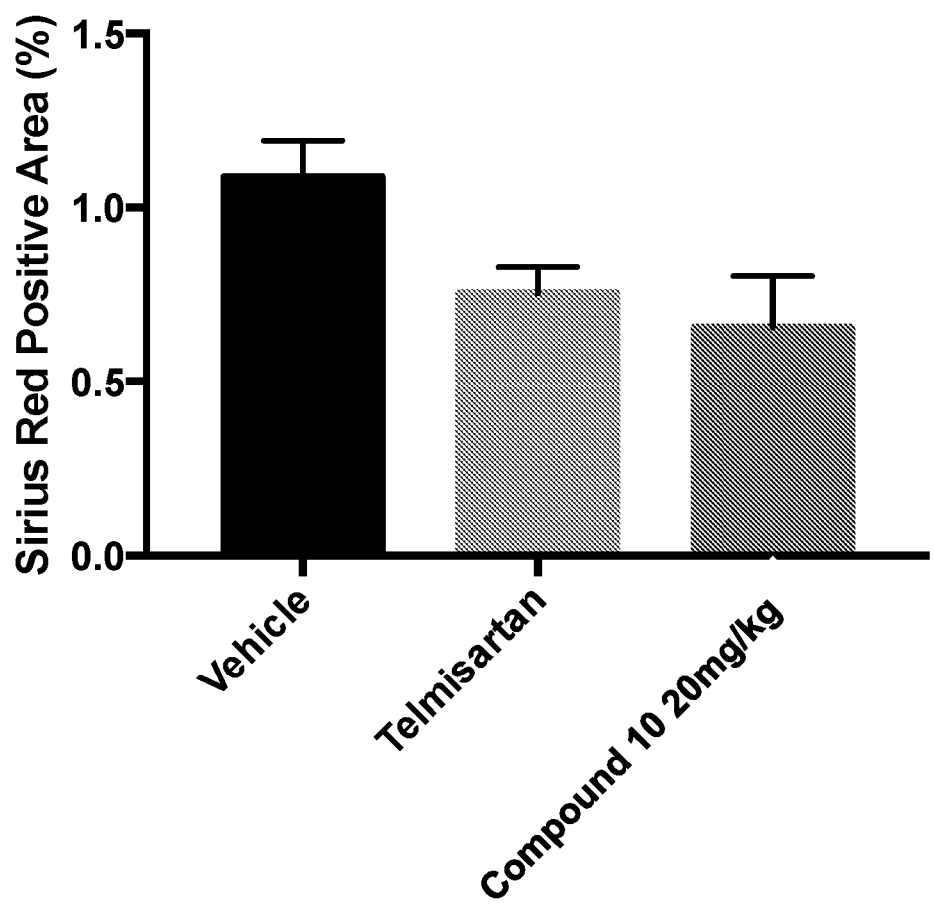
FIG. 13 shows the collagen content in the liver as measured histologically of Compound 10 by Sirius Red compared to vehicle and Telmisartan.

Histological analysis of the livers for collagen content was performed using Sirius Red staining. The staining was quantified and presented in FIG. 13. Treatment with Telmisartan or Compound 10 decreased levels of collagen in the liver compared to the vehicle treated group.

Distribution with In Vivo Imaging System

Figure 14:
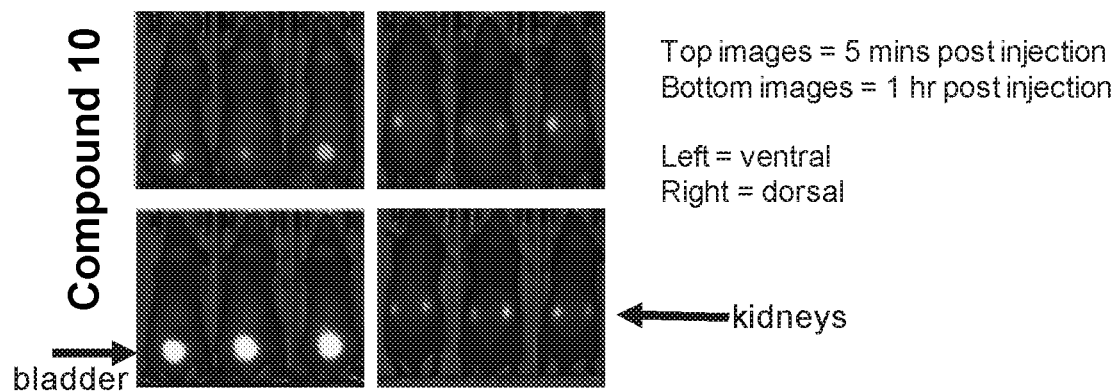
FIG. 14 shows IVIS imaging showing distribution of fluorescently labeled molecule in the kidneys and bladder. Top images were taken five minutes post IV injection, and bottom images were taken one hour post injection. Left images are the ventral side and right images are the dorsal side of the mice.

Compounds were synthesized with a fluorescent label. Specifically, CF633 was linked to the backbone via a hydrazide at a synthesis molar ratio of 1:1 dye to backbone. The molecules were intravenously dosed to nude mice at 10 mg/kg, and imaged using an In Vivo Imaging System (IVIS). At different time-points the animals were anesthetized and imaged using IVIS to determine biodistribution of the labeled compounds. FIG. 14 shows the localization of the compounds 5 or 60 minutes post injection. The compounds appeared to localize in the kidney and bladder.

Example 6: Collagen Binding Assay 2

Figure 18:
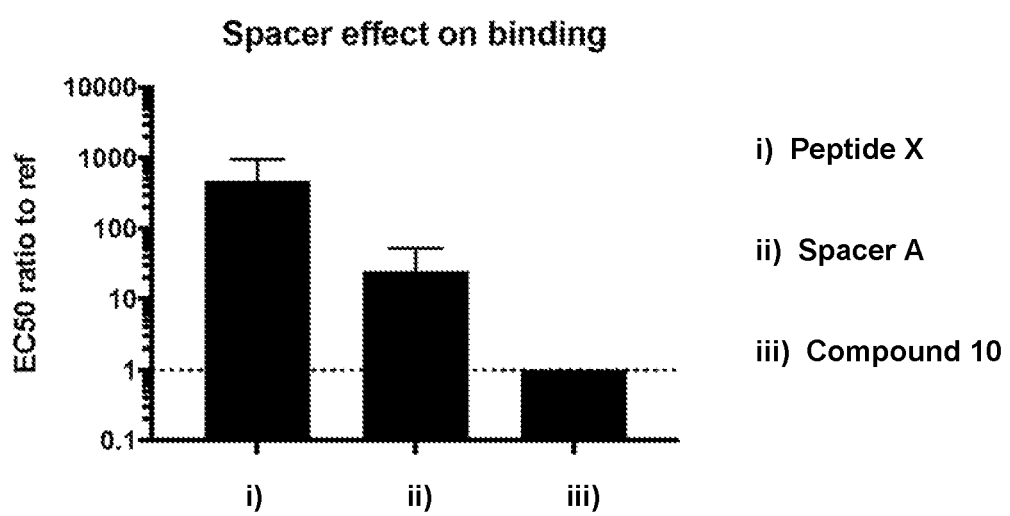
FIG. 18 shows a second collagen binding assay of the GQLYKSILY (SEQ ID NO: 5) binding sequence with optimized spacer sequence compared to the binding sequence with no spacer and the spacer sequence as a control.
Figure 19:
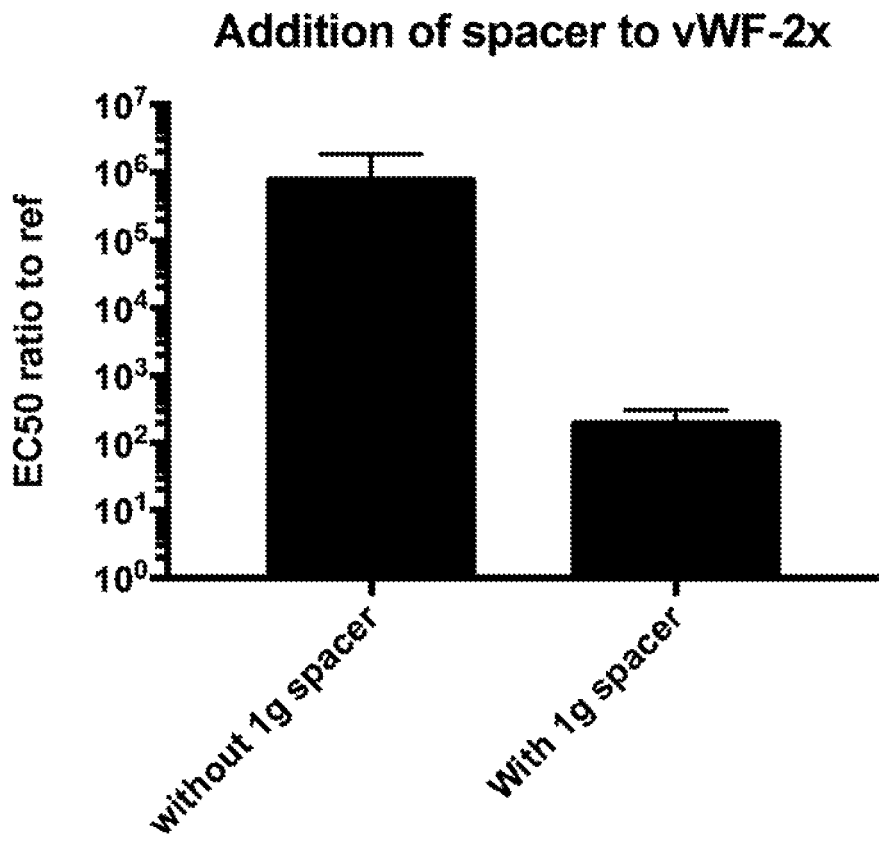

GQLYKSILYGSGSGSRR (SEQ ID NO: 6) (Compound 10) was evaluated for binding affinity against the GQLYKSILYGSG (SEQ ID NO: 59) (Peptide X) binding domain without spacer and against the spacer sequence alone, GSGSGSRR (SEQ ID NO: 4) (Spacer A), results shown in FIG. 18. The addition of the spacer resulted in greater binding affinity than the binding domain or the spacer in isolation. WREPSFSALS (SEQ ID NO: 8), also known as vWF-2x due to its binding to the von Willebran binding site on collagen, was evaluated for binding affinity with and without the GSGSGSRR (SEQ ID NO: 4) spacer. WREPSFSALSGSGSGSRR (SEQ ID NO: 110) WREPSFSALS (SEQ ID NO: 8) and GSGSGSRR (SEQ ID NO: 4) are shown in FIG. 19, upper right. Collagen bind assay showed an increase in binding affinity upon addition of spacer sequence.

50 μg/ml of Collagen Type I was adsorbed onto high bind plates by incubating overnight. Plates were then washed with PBS and blocked using 1% Non-fat milk in PBS for 1 hour. Molecule dilutions were prepared in 1% BSA in PBS and then incubated for 1 hour at 25° C. Plates were then washed with PBS containing 0.05% Tween 20. A 1:500 dilution of Streptavidin-HRP in 1% BSA PBS was prepared and added to the plates for 20 minutes. Plates were then washed with PBS and TMB solution was added for 10 minutes for color development. The color development was stopped using 0.16 M sulfuric acid and absorbance at 450 mm was measured using a plate reader. Compound 10 was used as a reference standard for all $EC_{50}$ results.

Figure 16:
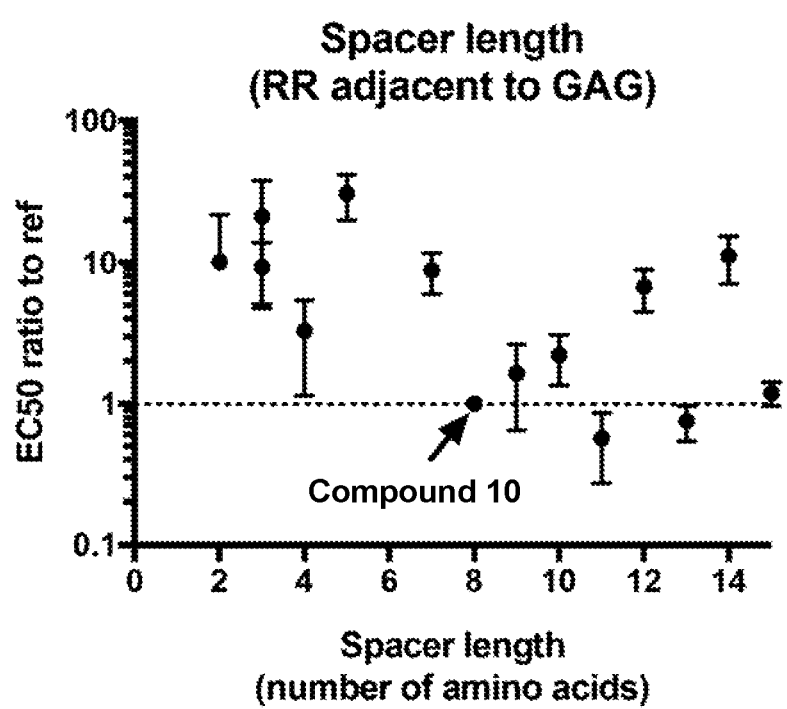
FIG. 16 shows the effect of spacer length on collagen binding when attached to GQLYKSILY (SEQ ID NO: 5) collagen binding domain.

The spacer length and chemical structure effects the collagen binding affinity of whole molecule. The spacer is generally comprised of a peptide sequence primarily of glycine and serine with some arginine residues. Glycine and serine sequence GSG can be replaced with aminohexanoic acid (Ahx). The location of the arginine residue plays a significant role in binding affinity. Positioning arginine residues closer to GAG improves collagen binding. (FIG. 15) Additionally, having multiple arginine residues increases collagen binding affinity. Spacer length positively corresponds to higher binding affinity (FIG. 16).

What is claimed is:

1. A bioconjugate comprising a glycan and from 1 to about 50 binding unit(s) of formula (I) covalently bonded thereto:

$$((X^1)_m X^2)_n X^3 - L \quad (I)$$

wherein:
$X^1$ is an amino acid sequence comprising a collagen-binding unit;
$X^2$ and $X^3$ are independently absent, are an amino acid sequence having from 1 to 15 amino acids, or area moiety

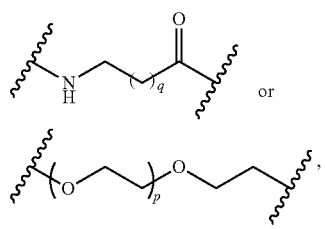

where p and q are each independently an integer from 1 to 10;
L is a spacer of from 7 to 20 amino acids selected from the group consisting of glycine (G), serine (S), arginine (R), and lysine (K), provided L comprises at least two arginines (R) within the first five amino acids from the glycan, and wherein L further comprises an optional linking moiety which covalently bonds to the glycan;
m is 1 or 2; and
n is 1 or 2.

2. The bioconjugate of claim 1, wherein:
$X^2$ is an amino acid sequence comprising GSG; and
$X^3$ is an amino acid sequence comprising XRR, where X is absent or is a natural or non-natural amino acid having a side chain capable of forming an amide bond.

3. The bioconjugate of claim 1, wherein the binding unit of formula (I) is $X^1$-GSGSGSRR— (SEQ ID NO: 4).

4. The bioconjugate of claim 1, wherein $X^1$ comprises from 3 to about 10 amino acids.

5. The bioconjugate of claim 1, wherein $X^1$ comprises the amino acid sequence RRANAALKAGELYKSILY (SEQ ID NO: 9).

6. The bioconjugate of claim 1, wherein $X^1$ comprises the amino acid sequence RRANAALKAGQLYKSILY (SEQ ID NO: 13).

7. The bioconjugate of claim 1, wherein $X^2$ comprises from 3 to 5 amino acids and $X^3$ comprises from 2 to 4 amino acids.

8. The bioconjugate of claim 1, wherein the glycan comprises from about 1 to about 50% functionalization, or from about 5 to about 30% functionalization, or about 25% functionalization, wherein the percent (%) functionalization is determined by a percent of disaccharide units on the glycan which are functionalized with the binding unit of formula (I).

9. The bioconjugate of claim 1, wherein the glycan is heparin or a derivative thereof.

10. The bioconjugate of claim 1, wherein the bioconjugate comprises about 8 or about 5 binding unit(s) of formula (I) covalently bonded thereto.

11. The bioconjugate of claim 1, wherein the binding unit is RRANAALKAGELYKSILYGSGSGSRR—NHNH— (SEQ ID NO: 128).

12. The bioconjugate of claim 1, wherein the binding unit is RRANAALKAGQLYKSILYGSGSGSRR—NHNH— (SEQ ID NO: 129).

13. The bioconjugate of claim 1, wherein the binding unit is GQLYKSILYGSGSGSRR—NHNH— (SEQ ID NO: 6).

14. The bioconjugate of claim 1, wherein the binding unit is (GQLYKSILYGSG)$_2$-KSGSRR—NHNH— (SEQ ID NO: 59 and SEQ ID NO: 130).

15. A bioconjugate comprising heparin conjugated to GQLYKSILYGSGRRGSG (SEQ ID NO: 95) in a 1:8 ratio or in a 1:5 ratio.

16. A binding unit of formula (II):

$$((X^1)_m X^2)_n X^3\text{-}L \quad (II)$$

wherein:
$X^1$ is an amino acid sequence comprising a collagen-binding unit comprising from 3 to about 10 amino acids;
$X^2$ and $X^3$ are independently absent, are an amino acid sequence having from 1 to 15 amino acids, or area moiety

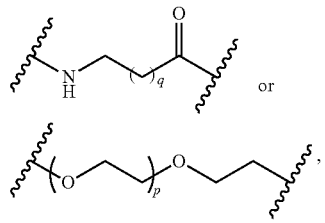

where p and q are each independently an integer from 1 to 10;
L is a spacer of from 7 to 20 amino acids selected from the group consisting of glycine (G), serine (S), arginine (R), and lysine (K), provided L comprises at least two arginines (R) within the first five amino acids from the terminus, and wherein L further comprises an optional linking moiety;
m is 1 or 2; and
n is 1 or 2;
provided that the binding unit is not RRRKKIQGRSKR (SEQ ID NO: 2) or RRGGRKWGSFEG (SEQ ID NO: 3).

17. The binding unit of claim 16, wherein:
$X^2$ is an amino acid sequence comprising GSG;
$X^3$ is an amino acid sequence comprising RR, KRR, GSG, or KGSG (SEQ ID NO: 73).

18. The binding unit of claim 16, wherein $X^1$ comprises the amino acid sequence GQLYKSILY (SEQ ID NO: 5) or the amino acid sequence RRANAALKAGELYKSILY (SEQ ID NO: 9).

19. A peptide having the amino acid sequence RRANAALKAGELYKSILYGSGSGSRR (SEQ ID NO: 128), RRANAALKAGELYKSILYGSGSGSRR—NHNH$_2$ (SEQ ID NO: 128), RRANAALKAGQLYKSILYGSGSGSRR (SEQ ID NO: 6), RRANAALKAGQLYKSILYGSGSGSRR—NHNH$_2$ (SEQ ID NO: 6), (GQLYKSILYGSG)$_2$-KSGSRR (SEQ ID NO: 59 and SEQ ID NO: 130), or (GQLYKSILYGSG)$_2$-KSGSRR—NHNH$_2$ (SEQ ID NO: 59 and SEQ ID NO: 130).

20. A method for treating peripheral artery disease in a patient in need thereof, comprising administering an effective amount of a bioconjugate of claim 19.

21. A method for treating fibrosis in a patient in need thereof, comprising administering an effective amount of a bioconjugate of claim 19.

22. The bioconjugate of claim 19, wherein L is selected from the group consisting of GSGSGRR (SEQ ID NO: 112), GSGSGSRR (SEQ ID NO: 4), GSGSGSGRR (SEQ ID NO: 113), GSGSGSGSRR (SEQ ID NO: 114), GSGSGSGSGRR (SEQ ID NO: 115), GSGSGSGSGSRR (SEQ ID NO: 116), GSGSGSGSGSGRR (SEQ ID NO: 117), GSGRRGSG (SEQ ID NO: 119), GSGRRRGSG (SEQ ID NO: 120), GSGRRRR (SEQ ID NO: 122), GSGSGSRRR (SEQ ID NO: 123), GSGSGSRRRR (SEQ ID NO: 124), GSGSGSRRRRR (SEQ ID NO: 125), GSGSGSRRRRRR (SEQ ID NO: 126), and GSGSGSGSRRR (SEQ ID NO: 127).

* * * * *